United States Patent
Anderson et al.

(10) Patent No.: US 12,357,365 B2
(45) Date of Patent: *Jul. 15, 2025

(54) VASCULAR ABLATION

(71) Applicant: Verge Medical Inc., Campbell, CA (US)

(72) Inventors: Edward Anderson, Maple Grove, MN (US); Adam Tschida, Brooklyn Park, MN (US); Randy Beyreis, Andover, MN (US); Scott Nelson, Mission Viejo, CA (US); JiChao Sun, Santa Rosa, CA (US); Laura Ortega, Fridley, MN (US); Joe Duerr, Andover, MN (US); Ae-Suk Pauling, St. Michael, MN (US); Dannah Dean, Minnetonka, MN (US); Doug Krone, Rogers, MN (US); Brady Hatcher, Rogers, MN (US)

(73) Assignee: Verge Medical Inc., Campbell, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/322,456

(22) Filed: May 23, 2023

(65) Prior Publication Data

US 2023/0310055 A1   Oct. 5, 2023

Related U.S. Application Data

(63) Continuation of application No. 17/697,739, filed on Mar. 17, 2022, now Pat. No. 11,696,793.
(Continued)

(51) Int. Cl.
*A61B 18/00* (2006.01)
*A61B 18/06* (2006.01)
(Continued)

(52) U.S. Cl.
CPC ......... *A61B 18/06* (2013.01); *A61M 5/14236* (2013.01); *A61B 2017/00323* (2013.01);
(Continued)

(58) Field of Classification Search
CPC .......... A61B 17/00008; A61B 17/3207; A61B 17/320758; A61B 2017/00778;
(Continued)

(56) References Cited

U.S. PATENT DOCUMENTS 4,728,319 A   3/1988   Masch
4,876,109 A   10/1989   Mayer
(Continued)

FOREIGN PATENT DOCUMENTS

CN      113143413 A    7/2021
EP      0501081 A1     9/1992
(Continued)

OTHER PUBLICATIONS

La Jolla Vein and Vascular—"Watch a ClariVein Procedure"—youtube.com [online] - Video by user La Jolla Vein and Vascular—Published Aug. 17, 2017—Available from Internet <URL: https://www.youtube.com/watch?v=q2f2vThzN40>.
(Continued)

*Primary Examiner* — William R Carpenter
*Assistant Examiner* — Robert F Allen
(74) *Attorney, Agent, or Firm* — Gallium Law; Jacob Panangat; Justin Schwechter

(57) ABSTRACT

The disclosure includes a vein ablation system, comprising a catheter having an elongated body. In some embodiments, the vein ablation system comprises an ablation device at a distal portion of the elongated body. According to some embodiments, the vein ablation system comprises a control device at a proximal portion of the elongated body. The control device may comprise an input mechanism config-
(Continued)

ured to simultaneously control at least two of a longitudinal translation of the ablation device through a target vessel, a rotation of the ablation device about a central longitudinal axis, and an infusion of a chemical agent into the target vessel.

20 Claims, 61 Drawing Sheets

Related U.S. Application Data

(60) Provisional application No. 63/270,547, filed on Oct. 21, 2021, provisional application No. 63/255,385, filed on Oct. 13, 2021, provisional application No. 63/163,728, filed on Mar. 19, 2021.

(51) Int. Cl.
*A61M 5/142* (2006.01)
*A61M 25/00* (2006.01)
*A61B 17/00* (2006.01)
*A61B 17/22* (2006.01)
*A61B 17/32* (2006.01)
*A61M 25/10* (2013.01)

(52) U.S. Cl.
CPC ... A61B 17/22004 (2013.01); A61B 17/32002 (2013.01); A61B 2018/00065 (2013.01); A61B 2018/0019 (2013.01); A61B 2018/00202 (2013.01); A61B 2018/00404 (2013.01); A61B 2218/002 (2013.01); A61M 25/0068 (2013.01); A61M 25/0082 (2013.01); A61M 2025/1086 (2013.01); A61M 2205/05 (2013.01); A61M 2205/3334 (2013.01); A61M 2210/12 (2013.01)

(58) Field of Classification Search
CPC .. A61B 2018/0019; A61B 2018/00202; A61B 2018/00577; A61B 18/1492; A61B 2017/00367; A61B 17/320725; A61B 2017/320733; A61B 2017/320741; A61B 17/22004; A61B 17/32002; A61B 2018/00065; A61B 2017/320004; A61B 17/320016; A61M 25/0082; A61M 25/0068; A61M 2205/05; A61M 2205/3334; A61M 2210/12; A61M 2202/0468; A61M 5/14236; A61M 25/007
See application file for complete search history.

(56) References Cited

U.S. PATENT DOCUMENTS

| | | | |
|---|---|---|---|
| 4,895,166 A | 1/1990 | Farr | |
| 4,990,134 A | 2/1991 | Auth | |
| 5,011,489 A | 4/1991 | Salem | |
| 5,022,399 A | 6/1991 | Biegeleisen | |
| 5,058,570 A | 10/1991 | Idemoto | |
| 5,074,871 A | 12/1991 | Groshong | |
| 5,085,662 A | 2/1992 | Willard | |
| 5,135,517 A | 8/1992 | McCoy | |
| 5,226,909 A | 7/1993 | Evans | |
| 5,282,484 A | 2/1994 | Reger | |
| 5,312,427 A | 5/1994 | Shturman | |
| 5,356,418 A | 10/1994 | Shturman | |
| 5,361,768 A | 11/1994 | Webler | |
| 5,370,653 A | 12/1994 | Cragg | |
| 5,372,601 A | 12/1994 | Lary | |
| 5,383,460 A | 1/1995 | Jang | |
| 5,402,790 A | 4/1995 | Jang | |
| 5,415,636 A | 5/1995 | Forman | |
| 5,549,601 A | 8/1996 | McIntyre | |
| 5,584,843 A | 12/1996 | Wulfman | |
| 5,836,905 A | 11/1998 | Lemelson | |
| 5,842,993 A | 12/1998 | Eichelberger | |
| 5,843,103 A * | 12/1998 | Wulfman | A61B 17/320758 606/159 |
| 5,851,208 A | 12/1998 | Trott | |
| 5,882,329 A | 3/1999 | Patterson | |
| 5,893,858 A | 4/1999 | Spitz | |
| 5,895,400 A | 4/1999 | Abela | |
| 5,902,266 A | 5/1999 | Leone | |
| 5,908,395 A | 6/1999 | Stalker | |
| 5,921,963 A | 7/1999 | Erez | |
| 6,004,271 A | 12/1999 | Moore | |
| 6,048,332 A | 4/2000 | Duffy | |
| 6,090,118 A | 7/2000 | McGuckin | |
| 6,111,614 A | 8/2000 | Mugura | |
| 6,159,196 A | 12/2000 | Ruiz | |
| 6,165,187 A | 12/2000 | Reger | |
| 6,193,735 B1 | 2/2001 | Stevens | |
| 6,193,736 B1 | 2/2001 | Webler | |
| 6,221,087 B1 * | 4/2001 | Anderson | A61B 17/320758 606/159 |
| 6,231,518 B1 | 5/2001 | Grabek | |
| 6,258,087 B1 | 7/2001 | Edwards | |
| 6,273,882 B1 | 8/2001 | Whittier | |
| 6,290,675 B1 | 9/2001 | Vujanic | |
| 6,319,227 B1 | 11/2001 | Mansouri-Ruiz | |
| 6,398,755 B1 * | 6/2002 | Belef | A61M 25/0113 604/95.01 |
| 6,402,745 B1 * | 6/2002 | Wilk | A61B 18/1492 606/41 |
| 6,485,482 B1 | 11/2002 | Belef | |
| 6,517,528 B1 | 2/2003 | Pantages | |
| 6,520,928 B1 | 2/2003 | Rosa | |
| 6,602,264 B1 | 8/2003 | McGuckin | |
| 6,723,082 B1 * | 4/2004 | Payne | A61B 18/24 604/528 |
| 6,733,473 B1 | 5/2004 | Reifart | |
| 6,814,727 B2 | 11/2004 | Mansouri-Ruiz | |
| 6,818,001 B2 | 11/2004 | Wulfman | |
| 6,852,118 B2 | 2/2005 | Shturman | |
| 6,926,725 B2 | 8/2005 | Cooke | |
| 7,037,316 B2 | 5/2006 | McGuckin | |
| 7,077,836 B2 | 7/2006 | Lary | |
| 7,083,643 B2 | 8/2006 | Whalen | |
| 7,211,073 B2 | 5/2007 | Fitzgerald | |
| 7,285,126 B2 | 10/2007 | Sepetka | |
| 7,402,155 B2 | 7/2008 | Palasis | |
| 7,419,482 B2 | 9/2008 | Nash | |
| 7,479,147 B2 | 1/2009 | Honeycutt | |
| 7,507,246 B2 | 3/2009 | McGuckin | |
| 7,613,493 B2 | 11/2009 | Mansouri-Ruiz | |
| 7,670,328 B2 | 3/2010 | Miller | |
| 7,713,231 B2 | 5/2010 | Wulfman | |
| 7,819,887 B2 | 10/2010 | McGuckin | |
| 7,862,575 B2 * | 1/2011 | Tal | A61B 17/00008 606/159 |
| 7,909,836 B2 | 3/2011 | McLean | |
| 7,967,834 B2 | 6/2011 | Tal | |
| 7,985,200 B2 | 7/2011 | Lary | |
| 8,038,664 B2 | 10/2011 | Miller | |
| 8,062,316 B2 | 11/2011 | Patel | |
| 8,202,244 B2 | 6/2012 | Cohen | |
| 8,460,214 B2 | 6/2013 | Kuban | |
| 8,465,508 B2 | 6/2013 | Tal | |
| 8,491,539 B2 | 7/2013 | Fojtik | |
| 8,535,290 B2 | 9/2013 | Evans | |
| 8,632,520 B2 | 1/2014 | Otley | |
| 8,657,821 B2 | 2/2014 | Palermo | |
| 8,690,833 B2 | 4/2014 | Belson | |
| 8,696,645 B2 | 4/2014 | Tal | |
| 8,986,241 B2 | 3/2015 | Evans | |
| 8,992,482 B2 | 3/2015 | Fojtik | |
| 9,022,971 B2 | 5/2015 | Fojtik | |
| 9,162,037 B2 | 10/2015 | Belson | |
| 9,375,216 B2 | 6/2016 | Tal | |
| 9,440,046 B2 | 9/2016 | Hobbs | |
| 9,457,153 B2 | 10/2016 | Marano | |
| 9,480,467 B2 | 11/2016 | Marano | |

(56) References Cited

U.S. PATENT DOCUMENTS

| | | |
|---|---|---|
| 9,585,667 B2 | 3/2017 | Tal |
| 9,700,347 B2 | 7/2017 | Shiber |
| 9,737,329 B2 | 8/2017 | Shturman |
| 9,924,957 B2 | 3/2018 | McGuckin |
| 10,117,671 B2 | 11/2018 | McGuckin |
| 10,207,057 B2 | 2/2019 | Fojtik |
| 10,368,902 B2 | 8/2019 | Kesller |
| 10,405,878 B2 | 9/2019 | WasDyke |
| 10,463,388 B2 | 11/2019 | Tal |
| 10,555,752 B2 | 2/2020 | Robertson |
| 10,561,440 B2 | 2/2020 | Look |
| 10,702,300 B2 | 7/2020 | Higgins |
| 11,006,935 B2 | 5/2021 | Brandeis |
| 11,134,967 B2 | 10/2021 | Guerra et al. |
| 11,154,313 B2 | 10/2021 | Miller |
| 11,172,984 B2 | 11/2021 | Sharma et al. |
| 11,191,561 B2 | 12/2021 | Konyo |
| 11,213,314 B1 | 1/2022 | Robinson et al. |
| 11,241,250 B2 | 2/2022 | Tal et al. |
| 11,253,292 B2 | 2/2022 | McGuckin, Jr. et al. |
| 11,266,436 B2 | 3/2022 | Farago et al. |
| 11,272,954 B2 | 3/2022 | Piippo Svendsen et al. |
| 11,304,718 B2 | 4/2022 | Cox |
| 11,331,119 B2 | 5/2022 | Flury et al. |
| 11,337,724 B2 | 5/2022 | Masubuchi et al. |
| 11,369,384 B2 | 6/2022 | Raabe et al. |
| 11,389,191 B2 | 7/2022 | Nakano et al. |
| 11,419,629 B2 | 8/2022 | Hatta et al. |
| 11,426,193 B2 | 8/2022 | Kessler |
| 11,432,841 B2 | 9/2022 | Steele |
| 11,439,417 B2 | 9/2022 | Weitzner et al. |
| 11,446,053 B2 | 9/2022 | Jamous et al. |
| 11,452,541 B2 | 9/2022 | Lippert et al. |
| 11,478,270 B2 | 10/2022 | Carlson et al. |
| 11,696,793 B2 * | 7/2023 | Anderson .......... A61B 18/1492 604/509 |
| 2001/0004700 A1 | 6/2001 | Honeycutt |
| 2001/0041909 A1 | 11/2001 | Tsugita |
| 2002/0010418 A1 | 1/2002 | Lary |
| 2002/0188276 A1 | 12/2002 | Evans |
| 2003/0004568 A1 | 1/2003 | Ken |
| 2003/0225435 A1 | 12/2003 | Huter |
| 2004/0147934 A1 | 7/2004 | Kiester |
| 2004/0254566 A1 | 12/2004 | Plicchi |
| 2006/0189929 A1 | 8/2006 | Lary |
| 2007/0239140 A1 | 10/2007 | Chechelski |
| 2008/0097224 A1 | 4/2008 | Murphy |
| 2008/0183129 A1 | 7/2008 | Silverman |
| 2010/0125276 A1 | 5/2010 | Palermo |
| 2010/0217313 A1 | 8/2010 | Raabe |
| 2012/0059309 A1 | 3/2012 | di Palma |
| 2012/0109191 A1 | 5/2012 | Marano, Jr. |
| 2012/0130415 A1 | 5/2012 | Tal |
| 2013/0294189 A1 | 11/2013 | Myrick |
| 2014/0207052 A1 | 7/2014 | Tal |
| 2015/0005792 A1 | 1/2015 | Ahn |
| 2015/0126965 A1 | 5/2015 | Liungman |
| 2015/0151048 A1 * | 6/2015 | Okamoto ............ A61B 5/4827 604/117 |
| 2015/0190127 A1 | 7/2015 | Madsen |
| 2015/0201956 A1 * | 7/2015 | Higgins ......... A61B 17/320725 606/159 |
| 2016/0030023 A1 | 2/2016 | Hayakawa |
| 2016/0030719 A1 | 2/2016 | Hayakawa |
| 2016/0242790 A1 | 8/2016 | Brandeis |
| 2016/0263319 A1 * | 9/2016 | Brandeis ............... A61M 1/815 |
| 2016/0302822 A1 | 10/2016 | Tal |
| 2017/0065396 A1 * | 3/2017 | Look ................ A61B 17/32037 |
| 2019/0125322 A1 | 5/2019 | Brandeis |
| 2019/0307483 A1 * | 10/2019 | Flury ............. A61B 17/320758 |
| 2020/0113575 A1 | 4/2020 | Wisnosky |
| 2020/0113577 A1 * | 4/2020 | Wisnosky ........ A61B 17/12109 |
| 2020/0138475 A1 | 5/2020 | Tal |
| 2020/0178980 A1 | 6/2020 | Hill |
| 2020/0246042 A1 | 8/2020 | Plowiecki |
| 2020/0254216 A1 * | 8/2020 | Varun ............... A61M 25/0069 |
| 2020/0269019 A1 | 8/2020 | Rollins |
| 2021/0177455 A1 | 6/2021 | Jamous |

FOREIGN PATENT DOCUMENTS

| | | |
|---|---|---|
| EP | 3165184 A1 | 5/2017 |
| EP | 3206590 A1 | 8/2017 |
| EP | 2629828 B1 | 12/2021 |
| EP | 3448285 B1 | 6/2022 |
| EP | 3737310 B1 | 7/2022 |
| EP | 3313303 B1 | 11/2022 |
| JP | 2007301392 A | 11/2007 |
| JP | 2009254874 A | 11/2009 |
| JP | 5622938 B2 | 11/2014 |
| JP | 6987274 B2 | 12/2021 |
| KR | 101539142 B1 | 7/2015 |
| RU | 2699009 C1 | 9/2019 |
| RU | 196638 U1 | 3/2020 |
| WO | 1994021177 A1 | 9/1994 |
| WO | 1999004701 A1 | 2/1999 |
| WO | 1999047056 A1 | 9/1999 |
| WO | 2001008561 A1 | 2/2001 |

OTHER PUBLICATIONS

DAIC—"Trellis-8 Infusion Catheter Busts DVT Clots"—Diagnostic and Interventional Cardiology [magazine]—dicardiology.com [online]—Mar. 17, 2008—Available from Internet <URL: https://www.dicardiology.com/product/trellis-8-infusion-catheter-busts-dvt-clots>.

NYC Surgical Associates—"Deep Vein Thrombosis Treatment With Trellis Procedure—NYC Surgical Associates"—youtube.com [online]—Video by user NYC Surgical Associates—Published Apr. 12, 2014—Available from Internet <URL: https://www.youtube.com/watch?v=50LzxuleYUc>.

Cook Medical—"Coda® Balloon Catheter"—cookmedical.com [online]—Site visited Sep. 23, 2021—Available from Internet <URL: https://www.cookmedical.com/products/829e48bc-8fa0-43e5-9530-11ded12b6a42/>.

MEDTRONIC—"VenaSeal™ closure system for superficial vein therapies"—Site visited Sep. 23, 2021—Available from Internet <URL: https://www.medtronic.com/us-en/healthcare-professionals/products/cardiovascular/superficial-vein/venaseal-closure-system.html>.

MEDTRONIC—"VenaSeal™ Closure System VS-402"—manuals.medtronic.com [online]—Website publication date: Apr. 6, 2018—Available from Internet <URL: https://manuals.medtronic.com/content/dam/emanuals/cardio/MS-510522-001_RevB_view_color.pdf>.

Williams R. A., Wilson S. E.—"Sclerosant Treatment of Varicose Veins and Deep Vein Thrombosis"—Arch Surg—Nov. 1984—vol. 119, No. 11, p. 1283-1285—JAMA Surgery—<doi: 10.1001/archsurg.1984.01390230053012>.

Rose D., Larnicol N., Duron B.—"The cat cervical dorsal root ganglia: general cell-size characteristics and comparative study of neck muscle, neck cutaneous and phrenic afferents"—Neuroscience Research—Feb. 1990—vol. 7, No. 4, p. 341-357—Elsevier Scientific Publishers Ireland Ltd.—<doi: 10.1016/0168-0102(90)90009-4>.

Attaran, Rob—"ClariVein Animation Sequence"—youtube.com [online]—Video by user Rob Attaran—Published Feb. 13, 2018—Available from Internet <URL: https://www.youtube.com/watch?v=0R2khsxBYuk>.

CV Technologies—"FLEBOGRIF"—cvtechnologies.in [online]—Site visited Sep. 23, 2021—Available from Internet <URL: http://cvtechnologies.in/flebogrif/>.

Vascular Insights, LLC—"Clarivein® IC, Infusion Catheter"—clarivein.com [online]—Available at least as of 2016—Site visited Sep. 23, 2021—Available from Internet <URL: https://clarivein.com/wp-content/uploads/2015/07/IFU-001-Instruction-for-Use-IC-REV-B.pdf>.

(56) References Cited

OTHER PUBLICATIONS

Balton SP. Z O. O.—"Flebogrif Set for Varicose Veins Treatment"—youtube.com [online]—Video by user Balton Sp. z o. o.—Published Apr. 8, 2019—Available from Internet <URL: https://www.youtube.com/watch?v=d49LpQb-SQo&t=6s>.

Venturemed Group—"FLEX Vessel Prep System"—youtube.com [online]—Video by user VentureMed Group—Published Oct. 17, 2019—Available from Internet <URL: https://www.youtube.com/watch?v=r1RwTRFbgK4>.

TELEFLEX—"Arrow-Trerotola™ PTD®"—Available at least as of 2012—Retrieved Sep. 23, 2021—Available from Internet <URL: https://studylib.net/doc/8350860/arrow-trerotola%E2%84%A2-ptd%C2%AE-p>.

\* cited by examiner

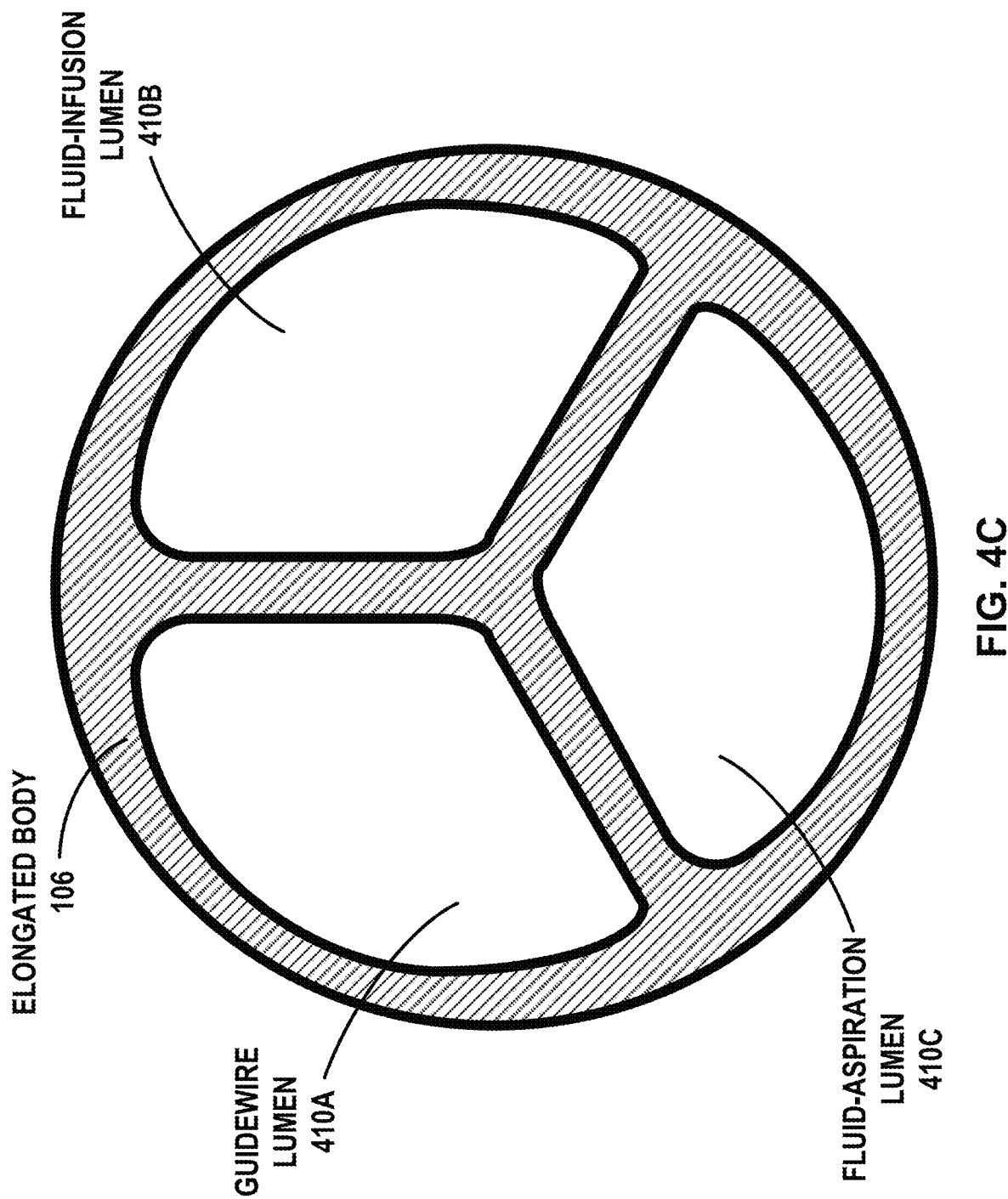

VASCULAR ABLATION

CROSS-REFERENCE TO RELATED APPLICATIONS

The entire contents of the following application are incorporated by reference herein: U.S. Provisional Patent Application No. 63/163,728; filed Mar. 19, 2021; and entitled ENDOVASCULAR DEVICES AND METHODS.

The entire contents of the following application are incorporated by reference herein: U.S. Provisional Patent Application No. 63/255,385; filed Oct. 13, 2021; and entitled VEIN ABLATION SYSTEMS AND METHODS.

The entire contents of the following application are incorporated by reference herein: U.S. Provisional Patent Application No. 63/270,547; filed Oct. 21, 2021; and entitled VEIN ABLATION SYSTEMS AND METHODS.

The entire contents of the following application are incorporated by reference herein: U.S. patent application Ser. No. 17/697,739; filed Mar. 17, 2022; and entitled VASCULAR ABLATION.

INTRODUCTION

Technical Field

The present disclosure relates to intravascular medical devices.

BACKGROUND

Sclerotherapy is a medical procedure for treating certain vascular disorders, such as varicose veins. Current sclerotherapy treatments include some combination of the following three elements: mechanically ablating (e.g., disrupting or agitating) an interior surface of a target vessel with an ablation device; longitudinally (e.g., proximally and/or distally) translating the ablation device through the target vessel while the ablation device is actuated; and infusing a chemical agent (e.g., a sclerosant) into the target vessel.

SUMMARY

Systems and techniques are disclosed herein for treating vascular disorders, such as varicose veins, through mechanical and/or chemical ablation of a target vessel. As detailed further below, in some examples, an ablation system includes a catheter having a distal ablation device and a proximal control device (e.g., handle) configured to control the ablation device. In particular, the control device includes one or more user controls (e.g., user-input mechanisms) enabling the user to control at least two different functions of the treatment simultaneously.

In some examples, a vessel ablation system includes a catheter having an elongated body. In some examples, the vein ablation system comprises an ablation device at a distal portion of the elongated body. According to some examples, the vein ablation system comprises a control device at a proximal portion of the elongated body. The control device may comprise an input mechanism configured to simultaneously control at least two of a proximal retraction of the ablation device through a target vessel, a rotation of the ablation device about a central longitudinal axis, and an infusion of a chemical agent into the target vessel.

In some examples, the input mechanism is configured to simultaneously control the proximal retraction and the rotation of the ablation device. According to some examples, the vein ablation system further comprises a first track disposed within a lumen of the elongated body. The vein ablation system may further comprise a second track disposed within the lumen of the elongated body. In some examples, the vein ablation system further comprises a worm gear. According to some examples, the vein ablation system further comprises a thumb wheel operatively coupled to the first track, the second track, and the worm gear, the thumb wheel arranged and configured to simultaneously move the first track and the second track simultaneously in opposing directions along a first direction, and rotate the ablation device about the first direction via the worm gear.

The elongated body may define a fluid infusion lumen and a fluid aspiration, the control device arranged and configured to remove blood from the target vessel via the fluid aspiration lumen while the ablation device delivers the chemical agent to the target vessel via the fluid infusion lumen.

In some examples, the ablation device comprises at least one ablating wire configured to contact an interior surface of the target vessel. According to some examples, the at least one ablating wire is arranged and configured to mechanically ablate the target vessel by piercing the interior surface of the target vessel. The distal portion of the at least one ablating wire may comprise a spherical tip. In some examples, the at least one ablating wire is arranged and configured to deliver the chemical agent to the target vessel.

According to some examples, the chemical agent comprises a sclerosant. The vein ablation system may further comprise a foaming agent cartridge detachably coupled to the control device, the foaming agent cartridge arranged and configured to release a foaming agent to create a foam when mixed with the sclerosant.

In some examples, the vein ablation system further comprises a continuous-feed tube operatively coupled to a piston configured to concurrently proximally retract the ablation device and infuse the chemical agent. According to some examples, the control device comprises means for enabling a user to control a rate of infusion of the chemical agent relative to a distance of proximal retraction of the ablation device. The chemical agent may comprise a cryoablation agent.

In some examples, the vein ablation system further comprises a motor configured to proximally retract the ablation device and to deliver the chemical agent via a fluid infusion lumen of the elongated body. According to some examples, the control device further comprises a distance display configured to indicate a distance between the control device and the ablation device.

The vein ablation system may further comprise an expandable member disposed at the distal portion of the elongated body. In some examples, the control device is configured to cause the expandable member to expand radially outward by infusing the chemical agent. According to some examples, the expandable member defines a plurality of pores configured to release the chemical agent. The control device may comprise a reusable control device, and wherein the elongated body and the ablation device are removably coupled to the control device.

In some examples, the elongated body defines a guidewire lumen, a fluid infusion lumen, and a fluid aspiration lumen.

According to some examples, the ablation device comprises a plurality of elongated tines configured to expand radially outward to contact the interior surface of the target vessel. The elongated tines may extend generally parallel to a central longitudinal axis of the elongated body. In some examples, the elongated tines twist helically about an internal axis of the elongated tines. According to some examples, the elongated tines extend generally helically about the distal portion of the elongated body.

The vein ablation system may further comprise a distal stopper configured to retain the chemical agent within the target vessel. In some examples, the distal stopper comprises a nickel-titanium skirt and shroud.

According to some examples, the ablation device comprises a plurality of elongated microtubes each defining at least one pore configured to release the chemical agent. Each elongated microtube may further comprise a shape-memory coil configured to expand the microtube to a predetermined configuration. In some examples, each elongated microtube defines a plurality of pores along an exterior surface of the microtube. According to some examples, each elongated microtube defines one pore near a distalmost end of the microtube.

The ablation device may comprise a plurality of vein-scratchers configured to self-expand radially outward to contact the interior surface of the target vessel. In some examples, the vein ablation system further comprises an Archimedes screw disposed within a lumen of the elongated body, the Archimedes screw configured to distally pump the chemical agent toward the target vessel. According to some examples, the vein ablation system further comprises a pulley system configured to translate a rotational motion of a motor of the control device into a proximal linear motion of the ablation device.

The control device may comprise a slider configured to proximally retract the ablation device. In some examples, the slider comprises a curved trigger. According to some examples, the slider comprises a heart-shaped pullback mechanism.

The control device may be configured to cause the proximal portion of the elongated body to coil within the control device as the control device causes the ablation device to proximally retract. In some examples, the control device is configured to release the chemical agent retained within the proximal portion of the elongated body as the elongated body coils within the control device.

According to some examples, the elongated body comprises a plurality of wings configured to extend radially outward to contact the interior surface of the target vessel. The vein ablation system may further comprise a rotating diffuser brush configured to disperse the chemical agent along the interior surface of the target vessel. In some examples, the vein ablation system further comprises a rotating hypotube offset from the central longitudinal axis, the rotating hypotube configured to release the chemical agent through a plurality of pores.

According to some examples, the elongated body defines a sinusoidal shape, and wherein the elongated body is configured to rotate about the central longitudinal axis. The elongated body may define a plurality of pores configured to release the chemical agent. In some examples, the vein ablation system further comprises an interventional balloon retaining the sinusoidal elongated body, wherein the sinusoidal elongated body is configured to rotate to infuse the chemical agent through a porous membrane of the balloon.

According to some examples, the ablation device comprises a wire loop configured to contact the interior surface of the target vessel. The vein ablation system may further comprise a revolver mechanism configured to rotatably engage a plurality of syringes with a fluid infusion lumen of the elongated body. In some examples, the vein ablation system further comprises a weeping roller offset from the central longitudinal axis, the weeping roller configured to rotate about the central longitudinal axis and to revolve about a central axis of the roller to infuse the chemical agent. According to some examples, the vein ablation system further comprises a bioabsorbable plug configured to occlude a distal portion of the target vessel.

The vein ablation system may further comprise a porous balloon configured to release the chemical agent. In some examples, the proximal portion of the elongated body comprises an inflatable balloon configured to form a vacuum to retain the chemical agent within the target vessel. According to some examples, the vein ablation system further comprises a proximal balloon and a distal balloon, the proximal and distal balloons configured to inflate to straighten a portion of the target vessel disposed between the proximal balloon and the distal balloon. The vein ablation system may further comprise a balloon positioned within a shape-memory-material cage configured to cause the balloon to self-expand radially outward.

BRIEF DESCRIPTION OF THE DRAWINGS

These and other features, aspects, and advantages are described below with reference to the drawings, which are intended to illustrate, but not to limit, the invention. In the drawings, like characters denote corresponding features consistently throughout similar embodiments.

FIGS. 4A-4C are cross-sectional views through three examples of the catheter of FIG. 1.

Figure 1:
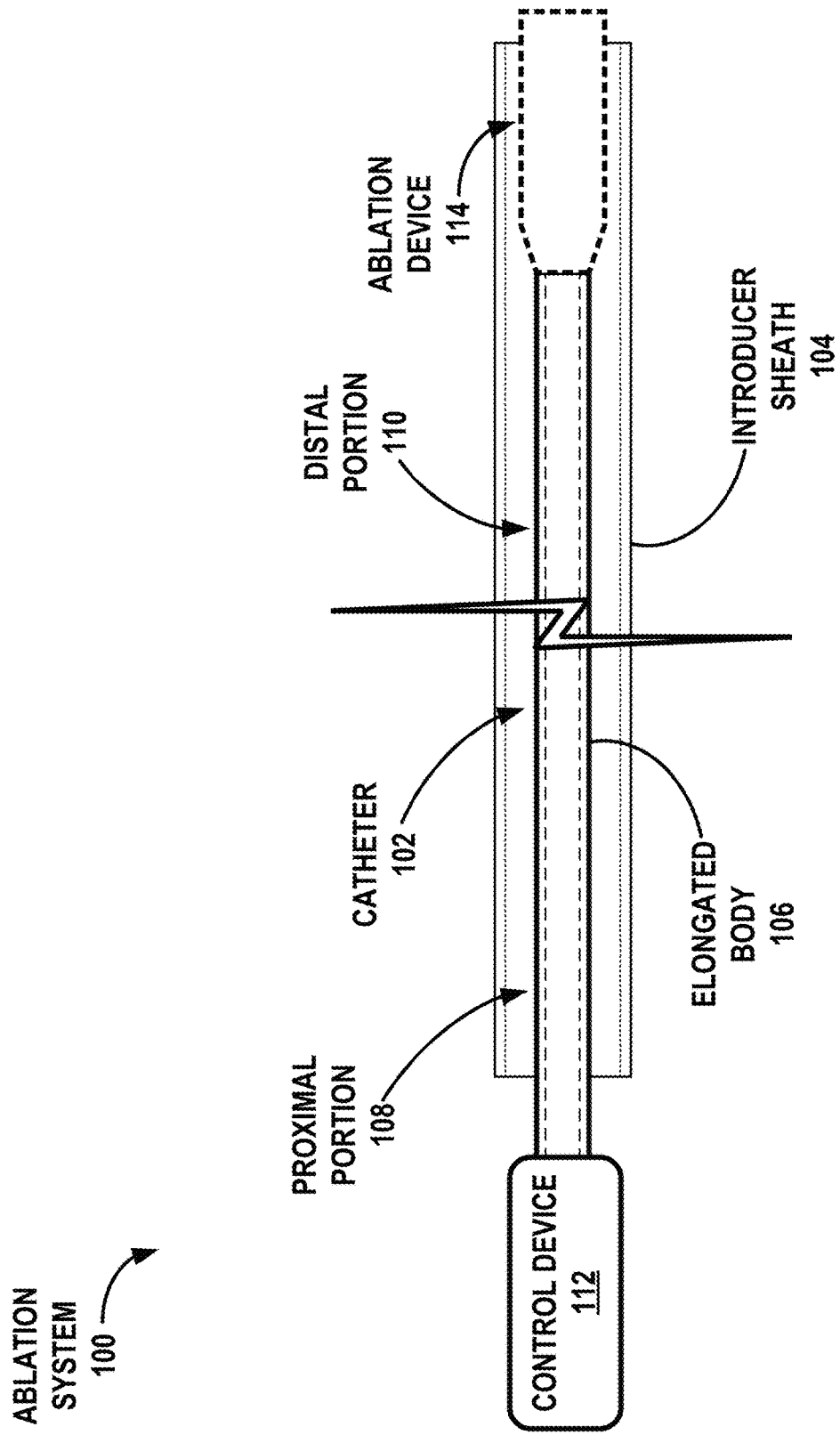
FIG. 1 is a conceptual diagram of an ablation system including a catheter having a proximal control device and a distal ablation device.

| COMPONENT INDEX |
|---|
| 100 - Ablation System |
| 102 - Catheter |
| 104 - Introducer Sheath |
| 106 - Elongated Body |
| 108 - Proximal Catheter Portion |
| 110 - Distal Catheter Portion |
| 112 - Proximal Control Device |
| 114 - Distal Ablation Device |
| 202 - Target Vessel |
| 204 - Agitator |
| 206 - Fluid Reservoir |
| 208 - Chemical Agent |
| 210 - Inner Lumen |
| 212 - User Control |
| 214 - Central Longitudinal Axis |
| 216 - Vessel Occluder |
| 300A - Non-Sterile Environment |
| 300B - Sterile Environment |
| 302 - Single-Use Catheter |
| 304 - Reusable Control Device |
| 306 - Connection Interface |
| 308 - Agitator Input |
| 310 - Infusion Input |
| 312 - Translation Input |
| 314 - Rate Input(s) |
| 316 - Agitator Driver |
| 318 - Translation Driver |
| 402 - Outer Tube |
| 404 - Middle Tube |
| 406 - Inner Tube |
| 408 - Inner Elongated Member |
| 410A - Guidewire Lumen |
| 410B - Fluid-Infusion Lumen |
| 410C - Fluid-Aspiration Lumen |
| 504 - Straight-Tine Agitator |
| 506 - Elongated Tines |
| 510 - Distal Catheter Mouth |
| 514 - Ablation Device |
| 604 - Spiral-Tine Agitator |
| 606 - Elongated Tines |
| 608 - Spherical Tip |
| 614 - Ablation Device |
| 706 - Fluid Microtubes |
| 714 - Ablation Device |
| 806A - Shape-Memory Fluid Microtube |
| 806B - Single-Aperture Fluid Microtube |
| 806C - Porous Fluid Microtube |
| 808 - Shape-Memory Coil |
| 810 - Fluid Aperture(s) |
| 902 - Agitator Retainer |
| 904 - Self-Expanding Agitator |
| 906 - Elongated Tines |
| 910 - Weeping Balloon |
| 914 - Ablation Device |
| 1004 - Self-Expanding Agitator |
| 1006 - Elongated Tines |
| 1012 - Apertures |
| 1014 - Ablation Device |

| COMPONENT INDEX |
| --- |
| 1016 - Interventional Balloon |
| 1100 - Gear-and-Track Mechanism |
| 1102 - Gear |
| 1104 - Tracks |
| 1200 - Worm-Gear Mechanism |
| 1202 - Worm Gear |
| 1204 - Longitudinal Shaft |
| 1206 - Coiled Thread |
| 1208 - Wheel Gear |
| 1300 - Dual-Worm-Gear Mechanism |
| 1304A - Outer Shaft |
| 1304B - Inner Shaft |
| 1306A - Outer Coiled Thread |
| 1306B - Inner Coiled Thread |
| 1308 - Thumbwheel |
| 1402 - Forward Spur Gear Mechanism |
| 1404 - Thumbwheel |
| 1406 - Wheel Axis |
| 1408 - Wheel Gear |
| 1410 - Syringe Plunger |
| 1412 - Control Device |
| 1414 - Catheter Rollers |
| 1502 - Rear Spur Gear Mechanism |
| 1504 - Housing Aperture |
| 1506 - Housing |
| 1508 - Syringe Teeth |
| 1510 - Trigger Lock |
| 1512 - Control Device |
| 1600 - Pulley Mechanism |
| 1602 - Motor |
| 1604 - Pulley Wheel |
| 1612 - Control Device |
| 1700 - Reverse Pulley Mechanism |
| 1704 - Housing Aperture |
| 1706 - Housing |
| 1708 - Pulley Wheels |
| 1710 - Knobs |
| 1712 - Control Device |
| 1802 - Straight-Syringe Catheter |
| 1806 - Elongated Body |
| 1808 - Proximal Portion |
| 1810 - Distal Portion |
| 1812 - Control Knob |
| 1816 - Displacement Indicator |
| 1818 - Grip |
| 1820 - Indicator Handle |
| 1822 - Distal Mouth |
| 2002 - Slider |
| 2002A - Retracted Slider Position |
| 2002B - Advanced Slider Position |
| 2006 - Housing |
| 2012 - Control Device |
| 2016 - Displacement Indicator |
| 2022 - Distal Mouth |
| 2102 - User Control |
| 2104 - Thumbwheel |
| 2112 - Control Device |
| 2202A - Proximal Balloon |
| 2202B - Distal Balloon |
| 2206 - Mechanical Agitator |
| 2214 - Ablation Device |
| 2302 - Continuous Feed Tube |
| 2304 - Piston |
| 2306 - User Control |
| 2308 - Top Portion |
| 2310 - Bottom Portion |
| 2312 - Control Device |
| 2402 - Coiled Feed Tube |
| 2404 - User Control |
| 2412 - Control Device |
| 2502A - Catheter Wings |
| 2502B - Catheter Wings |
| 2502C - Wire Wings |
| 2504 - Wires |
| 2514 - Ablation Device |
| 2602A-2602C - Brushes |
| 2614 - Ablation Device |

| COMPONENT INDEX |
| --- |
| 2702A, 2702B - Rotating Hypotubes |
| 2704 - Abrading Surface |
| 2714 - Ablation Device |
| 2804 - Sinusoidal Agitator |
| 2814 - Ablation Device |
| 2902 - Distal Wire Tip |
| 2904A, 2904B - Wire Agitators |
| 2914 - Ablation Device |
| 3002 - Rotary Syringe Holder |
| 3004 - Syringes |
| 3006 - Y-Hub |
| 3008 - Plunger |
| 3012 - Control Device |
| 3114 - Ablation Device |
| 3102A-3102C - Weeping Rollers |
| 3202A-3202H - Bioabsorbable Plugs |
| 3204 - Outer Plug Layer |
| 3206 - Inner Plug Balloon |
| 3208 - Patient |
| 3210 - Access Thread |
| 3212 - Distal Plug Cover |
| 3214 - Securement Stent |
| 3216 - Vessel Occluder |
| 3218 - Delivery Device Tip |
| 3220 - Delivery System |
| 3222 - Coil |
| 3224 - Stent |
| 3302A-3302C - Self-Expanding Baskets |
| 3304A - Fabric Layer |
| 3304B - Shape-Memory-Material Layer |
| 3306 - Atraumatic Distal Tip |
| 3316 - Vessel Occluder |
| 3402 - Shape-Memory-Material Skirt |
| 3404 - Shape-Memory-Material Wings |
| 3406 - Outer Balloon |
| 3408 - Inner Balloon |
| 3410 - Rough-Surfaced Balloon |
| 3412 - Distal Balloon Extension |
| 3414A-3414F - Ablation Devices |
| 3416 - Brush |
| 3418 - Cheese-Grater Agitator |
| 3602 - Polymer Balloon Layer |
| 3604 - Shape-Memory-Material Basket |
| 3606 - Fabric Balloon Layer |
| 3608 - Balloon Anchors |
| 3610A-3610D - Weeping Balloons |
| 3612A, 3612B - Anchoring Balloons |
| 3614 - Central Weeping Section |
| 3704 - Agitator |
| 3714 - Ablation Device |
| 3802 - Modular Rapid-Exchange Platform |
| 3804 - Agitator |
| 3806 - Rapid-Exchange Port |
| 3808 - Pullwire |
| 3810 - Balloon |
| 3814 - Ablation Device |
| 3902 - Fluid-Aspiration Port |
| 3904 - Fluid-Inflation Port |
| 3910 - Weeping Balloon |
| 3914 - Ablation Device |
| 4000 - Ablation System |
| 4002 - Catheter |
| 4006 - Syringe |
| 4010 - Balloon |
| 4014 - Ablation Device |
| 4016 - Elongated Tines |
| 4022 - Aperture |
| 4110 - Steerable Distal Catheter Portion |
| 4112 - Pullwire |
| 4114 - Ablation Device |
| 4210A, 4210B - Proximal and Distal Balloons |
| 4310 - Radially Eccentric Balloon |
| 4314 - Ablation Device |
| 4402 - Shape-Memory-Material Basket |
| 4410 - Self-Expanding Balloon |
| 4414 - Ablation Device |
| 4502 - Needle |

-continued

| COMPONENT INDEX |
| --- |
| 4514 - Ablation Device |
| 4600, 4602, 4604, 4606, and 4608 - Ablation-Technique Steps |

DETAILED DESCRIPTION

The present disclosure describes systems and techniques for treating vascular disorders, such as varicose veins. Some existing solutions include the use of highly complicated interventional devices (e.g., ablation catheters) that require excessive dexterity and training to operate effectively.

For instance, certain sclerotherapeutic catheters require the user (e.g., a clinician) to operate a first manual control (e.g., a syringe plunger) to infuse a chemical agent, such as a sclerosant, into a target vessel, while simultaneously operating a second, distinct manual control to longitudinally translate (e.g., distally advance and/or proximally withdraw) the catheter to disperse the chemical agent throughout the target vessel. In some such examples, the secondary control merely consists of the clinician manually pushing and/or pulling the catheter through the patient's vasculature. Needless to say, such systems are not widely regarded to be user-friendly.

Furthermore, some vascular treatment devices incorporate mechanical-based ablation devices in addition to, or instead of, chemical-based ablation. In many cases, mechanical ablation improves the effectiveness of the treatment, but exponentially complicates the operation of the device by not only incorporating yet another manual control to actuate a motion (e.g., rotation) of a mechanical agitator of the ablation device, but also requiring the clinician to consciously manage relative rates between all three aspects—i.e., a rate of longitudinal translation through the vessel, a rate of fluid infusion, and a rate of mechanical agitation.

In other words, many traditional sclerotherapy treatments require the clinician to manually infuse a "steady" flow of sclerosant, manipulate a separate control (e.g., squeeze a trigger) to actuate an abrasive element to mechanically disturb the vessel wall, and also simultaneously manually withdraw the catheter at a consistent rate. The required cognitive load and skill of the user to simultaneously accomplish all of these steps is high, leading to a greater likelihood of mismatching the amount of mechanical ablation performed and the amount of sclerosant delivered to the target treatment site. This not only creates a perception of a difficult-to-use device, but also may lead to inferior or incomplete venous ablation, e.g., if an insufficient amount of sclerosant is delivered.

A related limitation of the prior art is that many current injection methods do not isolate the sclerosant within the vessel being treated. Some patients may be sensitive to sclerosant, and if this fluid migrates or embolizes into undesired locations, complications can result. Additionally, if the sclerosant is not contained or isolated, a lesser volume may end up penetrating into the vessel wall, leading to reduced treatment efficacy.

FIG. 1 is a conceptual diagram of a vessel-ablation system 100, in accordance with one or more techniques of this disclosure. Ablation system 100 includes a catheter 102 and in some examples, but not all examples, an introducer sheath 104. Catheter 102 defines an elongated body 106 having a proximal portion 108 and a distal portion. Ablation system 100 further includes an ablation device 114 disposed at the distal portion 110 of elongated body 106, and a manual control device 112 (e.g., a handle) disposed at the proximal portion 108 of elongated body 106. In various examples herein, control device 112 and/or ablation device 114 may be integral components of catheter 102 (e.g., may be rigidly coupled to elongated body 106), or alternatively, may be removably coupled to catheter 102, as detailed further below with respect to FIG. 3.

As described above, control device 112, such as a proximal handle of catheter 102, includes one or more user controls configured to operate various aspects of ablation device 114. In particular, control device 112 includes at least one user control configured to simultaneously actuate at least two clinical functions of ablation device 114. For instance, a single user control of control device 112 may be configured to simultaneously actuate an agitator mechanism of ablation device 114 and infuse a chemical agent (e.g., a sclerosant) from ablation device 114. As another example, a single user control of control device 112 may be configured to simultaneously infuse a chemical agent from ablation device 114 and longitudinally translate (e.g., proximally withdraw and/or distally advance) ablation device 114 relative to control device 112. As another example, a single user control of control device 112 may be configured to simultaneously longitudinally translate ablation device 114 relative to control device 112 and actuate an agitator mechanism of ablation device 114. As another example, a single user control of control device 112 may be configured to simultaneously control all three of: an actuation of an agitator mechanism of ablation device 114, a longitudinal translation of ablation device 114, and infusion of a chemical agent from ablation device 114.

Figure 2:
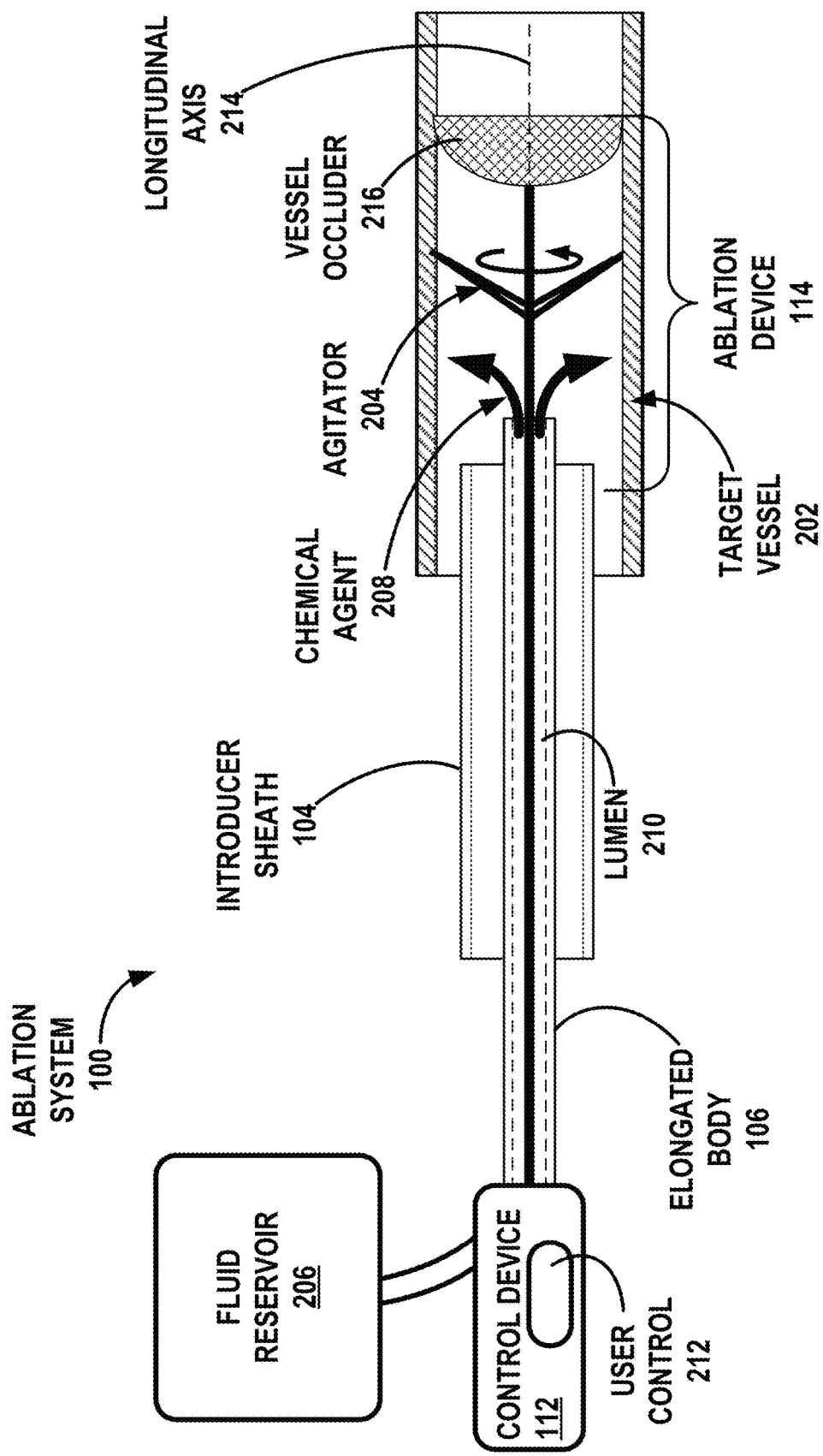
FIG. 2 is a conceptual diagram illustrating an application of an example of the ablation system of FIG. 1.

FIG. 2 is a conceptual diagram illustrating a non-limiting example application of ablation system 100 of FIG. 1. In particular, FIG. 2 illustrates ablation device 114 of FIG. 1 positioned within a target vessel 202, such as a varicose vein. As shown in FIG. 2, ablation device 114 includes a mechanical agitator 204, and means for infusing a chemical agent 208, such as a sclerosant, into target vessel 202. Ablation system 100 further includes vessel occluder 216 configured to reduce or prevent fluid flow through target vessel 202.

In the scenario illustrated in FIG. 2, a user (e.g., a clinician) of ablation system 100 has advanced ablation device 114 through introducer sheath 104 and into target vessel 202, such as a varicose vein, within a patient's vasculature. Once ablation device 114 is positioned at target vessel 202, the clinician may actuate user control 212, such as a button, thumbwheel, switch, toggle, lever, dial, trigger, plunger, or the like, integrated within control device 112. In accordance with techniques of this disclosure, user control 212 is configured to simultaneously govern at least two clinical functions of ablation system 100. For instance, actuation of user control 212 may be configured to automatically draw a predetermined volume (or predetermined flow rate) of a chemical agent 208 from a fluid reservoir 206, distally advance chemical agent 208 through an inner lumen 210 of elongated body 106, and release chemical agent 208 from ablation device 114 at the distal portion of elongated body 106 for infusion into target vessel 202.

Simultaneously, actuation of user control 212 may also be configured to trigger a preconfigured motion of mechanical agitator 204 of ablation device 114. In general, agitator 204 is configured to contact and disrupt an interior surface of target vessel 202. In the particular example of FIG. 2, agitator 204 includes a pair of elongated tines configured to mutually rotate about central longitudinal axis 214 of elongated body 106. Additionally or alternatively, actuation of user control 212 may be configured to simultaneously cause ablation device 114, including agitator 204, to longitudinally translate, e.g., proximally and/or distally parallel to central longitudinal axis 214, to engage agitator 204 across a greater portion of the interior wall of target vessel 202.

Figure 3:
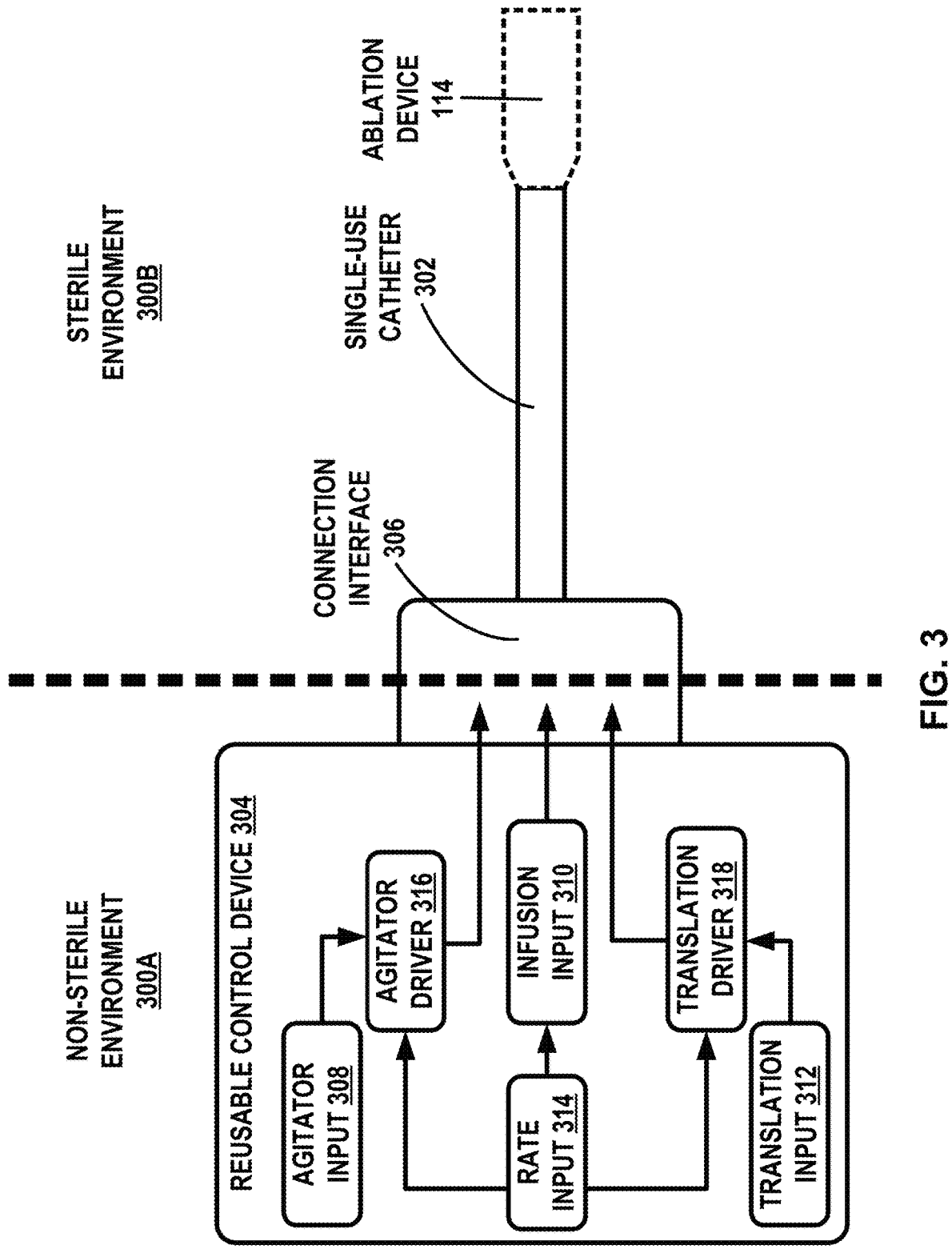
FIG. 3 is a conceptual diagram illustrating another example of the ablation system of FIG. 1.

FIG. 3 is a conceptual diagram illustrating another example of ablation system 100 of FIG. 1. As referenced above, FIG. 3 depicts an example in which a single-use (e.g., disposable) catheter 302 (e.g., catheter 102 of FIG. 1) is removably coupled to a reusable control device 304 (e.g., control device 112 of FIG. 1) via a connection interface 306. Such implementations provide for a number of benefits and practical applications. For instance, such implementations may be designed so as to reduce costs associated with both the manufacture and use of ablation system 100. As one example, reusable control device 304 may be operated from a non-sterile environment 300A, thereby reducing costs associated with sterilizing equipment after completion of the procedure. Similarly, although catheter 302 is intended to function within a sterile intraoperative environment 300B, since catheter 302 and ablation device 114 are designed to be postoperatively disposed, there is no obligation to postoperatively sterilize these components either.

In some example implementations of the system shown in FIG. 3, control device 304 may be configured to be reusable via separation of the fluid-infusion pathway (e.g., lumen 210) from the internal components of control device 304, as detailed further below with respect to FIGS. 4A-4C. Thus, control device 304 can be configured to be purchased separately from single-use catheter 302, which can decrease costs. For instance, because control device 304 (e.g., the handle) is reusable, additional design features that may otherwise have been cost-prohibitive can instead become viable to produce. However, because the single-use catheter 302 contacts at least a portion of the inside of control device 304, control device 304 should define a form-factor small enough to autoclave (e.g., heat-sterilize), as appropriate.

FIG. 3 further illustrates some example components of control device 304, any or all of which may be included within any of the examples of control device 112 described throughout this disclosure. As shown in FIG. 3, control device 304 includes at least three user controls (e.g., user control 212 of FIG. 2): an agitator input 308, a fluid-infusion input 310, and a longitudinal-translation input 312. However, it is to be understood that at least two of these three user controls may be operatively coupled to, or integrated within, a common user-input mechanism, such as a button, lever, knob, dial, switch, touchscreen, keypad, or the like.

As shown in FIG. 3, agitator input 308 is operatively coupled to an agitator driver 316, such as a motor or other suitable mechanism configured to drive the preconfigured motion of agitator 204 (FIG. 2). Similarly, longitudinal-translation input 312 is operatively coupled to a longitudinal-translation driver 318, configured to drive a longitudinal motion of ablation device 114 through target vessel 202. In some examples, but not all examples, agitator driver 316 and longitudinal-translation driver 318 may be the same component, or may share common sub-components, as detailed further below.

In the example of FIG. 3, control device 304 also includes a rate input 314 (e.g., user control 212 of FIG. 2) enabling the clinician to customize two or more functional rates or amounts associated with ablation device 114 relative to one another. For instance, rate input 314 may enable the clinician to select a particular infusion-flow-rate of chemical agent 208 (FIG. 2), relative to a longitudinal-translation-rate of ablation device 114 through target vessel 202, or relative to a preconfigured-motion (e.g., rotation, vibration, oscillation, etc.) rate of agitator 204. In this way, the clinician can more-conveniently and more-precisely control the operation of ablation system 100.

In one particular example, rate input 314 enables the clinician to select milliliters of chemical agent 208 per millimeters of longitudinal translation. For instance, this feed rate could be modified via different orifice sizes, e.g., using a Tuohy-Borst adaptor. Additionally or alternatively, various gear-ratios may be implemented to modify these rates. Additionally or alternatively, two tubes of different diameters and/or orifice diameters may be used—i.e., a "storage" tube feeding into an "active" tube.

Figure 4A:
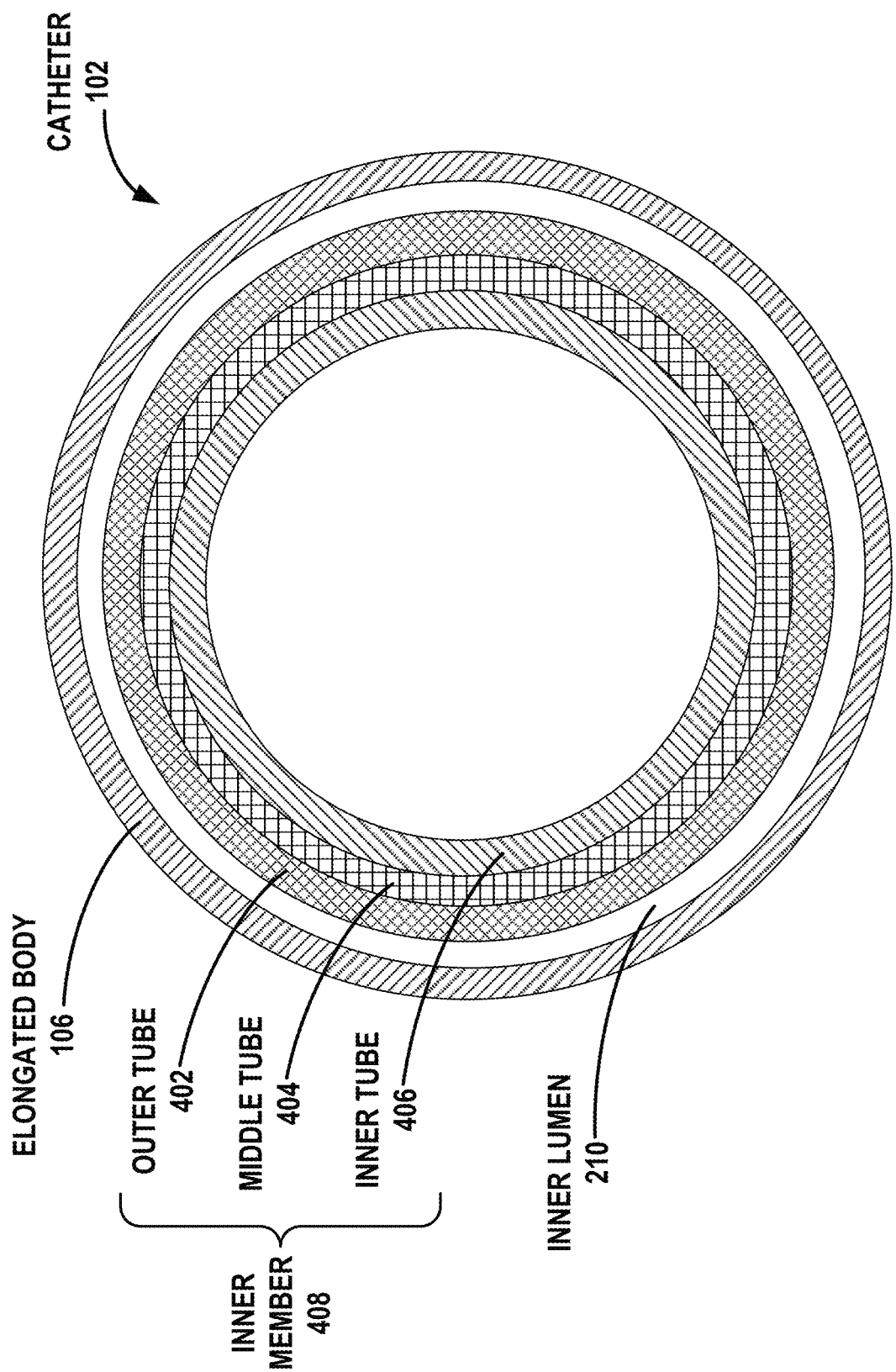
Figure 4B:
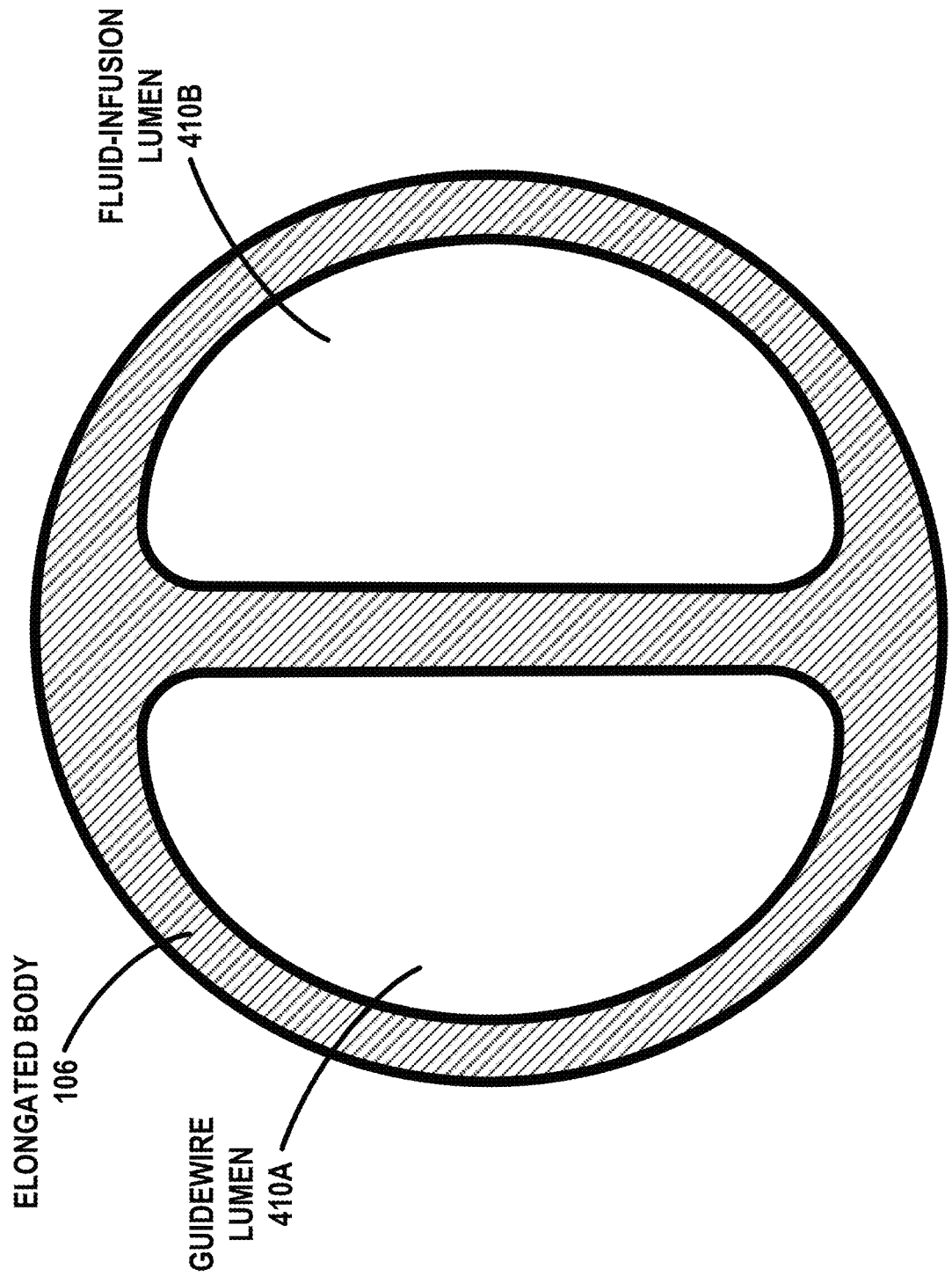

FIGS. 4A-4C are cross-sectional views through three respective examples of elongated body 106 of catheter 102 FIG. 1. In the example shown in FIG. 4A, catheter 102 includes both an outer elongated body 106 defining inner lumen 210, and an elongated inner tubular member 408 positioned within inner lumen 210. In some such examples, inner elongated member 408 can include a plurality of nested (e.g., coaxial) tubular layers: an outer tube 402, a middle tube 404, and an inner tube 406. That is, the elongated body 106 of the catheter 102 includes inner tube 406 disposed within an internal portion of the elongated body 106, middle tube 404 that substantially surrounds the inner tube 406, and an outer tube 402 that substantially surrounds the inner tube 406 and the middle tube 404. Any or all of tubes 402-406 may be formed from a polymer, such as a thermoplastic elastomer.

In one illustrative, non-limiting example, inner tube 406 is formed from etched polytetrafluoroethylene (PTFE), and middle tube 404 and outer tube 402 are formed from polyether block amide (e.g., Pebax™). Such materials may allow the elongated body 106 of the catheter 102 and the tubes 402-406 to be more lubricious to facilitate movement along a guidewire (not shown) positioned within inner lumen 210. Additionally, the thermoplastic, PTFE, and/or polyether block amide may result in improved flexibility and improved manufacturability of elongated body 106, as these materials facilitate mutual bonding between the various nested layers.

FIG. 4B illustrates an example of elongated body 106 defining two distinct (e.g., fluidically insulated) inner lumens: a guidewire lumen 410A and a fluid-infusion lumen 410B. Guidewire lumen 410A is configured to receive a guidewire (not shown) to help advance catheter 102 through the patient's vasculature toward the target vessel. Fluid-infusion lumen 410B is configured to distally transfer a chemical agent 208 (FIG. 2), such as a sclerosant, toward the target vessel 202. As referenced above with respect to FIG. 3, fluid-insulation of chemical agent 208 from other mechanical components of system 100 in this way (e.g., with distinct lumens) can help enable certain functions and other advantages, such as reusability of control device 304.

FIG. 4C illustrates another example of elongated body 106 having a third lumen, such as a fluid-aspiration lumen 410C, that is fluidically distinct from lumens 410A and 410B. For instance, fluid-aspiration lumen 410C may be configured to proximally transmit a fluid, such as a volume of the patient's blood, or a volume of previously infused sclerosant, away from the target vessel for withdrawal from the patient's vasculature. It is understood that the cross-sectional shapes of the lumens as shown are merely exemplary, and that additional lumens may be present in the system, up to and including as many lumens as can fit within elongated body 106 while still maintaining the usability of ablation system 100.

Figure 5:
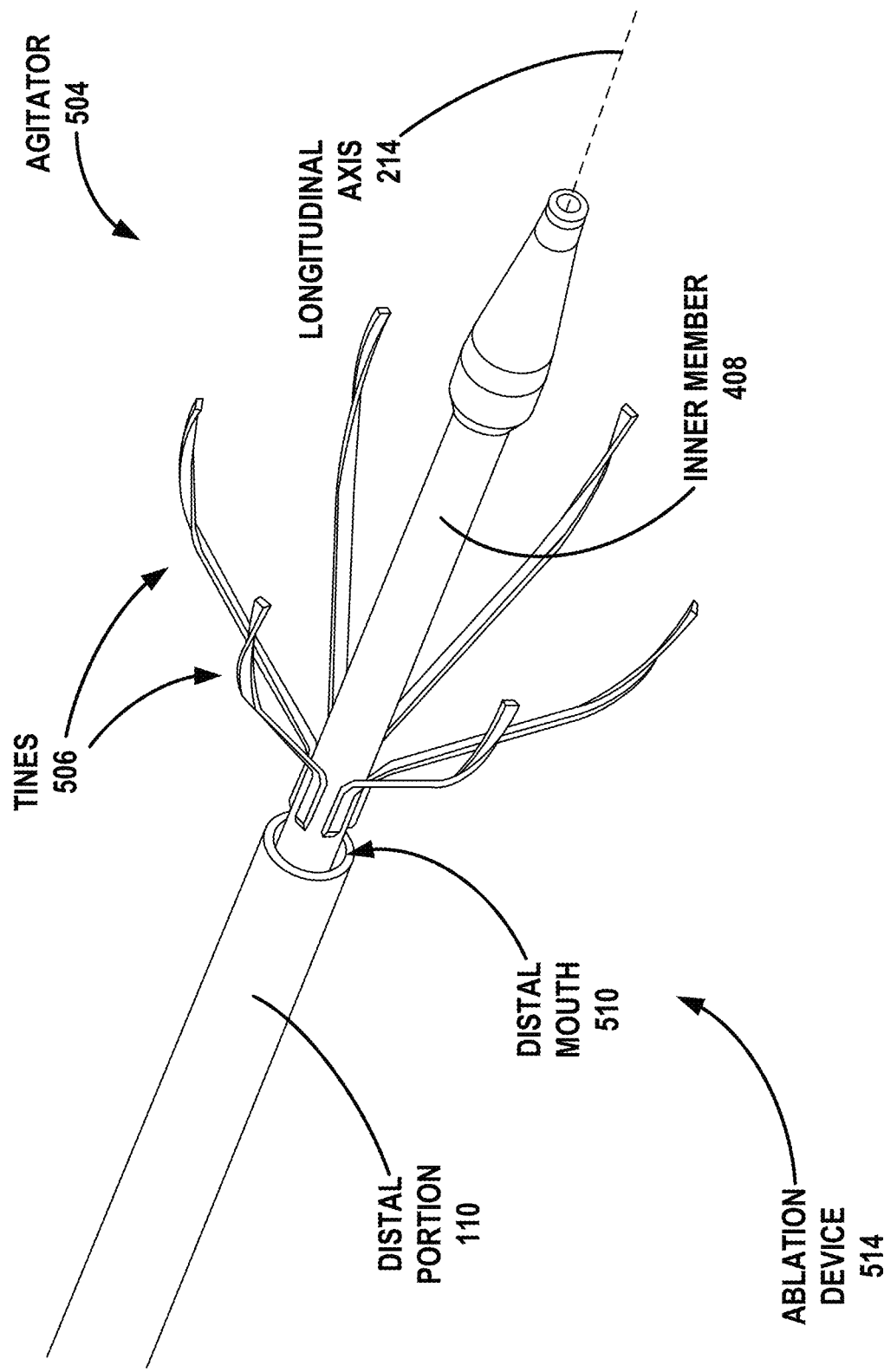
FIG. 5 is a profile view of an example of the ablation device of FIG. 1.

FIG. 5 is a profile view of an example ablation device 514 (e.g., ablation device 114 of FIG. 1) having a mechanical agitator 504 (e.g., agitator 204 of FIG. 2). Agitator 504 includes a plurality of elongated tines 506 distributed circumferentially around the distal portion 110 of elongated body 106. More specifically, elongated tines 506 are rigidly coupled to an outer surface of inner member 408. Inner member 408 and elongated tines are configured to extend longitudinally through inner lumen 210 of elongated body 106 and distally outward from distal catheter mouth 510.

Agitator 504 represents a "straight tine" agitator, in which elongated tines 506 extend generally parallel to central longitudinal axis 214. In some examples, agitator 504 is configured to rotate about longitudinal axis 214, causing tines 506 to disrupt or score the interior wall of the target vessel to improve absorption of chemical agent 208 (FIG. 2). Additionally or alternatively, agitator 504 may be configured to move according to other predetermined motions, such as oscillating longitudinally along longitudinal axis 214, vibrating, or a combination thereof. While agitator 504 is illustrated in FIG. 5 to include six elongated tines 506, it is understood that agitator 504 may include any suitable number of elongated tines 506. In the example shown in FIG. 5, a distal-most tip of each elongated tine is twisted relative to an internal axis of the respective tine, providing for an even-more-irregular surface for contacting and scoring the target vessel 202. In other examples, tines 506 can include sharp points or hooked blades to penetrate deeper into or through the target vessel 202.

Figure 6:
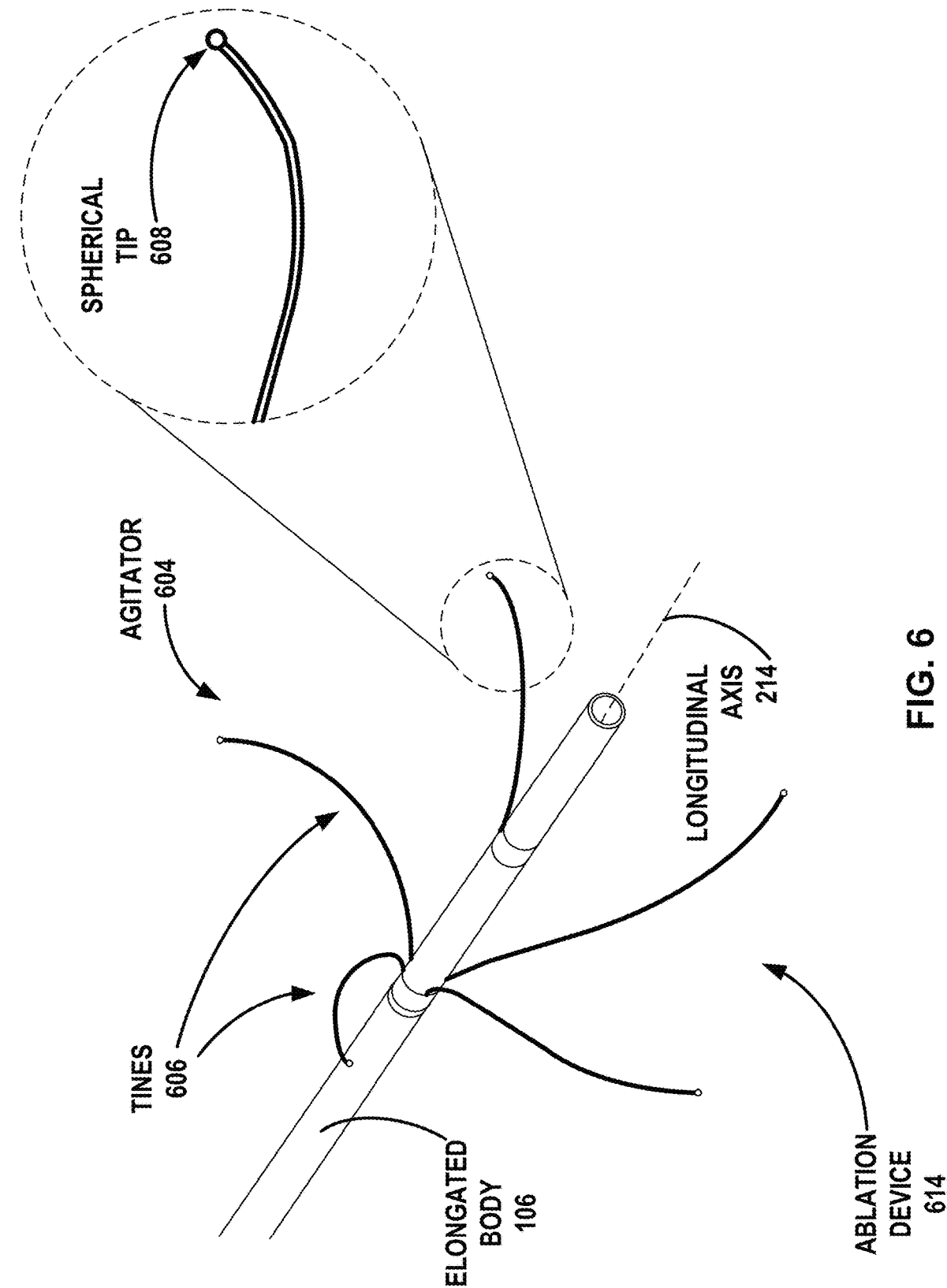
FIG. 6 is a profile view of an example of the ablation device of FIG. 1.

FIG. 6 is a profile view of ablation device 614 (e.g., ablation device 114 of FIG. 1) having an example agitator 604 (e.g., agitator 204 of FIG. 2) of ablation device 114 of FIG. 1. Agitator 604 includes a plurality of elongated tines 606 distributed circumferentially around, and rigidly coupled to, an exterior surface of the distal portion 110 (FIG. 1) of elongated body 106. Agitator 604 represents a "spiral tine" agitator, in which elongated tines 606 extend according to a spiral or helical configuration, both distally along longitudinal axis 214, and also circumferentially around longitudinal axis 214. Similar to agitator 504 of FIG. 5, agitator 604 of FIG. 6 may be configured to rotate, oscillate, vibrate, and/or move according to any suitable motion in order to contact and disrupt the interior wall of the target vessel.

While five elongated tines 606 are illustrated in FIG. 6, it is understood that agitator 604 may include any suitable number of elongated tines 606. As shown in the close-up view inset in FIG. 6, in some examples, but not all examples, a distal-most end of each elongated tine 606 may terminate with a spherical tip 608 configured to increase an applied pressure against the vessel wall via contact with the reduced surface area at any given point along the rounded surface of spherical tip 608.

Figure 7:
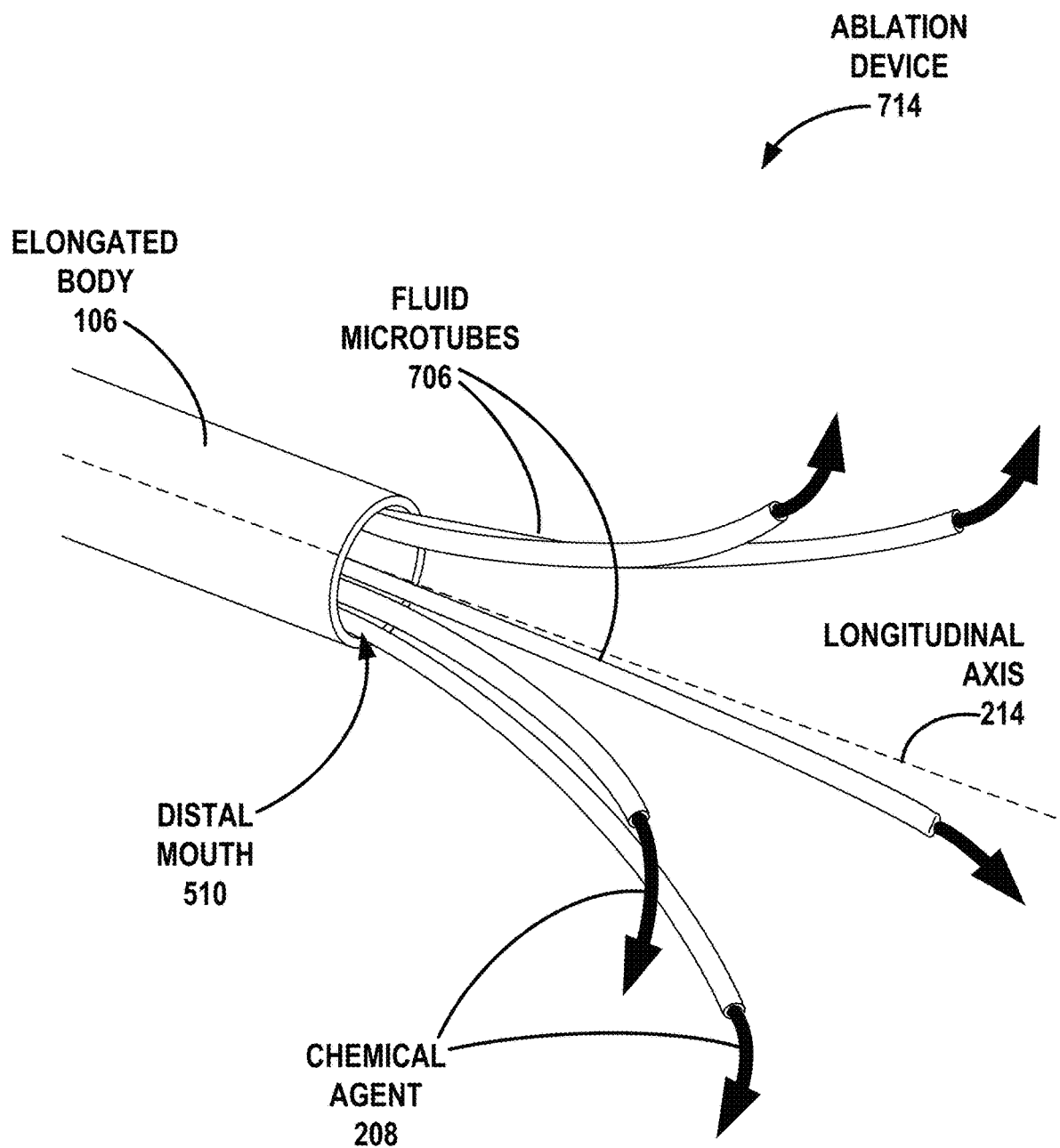
FIG. 7 is a profile view of an example of the ablation device of FIG. 1, including a plurality of fluid microtubes.

FIG. 7 is a profile view of an ablation device 714 (e.g., ablation device 114 of FIG. 1) having a plurality of fluid microtubes 706 configured to extend distally outward from distal catheter mouth 510. Fluid microtubes 706 are primarily configured to deliver chemical agent 208 (e.g., a sclerosant) into the target vessel 202 (FIG. 2). In some examples, but not all examples, fluid microtubes 706 may additionally be configured to perform similar functionality to elongated tines 506, 606 of FIGS. 5 and 6, respectively. That is, fluid microtubes 706 may be configured to rotate, oscillate, vibrate, or otherwise move relative to central longitudinal axis 214 in order to contact and disrupt the inner wall of target vessel 202.

Figure 8A:
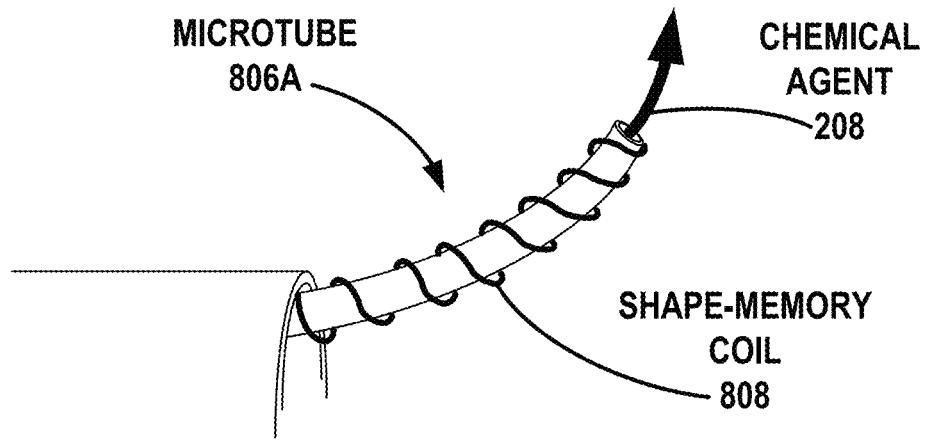
FIGS. 8A-8C are side views of three examples of the fluid microtubes of FIG. 7.
Figure 8B:
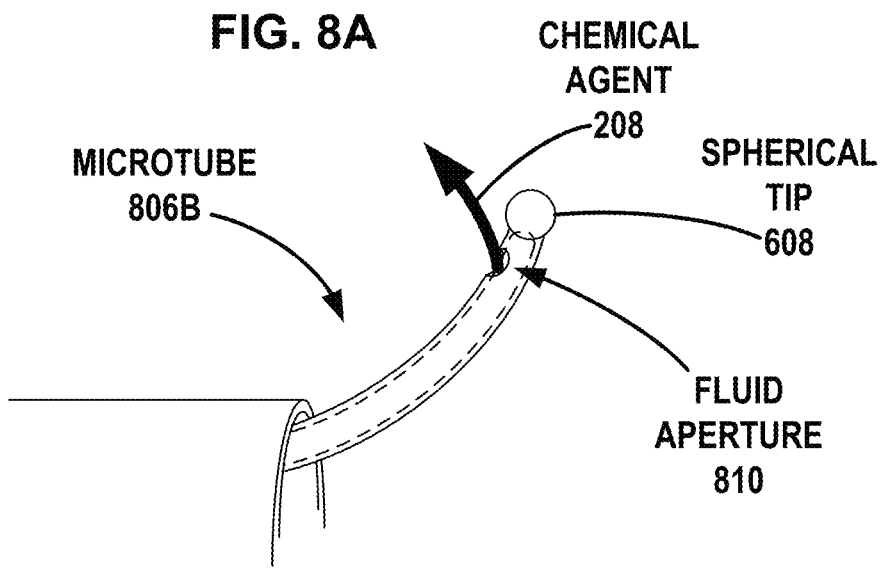
Figure 8C:
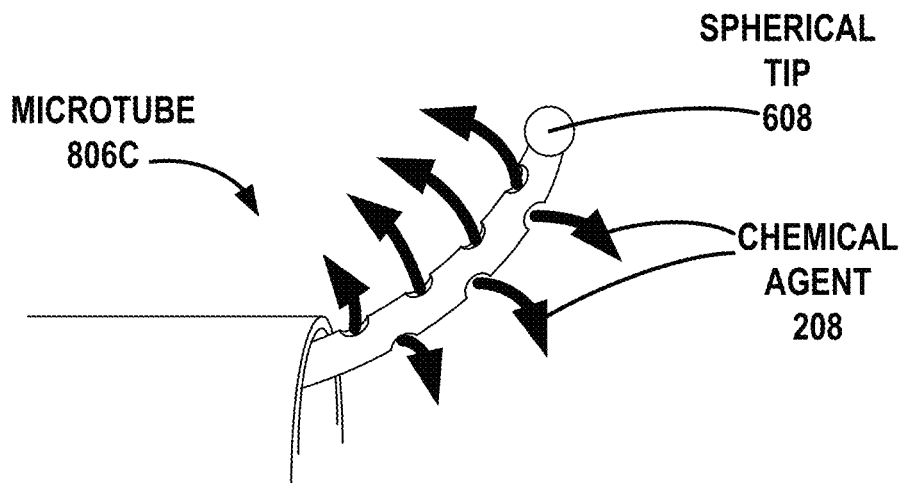

FIGS. 8A-8C are perspective views illustrating three non-limiting examples of one of fluid microtubes 706 of FIG. 7. For instance, FIG. 8A illustrates a shape-memory microtube 806A. Shape-memory microtube 806A may be formed from a shape-memory material (e.g., Nitinol), may be wrapped in a shape-memory-material coil 808, or both, such that fluid microtube 806A automatically conforms to a desired shape configuration for infusion of chemical agent 208.

FIG. 8B illustrates a fluid microtube 806B defining a single fluid aperture 810 configured to release chemical agent 208. In the example shown in FIG. 8B, fluid aperture 810 is disposed just proximal to spherical tip 608, although this position is not intended to be limiting. Similar to the example shown in FIG. 6, spherical distal tip 608 may be configured to contact and disrupt the inner wall of target vessel 202 (FIG. 2). By comparison, FIG. 8C illustrates a "porous" fluid microtube 806C defining a plurality of fluid apertures configured to release chemical agent 208.

In the example shown in FIG. 8B, fluid aperture 810 is disposed just proximal to spherical tip 608, although this position is not intended to be limiting. Similar to the example shown in FIG. 6, spherical distal tip 608 may be configured to contact and disrupt the inner wall of target vessel 202 (FIG. 2).

FIGS. 9A-9D illustrate a technique for using an example ablation device 914, which is an example of ablation device 114 of FIG. 1. Ablation device 914 includes a self-expanding agitator 904 (e.g., agitator 204 of FIG. 2) defining a plurality of elongated tines 906. As shown in FIGS. 9A-9D, tines 906 may be distal extensions of a common band or ring adhered to the exterior surface of elongated body 106.

Figure 9A:
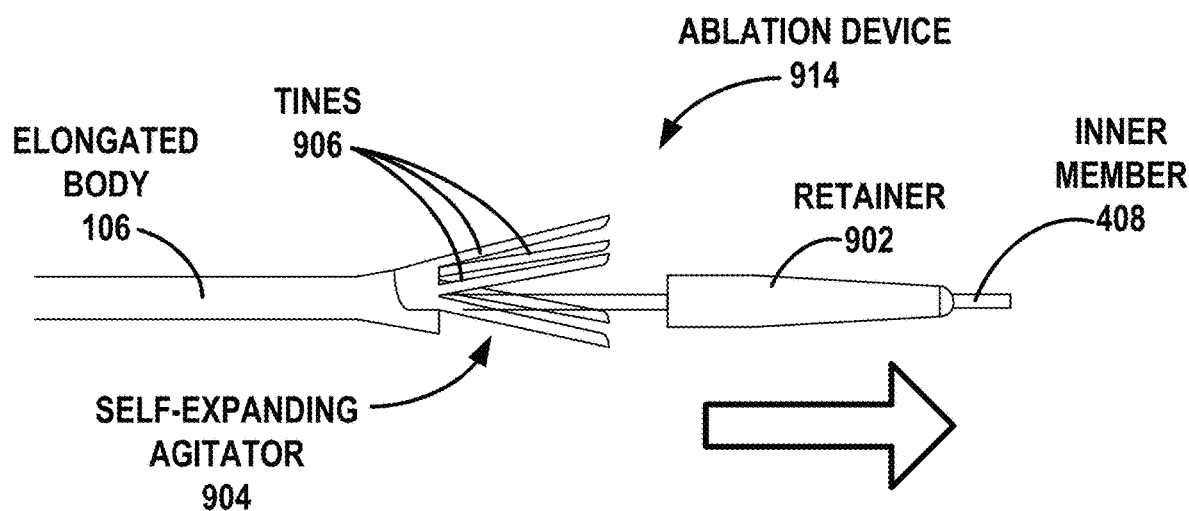
FIGS. 9A-9D illustrate a technique for using an example of the ablation device of FIG. 1 having a self-expanding mechanical agitator.

Prior to deployment, elongated tines 906 may be contained and compressed radially inward by a retainer element 902, which may be coupled to inner member 408 extending through inner lumen 210 of elongated body 106. As shown in FIG. 9A, inner member 408 and retainer 902 may be advanced distally (e.g., as indicated by the right-facing arrow) relative to agitator 904, releasing agitator 904 from inside retainer 902 and enabling tines 906 to deform radially outward into their predetermined deployed configurations.

Figure 9B:
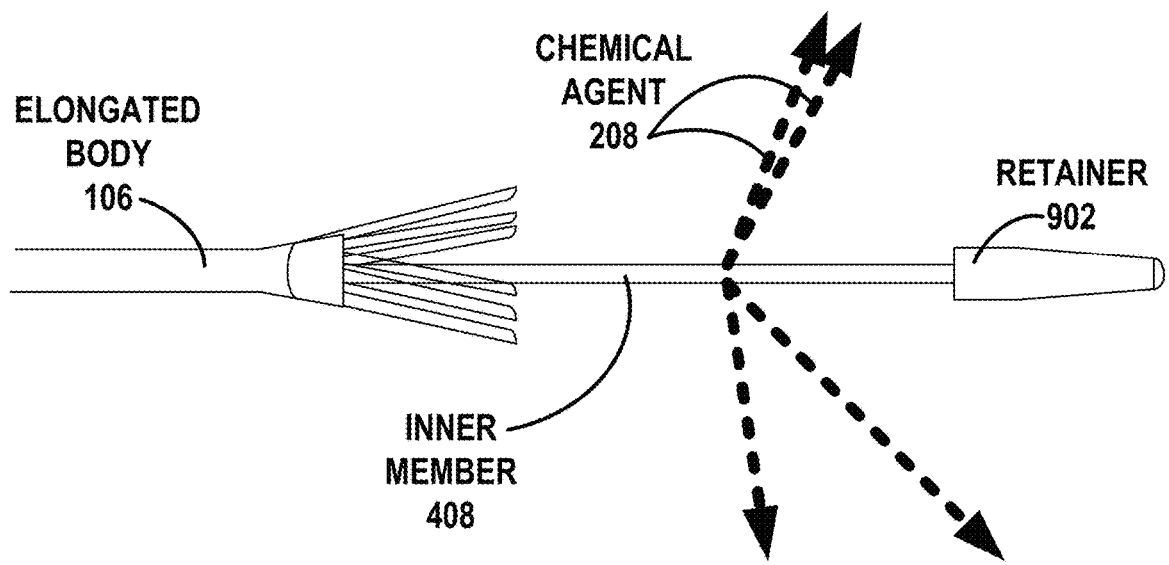
Figure 9C:
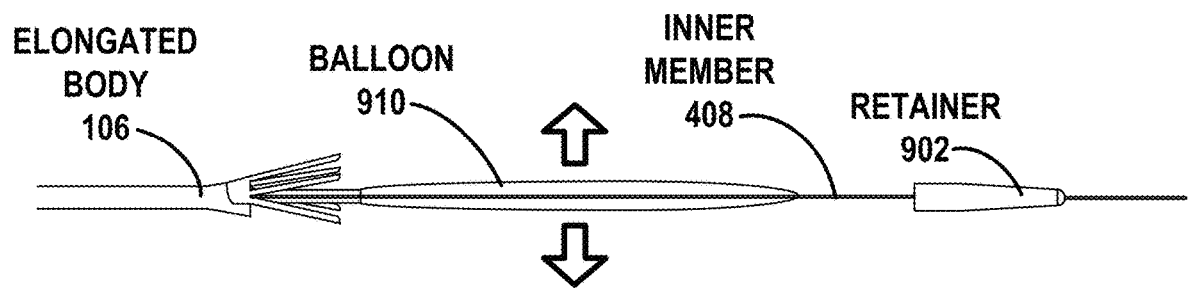
Figure 9D:
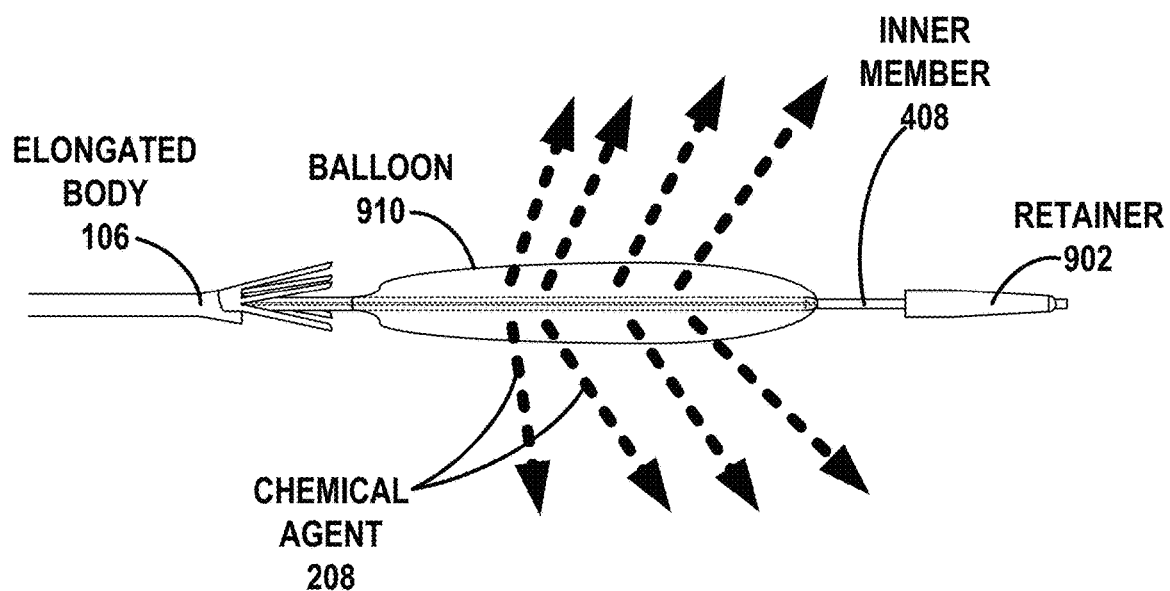

In some examples, such as the example shown in FIG. 9B, inner member 408 can take the form of a porous elongated inner member. In such examples, the clinician can actuate one of user controls 212 (FIG. 2) to release and infuse chemical agent 208 from inner member 408. Additionally or alternatively, as shown in FIGS. 9C and 9D, ablation device 114 can include a porous or "weeping" interventional balloon 910. In such examples, the clinician can actuate one of user controls 212 to at least partially inflate balloon 910 with chemical agent 208 (FIG. 9C), where the chemical agent 208 can then infuse outward through the surface of balloon 910 (FIG. 9D).

Figure 10:
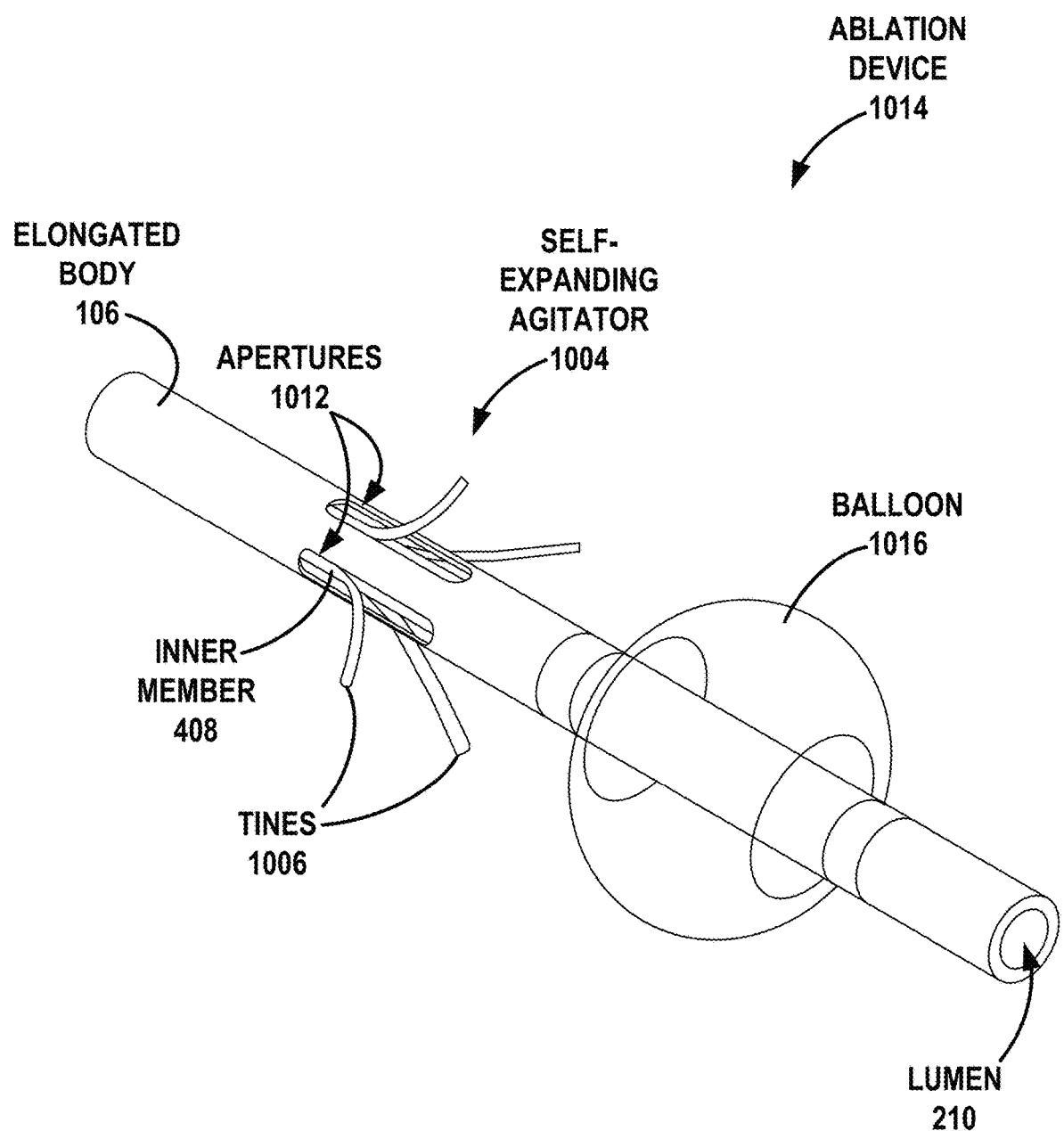
FIG. 10 illustrates an example ablation device of the ablation system of FIG. 1 having another self-expanding mechanical agitator.

FIG. 10 is a profile view of another example ablation device 1014 (e.g., ablation device 114 of FIG. 1) having a self-expanding agitator 1004 (e.g., agitator 904 of FIGS. 9A-9D) having a plurality of elongated tines 1006. Unlike tines 906 of FIGS. 9A-9D, which are coupled to an exterior surface of elongated body 106, tines 1006 of FIG. 10 are coupled to inner member 408 positioned within inner lumen 210. During use, the clinician may actuate one of use controls 212 (FIG. 2) to advance inner member 408 distally through inner lumen 210 until tines 1006 self-expand radially outward through respective apertures 1012 defined by elongated body 106.

Figure 11:
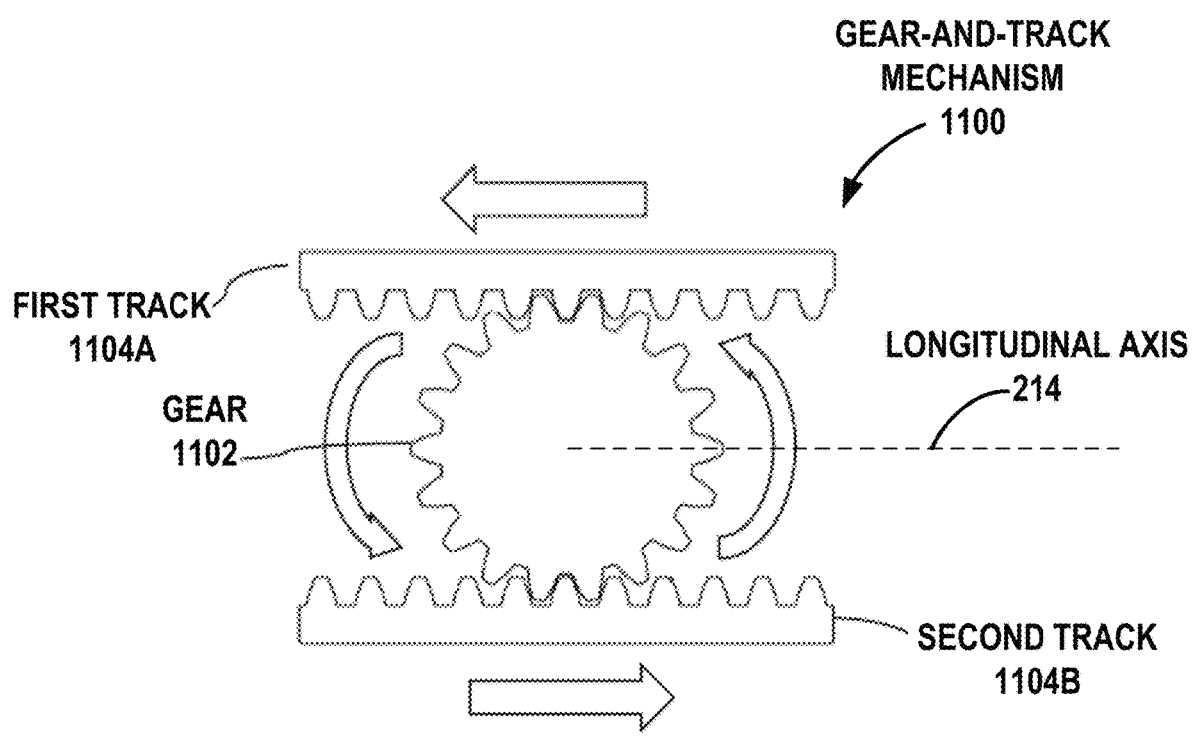
FIG. 11 is a conceptual diagram illustrating an example gear-and-track mechanism of the ablation system of FIG. 1.

FIG. 11 illustrates a gear-and-track mechanism 1100 for ablation system 100 of FIG. 1. Gear-and-track mechanism 1100 may be an example of translation driver 318 of FIG. 3. That is, the gear-and-track mechanism 1100 is configured to at least move ablation device 114 (FIG. 1) longitudinally (e.g., proximally and/or distally) relative to control device 112 in response to user-actuation of translation input 312 (FIG. 3). For instance, although not shown in FIG. 11, linear-translation input 312 of FIG. 3, such as a thumbwheel or the like, may be operatively coupled to wheel gear 1102, which, in turn, is operatively coupled to first track 1104A and second track 1104B. First track 1104A and second track 1104B may be positioned on opposite sides (e.g., top and bottom, from the perspective shown in FIG. 11) of wheel gear 1102, such that, when wheel gear 1102 rotates (e.g., in response to actuation of translation input 312), first track 1104A and second track 1104B move longitudinally in opposing directions. In response, ablation device 114 (FIG. 1), which is rigidly coupled to either first track 1104A or second track 1104B, moves longitudinally parallel to central longitudinal axis 214.

Figure 12A:
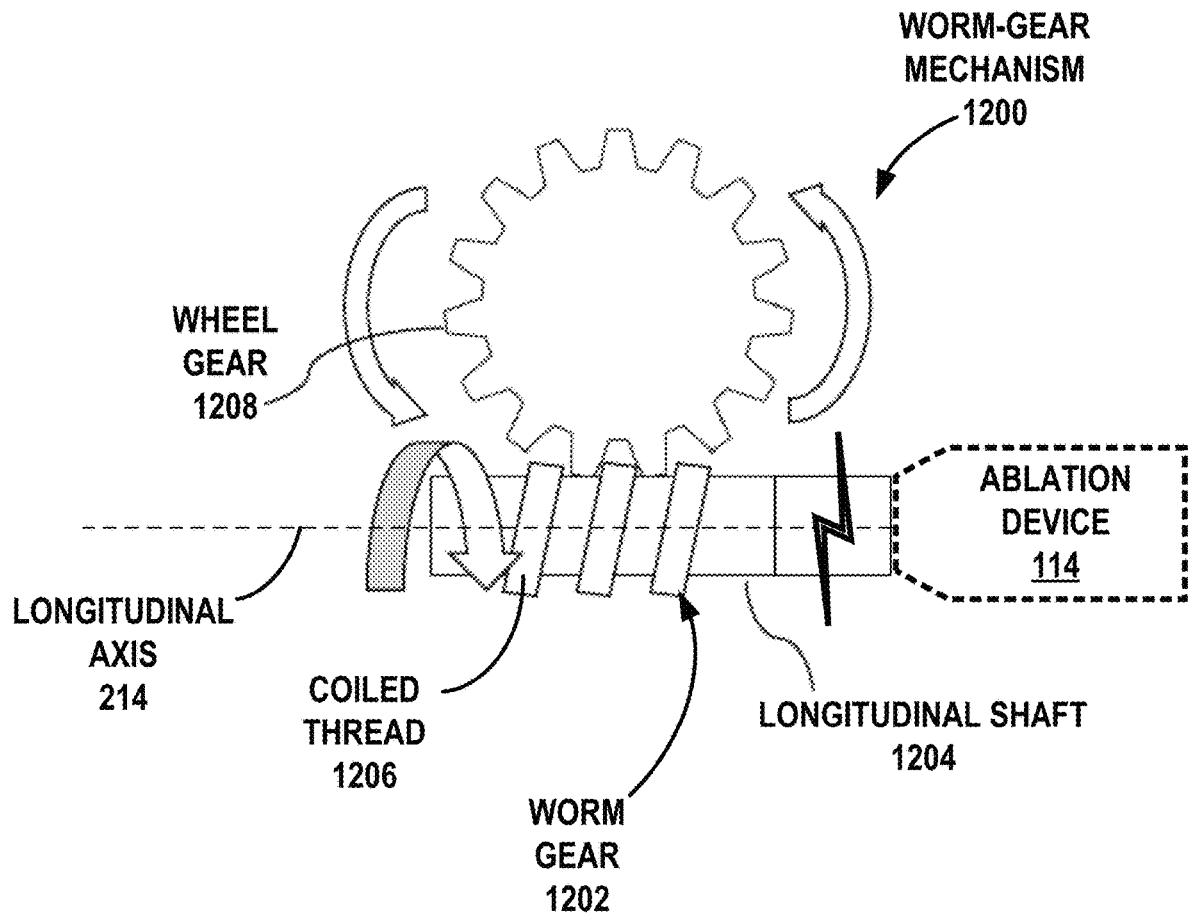
FIGS. 12A and 12B are conceptual diagrams illustrating an example worm-gear mechanism of the ablation system of FIG. 1.
Figure 12B:
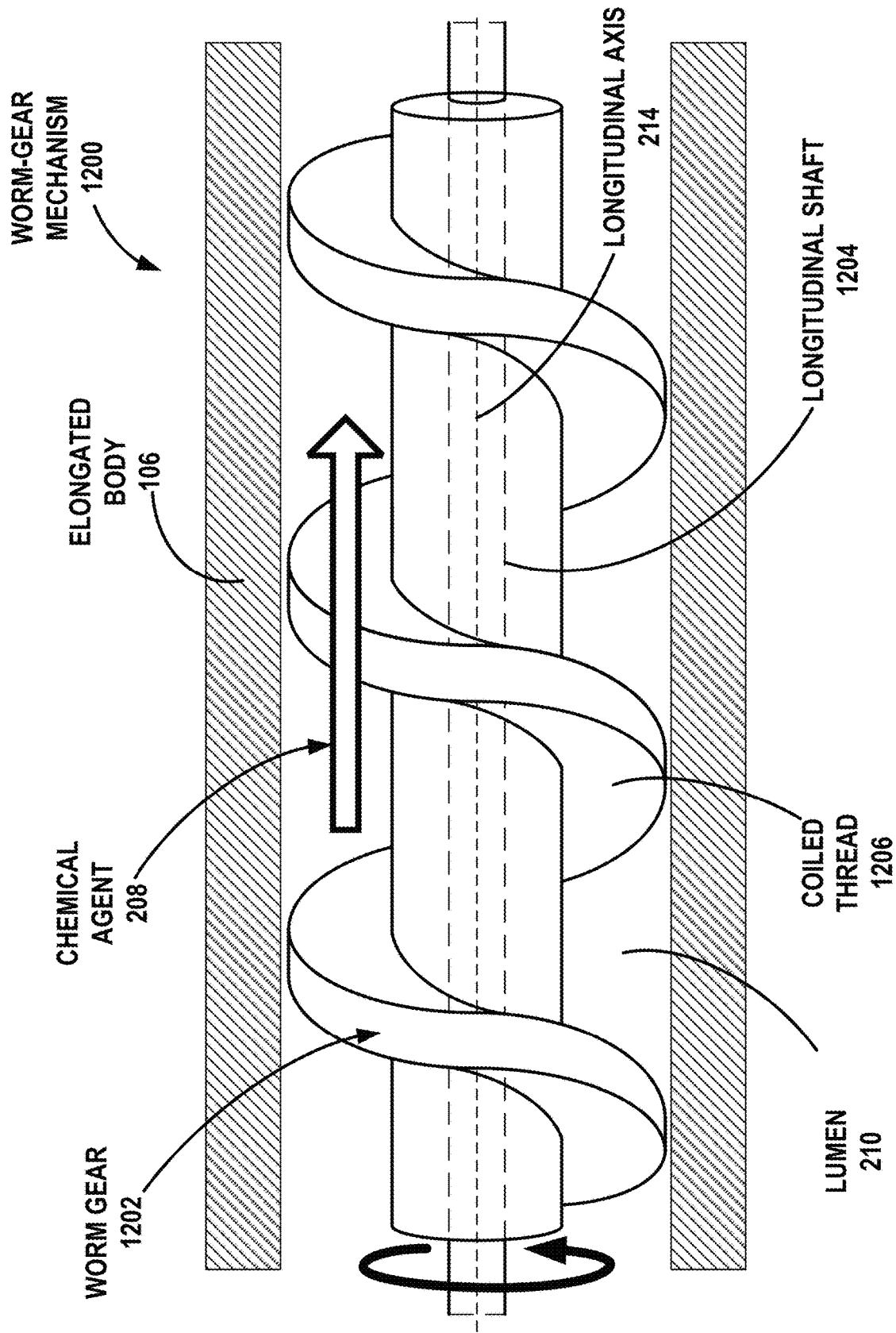

FIGS. 12A and 12B illustrate a worm-gear mechanism 1200, in which a wheel gear 1208, which may be a thumbwheel, or may be rigidly coupled to a thumbwheel (e.g., user control 212 of FIG. 2) is operatively engaged with a worm gear 1202. Worm gear 1202 includes a longitudinal shaft 1204, and a coiled thread 1206 extending both longitudinally along and circumferentially around longitudinal shaft 1204. Longitudinal shaft 1204 is an example of inner elongated member 408 of FIG. 4, e.g., is configured to fit within inner lumen 210 of elongated body 106.

As shown in FIG. 12A, ablation device 114 may be rigidly coupled to a distal portion of longitudinal shaft 1204, such that rotation of wheel gear 1208 (e.g., in response to user-actuation of translation input 312 of FIG. 3), ablation device 114 moves proximally and/or distally along longitudinal axis 214.

In some examples, the configuration of wheel gear 1208 relative to worm gear 1202 can enable worm gear 1202 to simultaneously translate along longitudinal axis 214 and rotate about longitudinal axis 214. Accordingly, for examples in which ablation device 114 includes a rotational agitator 204 (e.g., FIG. 2), a single user control 212 (FIG. 2) can be configured to actuate both longitudinal translation and rotation of agitator 204. In fact, worm gear 1202 can be configured to simultaneously enable any, or even all three of, the ablative functions described above, including longitudinal translation of agitator 204, rotation of agitator 204, and infusion of chemical agent 208. For instance, as illustrated in FIG. 12B, coiled thread 1206 can be fluidically sealed against an interior surface of the inner lumen 210 such that worm gear 1202 functions as an Archimedes screw, configured to pump chemical agent 208 distally along longitudinal axis 214 as longitudinal shaft 1204 rotates about longitudinal axis 214. According to similar principles, the rotational direction of worm gear 1202 may be inverted so as to proximally aspirate a fluid, such as previously infused sclerosant, or a volume of the patient's blood, away from target vessel 202.

According to the configuration shown in FIG. 12B, a fluid volume of chemical agent 208 delivered to the target vessel is directly correlated with the number of rotations of the mechanical agitator 204 (FIG. 2), eliminating the need for the clinician to consciously calibrate and manually maintain the relative rates between these two variables during the ablation treatment. In some examples, the fluid volume (or flow rate) of chemical agent 208 delivered to the target vessel can be increased by increasing the "head pressure" of chemical agent 208, e.g., near the proximal portion 108 of catheter 102 (FIG. 1). The clinician can adjust this head pressure, for example, by adjusting the height of fluid reservoir 206 (FIG. 2), e.g., a sclerosant-solution bag, above the patient. For instance, the clinician may adjust the height of fluid reservoir 206 by a distance proportional to the inner diameter (or cross-sectional area) of target vessel 202, thereby customizing the total delivered fluid volume (or fluid flow-rate, as appropriate) to more-effectively treat the target vessel. Such adjustments may be performed automatically, e.g., by a machine configured to precisely adjust reservoir height based on vessel-diameter sensor data or user-input values, or alternatively, may be performed manually by the clinician's team upon consulting a lookup table (or the equivalent) indicating predetermined relationship(s) between fluid-reservoir height and vessel diameter.

According to the techniques of this disclosure, additional or alternative forms of autoregulation may be present for fluid infusion. For instance, mechanical elements of ablation device 114 (e.g., agitator 204) may be expanded to accommodate a larger-diameter target vessel 202, which may require a commensurate radial expansion of distal catheter mouth 510. As distal catheter mouth 510 expands, the fluid-resistance against a flow of chemical agent 208 decreases, thereby increasing the volume of chemical agent 208 delivered to the target vessel (assuming constant head pressure). In this way, ablation system 100 may be configured to automatically "calibrate" the volume (or flow rate) of infused chemical agent 208, and the "amount" of mechanical agitation (e.g., number and/or rate of agitator rotations), as a function of vessel size, i.e., providing more sclerosant and agitation to larger-diameter vessels, and less sclerosant and agitation to smaller-diameter vessels. In some such examples, the need for ultrasonic imaging (or the equivalent) to indicate the relative position of ablation device 114 and/or the delivered volume of chemical agent 208 may be significantly reduced, or even eliminated.

As another example of the autoregulation of ablation system 100, various examples described herein include porous weeping balloons (e.g., balloon 910 of FIGS. 9C and 9D). The weeping balloons can be designed to be "oversized" such that they remain wrapped, folded, or pleated within smaller-diameter vessels. These folds and pleats will mutually seal many of the fluid micropores against each other, thereby reducing the amount and/or rate of chemical agent 208 weeping through the balloon. For larger-diameters vessels, the balloon may expand further, exposing more of the micropores and allowing a larger amount of chemical agent 208 to weep through thereby more-effectively treating target vessel 202.

The examples shown in FIGS. 11-12B are intended to illustrate high-level concepts, and are not intended to be limiting. For instance, other examples may include additional gears configured to provide space between adjacent components and/or to enable control over the resulting gear ratios, such that the linear translation, fluid infusion, and mechanical agitation can be precisely customized by the user to accommodate the unique clinical parameters presented.

Figure 13A:
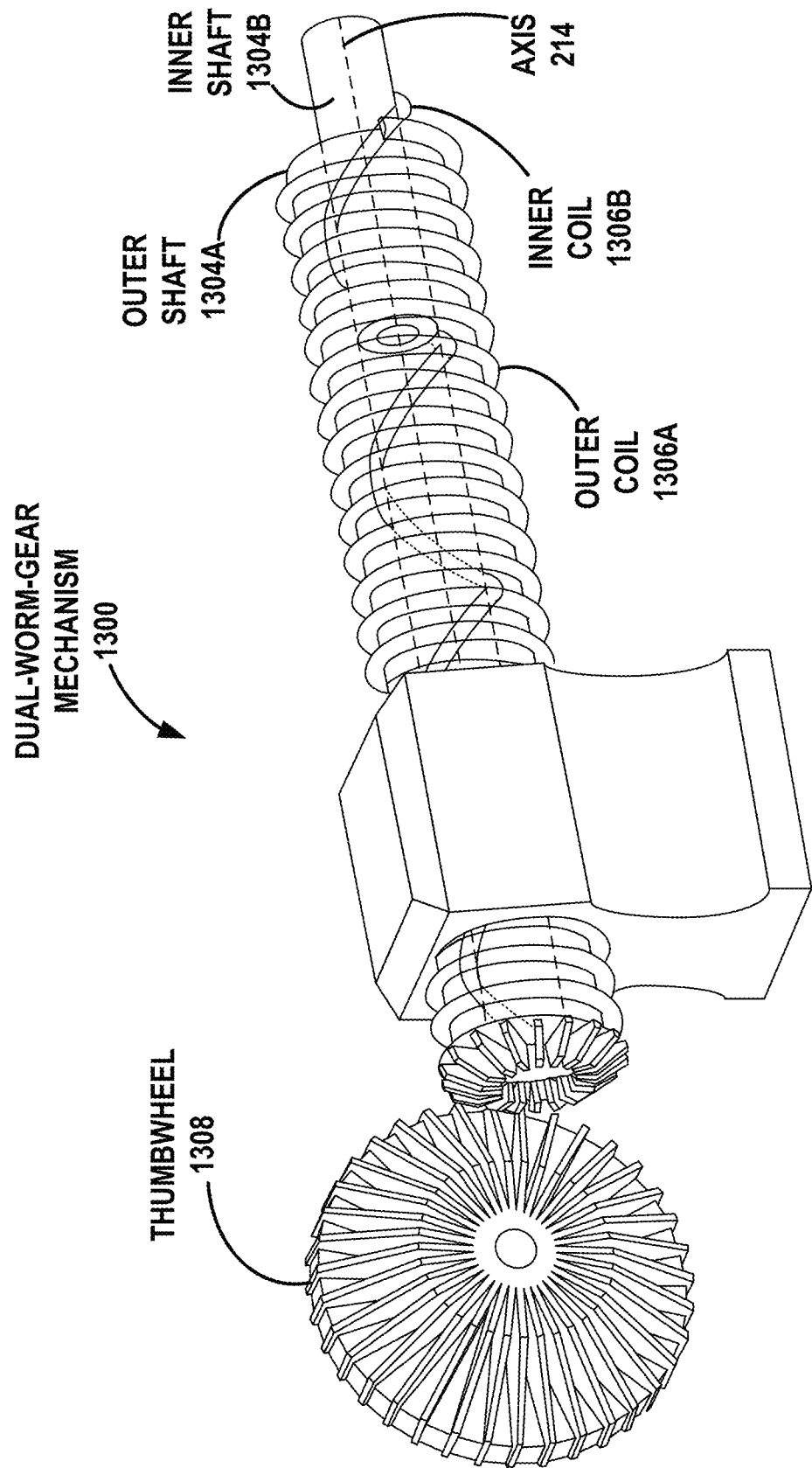
FIGS. 13A-13C depict an example dual-coaxial-worm-gear mechanism for the ablation system of FIG. 1.
Figure 13B:
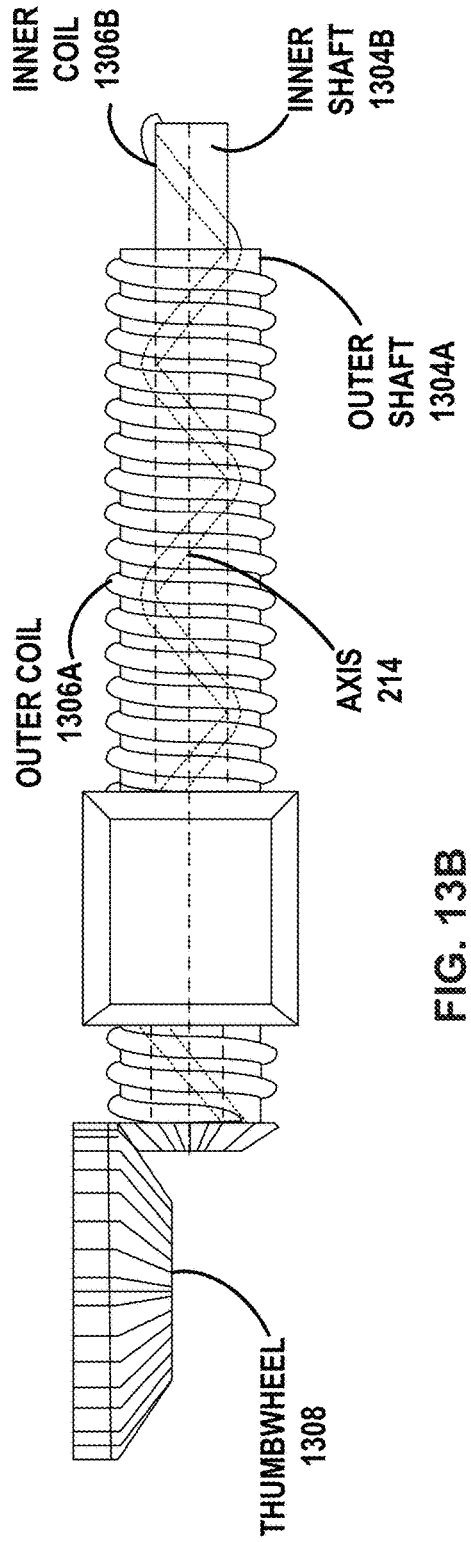
Figure 13C:
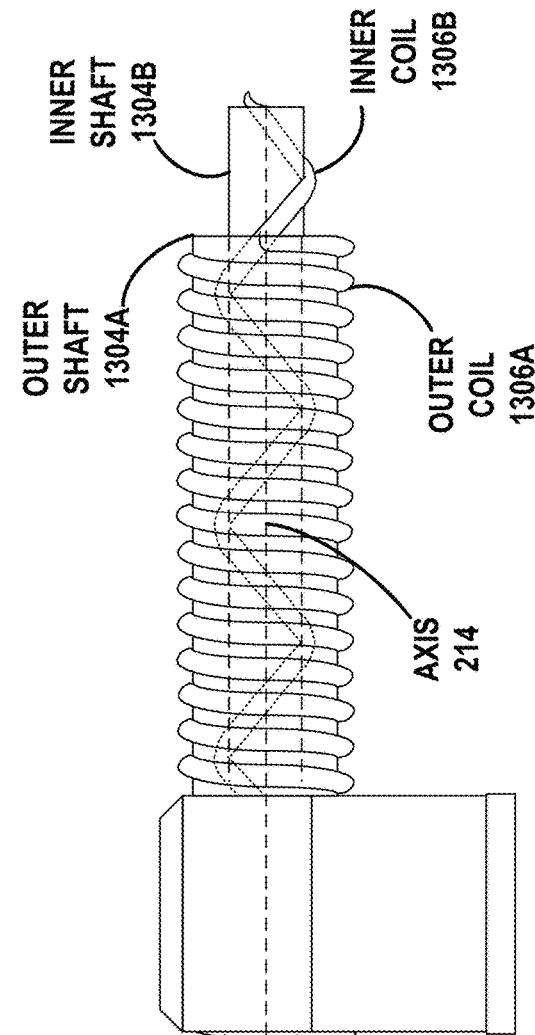

FIGS. 13A-13C depict an example dual-worm-gear mechanism 1300 for the ablation system of FIG. 1. Dual-worm-gear mechanism 1300 is an example of worm-gear mechanism 1200 of FIGS. 12A and 12B, except for the differences noted herein. For instance, dual-worm-gear mechanism 1300 may be used to infuse chemical agent 208 using similar principles (e.g., Archimedes screw pumps) as described above with respect to FIG. 12B.

As shown in FIGS. 13A-13C, dual-coaxial-worm-gear mechanism 1300 includes a thumbwheel 1308 (e.g., user control 212 of FIG. 2, and fluid-infusion input 310 and translation input 312 of FIG. 3) operatively engaged with a dual coaxial worm gear 1302. Dual coaxial worm gear 1302 includes an outer longitudinal shaft 1304A; an outer coiled thread 1306A extending both longitudinally along and circumferentially around outer longitudinal shaft 1304A; an inner longitudinal shaft 1304B disposed within an inner lumen of outer longitudinal shaft 1304A; and an inner coiled thread 1306B extending both longitudinally along and circumferentially around inner longitudinal shaft 1304B. Longitudinal shafts 1304A, 1304B are both examples of inner elongated member 408 of FIG. 4, e.g., are configured to fit within inner lumen 210 of elongated body 106.

In a first example, a mechanical interaction between rotating thumbwheel 1308 and outer coiled thread 1306A drives a longitudinal (e.g., distal) motion of a syringe plunger (not shown), thereby infusing chemical agent 208 into the target vessel. Simultaneously, the mechanical interaction between rotating thumbwheel 1308 and inner coiled thread 1306B drives a longitudinal (e.g., proximal) motion of ablation device 114, thereby longitudinally translating mechanical agitator 204 across the inner wall of target vessel 202.

In a second example, a mechanical interaction between rotating thumb wheel 1308 and outer coiled thread 1306A drives a longitudinal (e.g., proximal) motion of ablation device 114, thereby linearly translating mechanical agitator 204 across the inner wall of the target vessel. Simultaneously, the mechanical interaction between rotating thumbwheel 1308 and inner coiled thread 1306B drives a longitudinal (e.g., distal) motion of a syringe plunger (not shown), thereby infusing chemical agent 208 into the target vessel.

In either example, the relative speeds of the two longitudinal motions are determined by the pitch ratio between outer coiled thread 1306A and inner coiled thread 1306B. For instance, in the example illustrated in FIGS. 13A-13C, outer coiled thread 1306A has a much "tighter" configuration than inner coiled thread 1306B, in that adjacent turns of outer coiled threads 1306A are significantly closer together than adjacent turns of inner coiled threads 1306B. Accordingly, when outer longitudinal shaft 1304A and inner longitudinal shaft 1304B simultaneously rotate about longitudinal axis 214, inner longitudinal shaft 1304B (and any components rigidly coupled to it) travels a significantly longer distance along longitudinal axis 214 than outer shaft 1304A does.

Additionally or alternatively, dual-worm-gear mechanism 1300 may be configured to provide a rotational motion of ablation device 114, thereby enabling precise user control over all three functions of longitudinal translation, agitator rotation, and fluid infusion via a single user-input mechanism, i.e., thumbwheel 1308.

Figure 14:
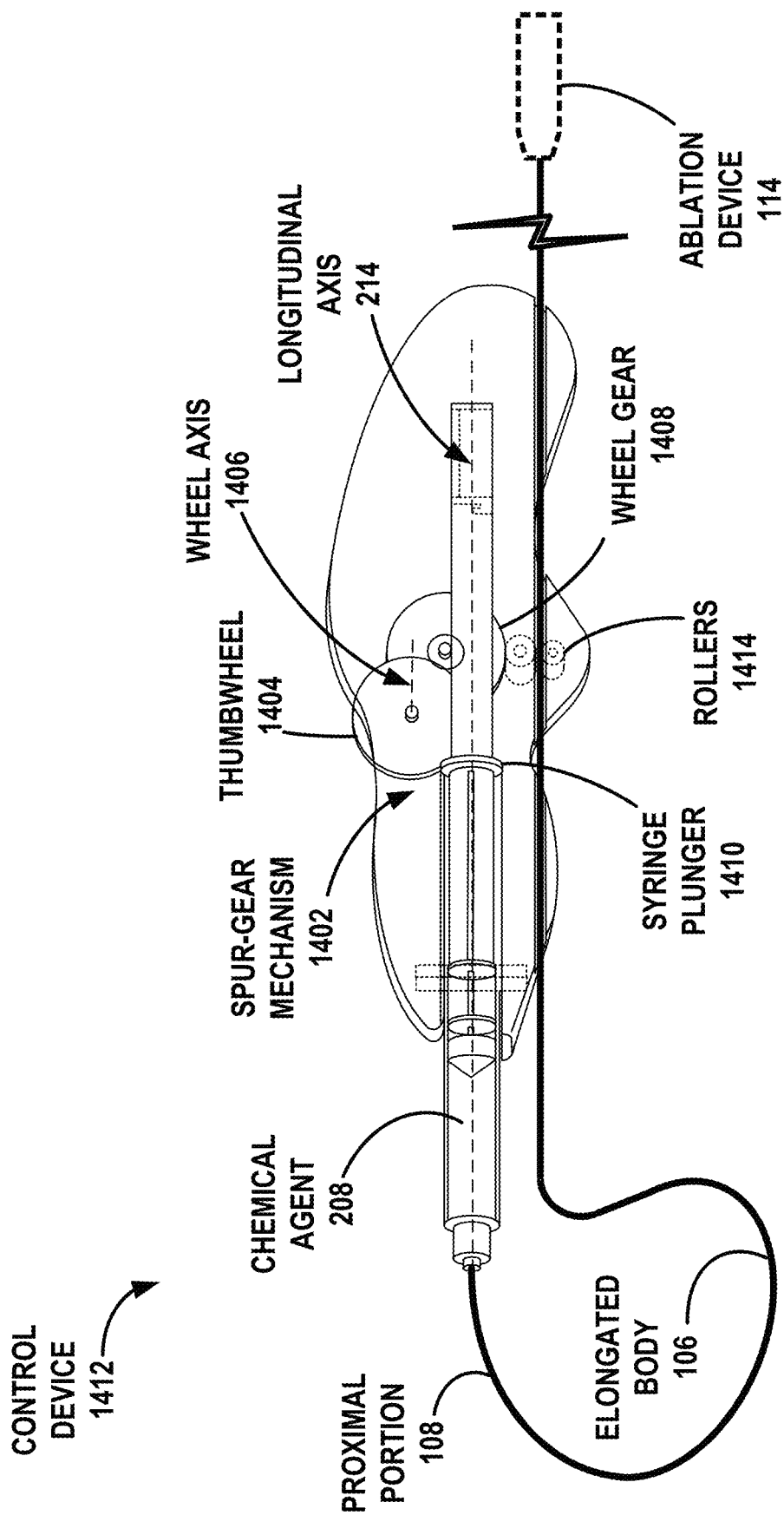
FIG. 14 is a transparent perspective view of an example of the control device of FIG. 1 having an integrated forward-spur-gear mechanism.

FIG. 14 is a transparent perspective view of a manual control device 1412 (e.g., proximal control device 112 of FIG. 1) having an integrated spur-gear mechanism 1402. As used herein, a "spur gear" refers to a gearwheel with teeth defining both a radial length extending radially outward from the gear's rotational axis, and an axial length extending parallel to the gear's rotational axis.

In the example of FIG. 14, control device 1412 includes a thumbwheel 1404 (e.g., user control 212 of FIG. 2, fluid-infusion input 310, and translation input of 312 of FIG. 3) enabling the clinician to simultaneously infuse chemical agent 208 and longitudinally translate ablation device 114 (e.g., agitator 204). Thumbwheel 1404 is user-rotatable about a wheel axis 1406 perpendicular to central longitudinal axis 214, and is operatively engaged with both syringe plunger 1410 and wheel gear 1408.

From the perspective of FIG. 14, a clockwise rotation of thumbwheel 1404 drives syringe plunger 1410 to the left, thereby infusing chemical agent 208 into the inner lumen 210 (FIG. 2) of elongated body 106.

Additionally, elongated body 106 is friction-pinched between a pair of catheter rollers 1414 engaged with wheel gear 1408, such that the same clockwise rotation of thumbwheel 1404 drives elongated body 106 to the left, thereby retracting ablation device 114 proximally through target vessel 202 (FIG. 2).

In other examples, control device 1412 can include any suitable number of interlocking gears, enabling the user to modify (e.g., customize) the relative relationships between rotational motion of thumbwheel 1404, longitudinal motion (e.g., proximal retraction) of ablation device 114, and/or longitudinal motion (e.g., distal advancement) of syringe plunger 1410 (e.g., fluid-infusion flowrate) to accommodate the unique clinical needs presented.

Figure 15:
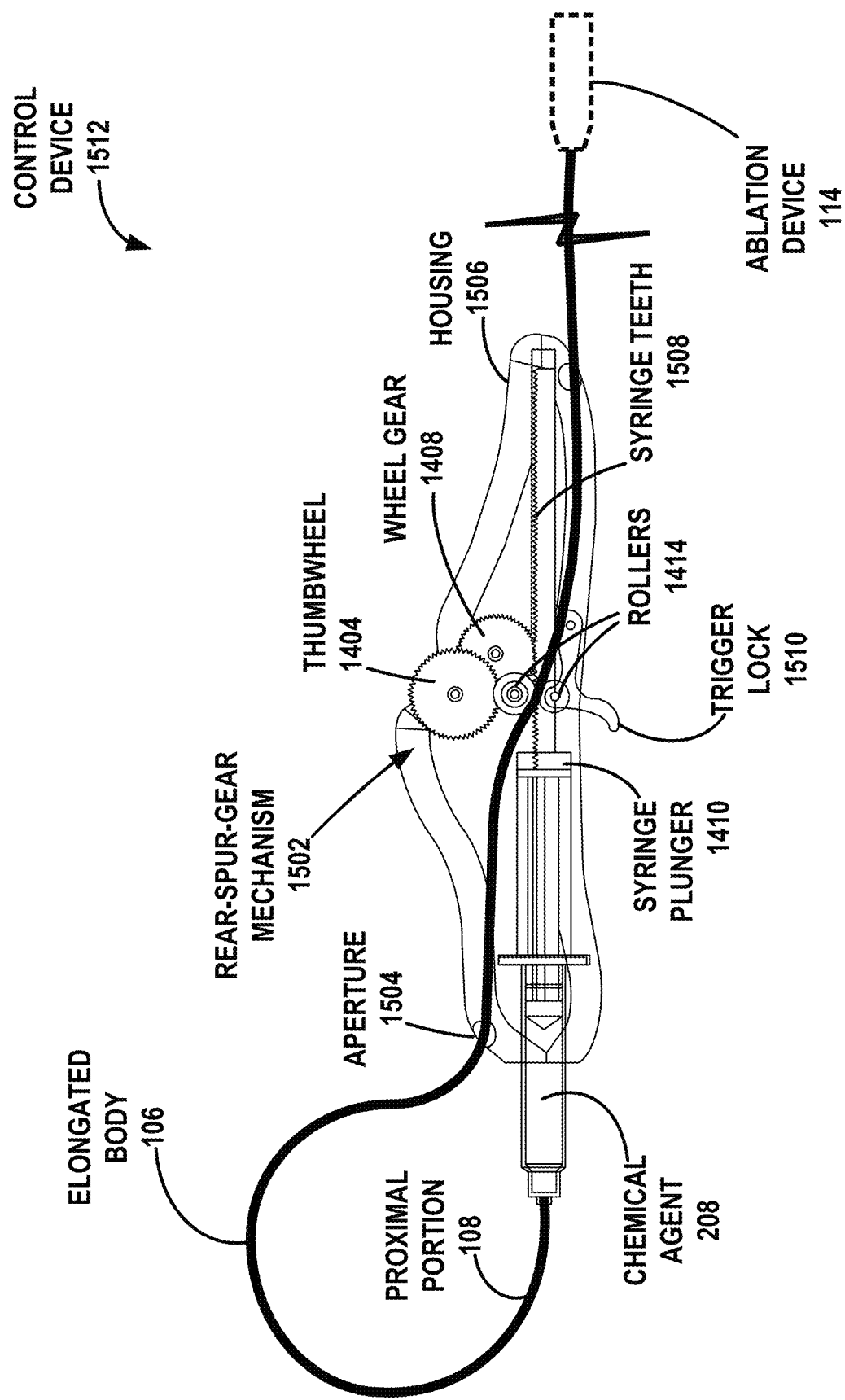
FIG. 15 is a transparent perspective view of an example of the control device of FIG. 1 having an integrated rear-spur-gear mechanism.

FIG. 15 is a transparent perspective view of a manual control device 1512 (e.g., proximal control device 112 of FIG. 1) having an integrated rear-spur-gear mechanism 1502. Rear-spur-gear mechanism 1502 is an example of spur-gear mechanism 1402 of FIG. 14, except for the differences noted herein.

For instance, unlike spur-gear mechanism 1402, in which thumbwheel 1404 is directly engaged with syringe plunger 1410, in rear-spur-gear mechanism 1502 of FIG. 15, thumbwheel 1404 is indirectly engaged with syringe teeth 1508 via wheel gear 1408, such that, from the perspective of FIG. 15, a counterclockwise (rather than clockwise) rotation of thumbwheel 1404 drives syringe plunger 1410 to the left, thereby infusing chemical agent 208 into the inner lumen 210 of elongated catheter body.

Similarly, unlike spur-gear mechanism 1402 in which thumbwheel 1404 is indirectly engaged with catheter rollers 1414 via wheel gear 1408, in rear-spur-gear mechanism 1502 of FIG. 15, thumbwheel 1404 is directly engaged with catheter rollers 1414, such that, from the perspective of FIG. 15, the same counterclockwise (rather than clockwise) rotation of thumbwheel 1404 drives elongated body 106 to the left, thereby proximally retracting ablation device 114 through the target vessel. Put simply, in FIG. 15, the direction of rotation of thumbwheel 1404 is aligned with the operational motions of syringe plunger 1410 and elongated body 106, whereas in FIG. 14, the direction of rotation of thumbwheel 1404 is anti-aligned with the operational motions of syringe plunger 1410 and elongated body 106.

Also shown in FIG. 15 is an optional trigger lock 1510 coupled to catheter rollers 1414, enabling the clinician to lock elongated body 106 in place, and subsequently release, as appropriate. In other examples, control device 1512 can include any suitable number of interlocking gears, enabling the user to modify (e.g., customize) the relative relationships between rotational motion of thumbwheel 1404, longitudinal motion (e.g., proximal retraction) of ablation device 114, and/or longitudinal motion (e.g., distal advancement) of syringe plunger 1410 (e.g., fluid-infusion flowrate) to accommodate the unique clinical needs presented.

Figure 16:
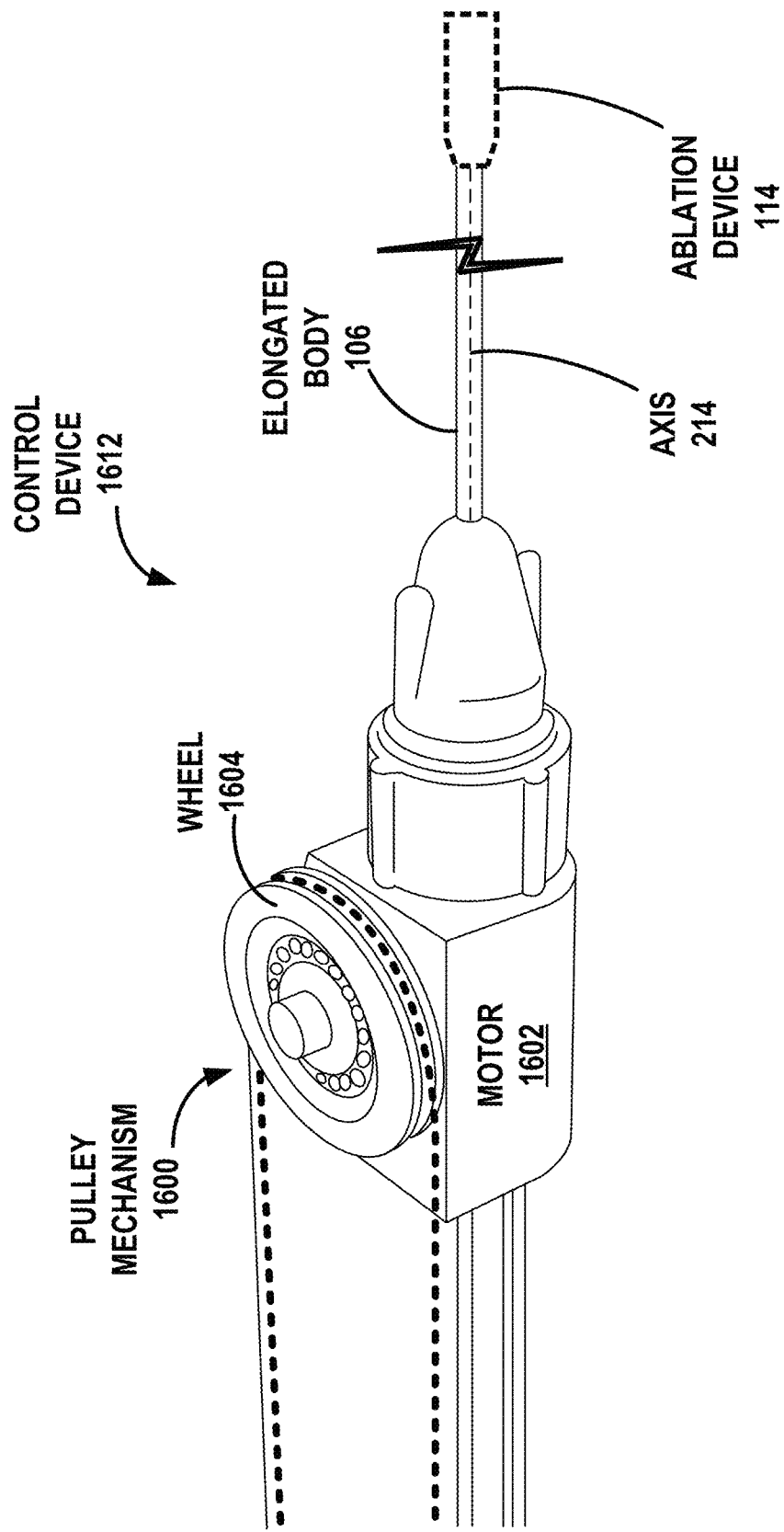
FIG. 16 depicts an example forward pulley mechanism for the ablation system of FIG. 1.

FIG. 16 is a profile view of an example control device 1614 having a "forward" pulley mechanism 1600 configured to drive a longitudinal (e.g., proximal or distal) translation of ablation device 114. For instance, through standard principles, pulley mechanism 1600 is configured to convert a rotational motion, such as from a motor 1602 (e.g., translation driver 318 of FIG. 3) or from manual user-actuation of wheel 1604 (e.g., translation input 312), into a longitudinal motion along central axis 214, thereby proximally withdrawing ablation device 114 through the target vessel 202 within the patient's vasculature. In some examples, pulley mechanism 1600 simultaneously drives infusion of chemical agent 208 into target vessel 202, according to principles similar to those described above, without requiring additional manual user input and/or internal mechanical functionality.

Figure 17A:
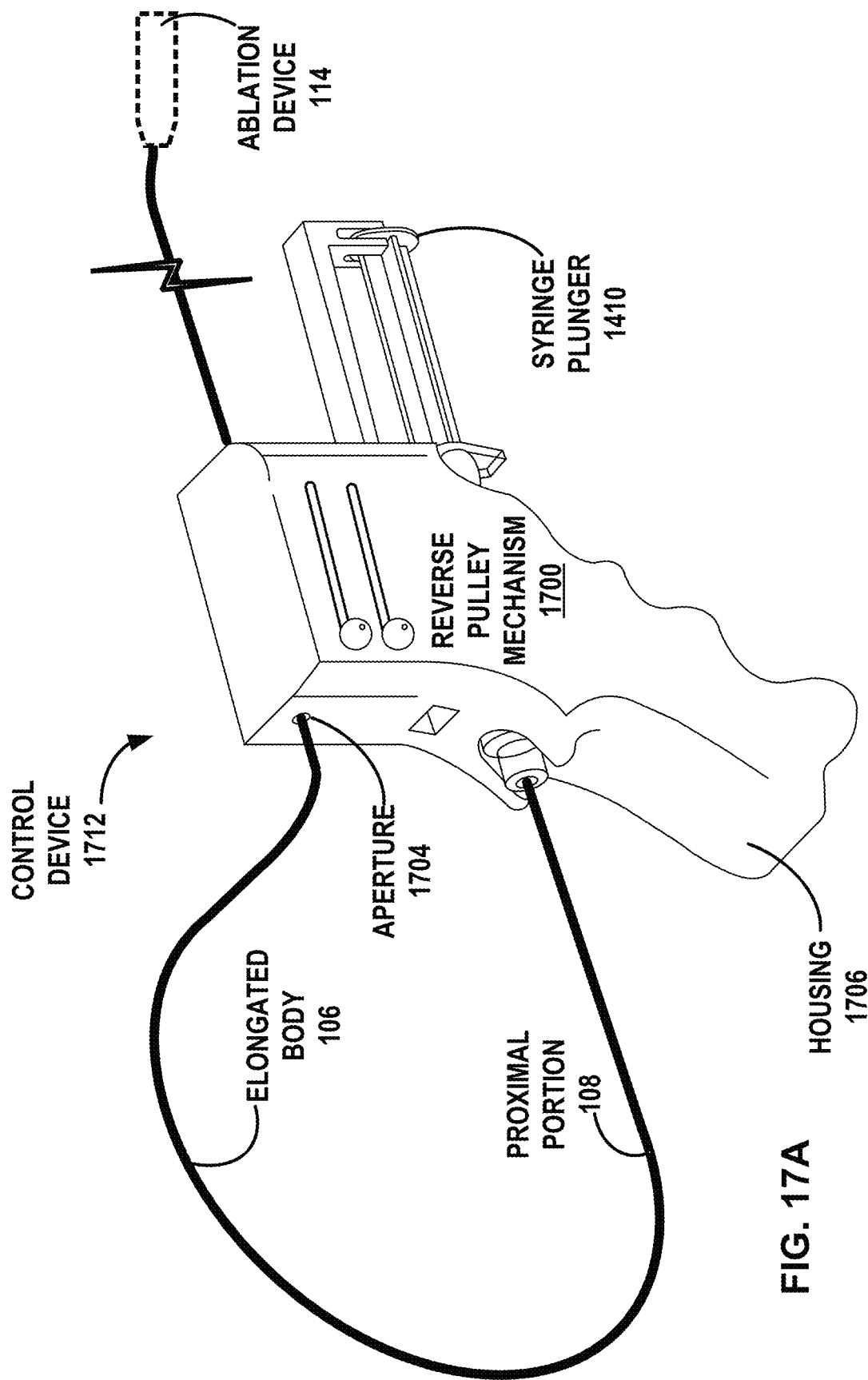
FIGS. 17A and 17B depict an example control device of the ablation system of FIG. 1 having a reverse pulley mechanism.
Figure 17B:
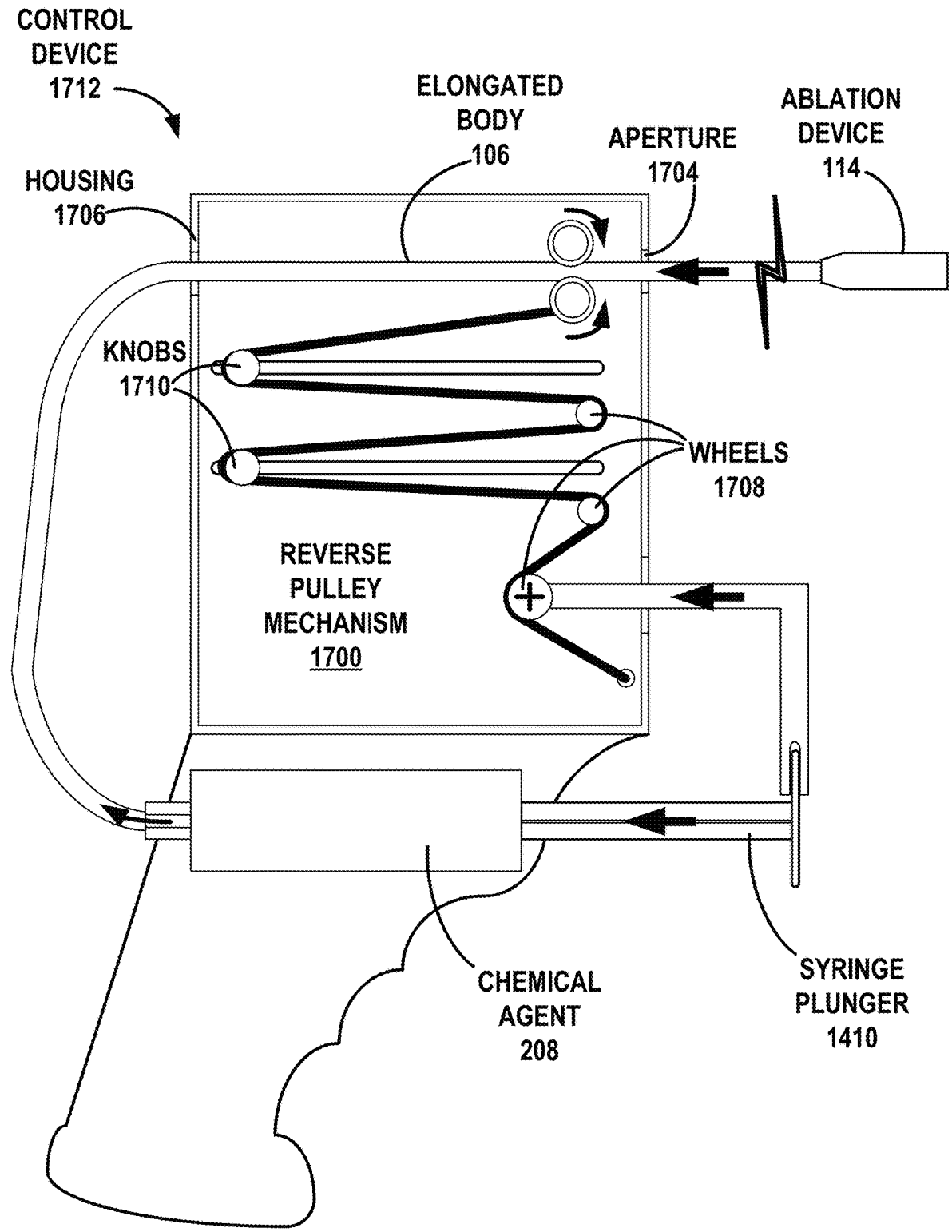

FIG. 17A is a profile view, and FIG. 17B is a conceptual diagram, illustrating a manual control device 1712 (e.g., proximal control device 112 of FIG. 1) having an example "reverse" pulley mechanism 1700. Similar to control devices 1412 and 1512 of FIGS. 14 and 15, respectively, in response to actuation of a user control (in this case, via depression of syringe plunger 1410), control device 1712 is configured to simultaneously drive both longitudinal translation of elongated body 106 and infusion of chemical agent 208. Also similar to control devices 1412 and 1512 is that elongated body 106 extends proximally from the proximal side of housing 1706 of control device 1712, and then loops back and feeds distally through an aperture 1704 defined by housing 1706.

As shown in FIG. 17B, reverse pulley mechanism 1700 includes a plurality of pulley wheels 1708 configured to decrease an applied force necessary for longitudinal translation of elongated body 106 and/or syringe plunger 1410. Reverse pulley mechanism 1700 further includes one or more adjustable knobs 1710 configured to enable the user to customize the rate of motion of syringe plunger 1410 (i.e., the rate of fluid infusion) relative to the rate of motion of elongated body 106 (i.e., the proximal retraction of agitator 204).

Figure 18A:
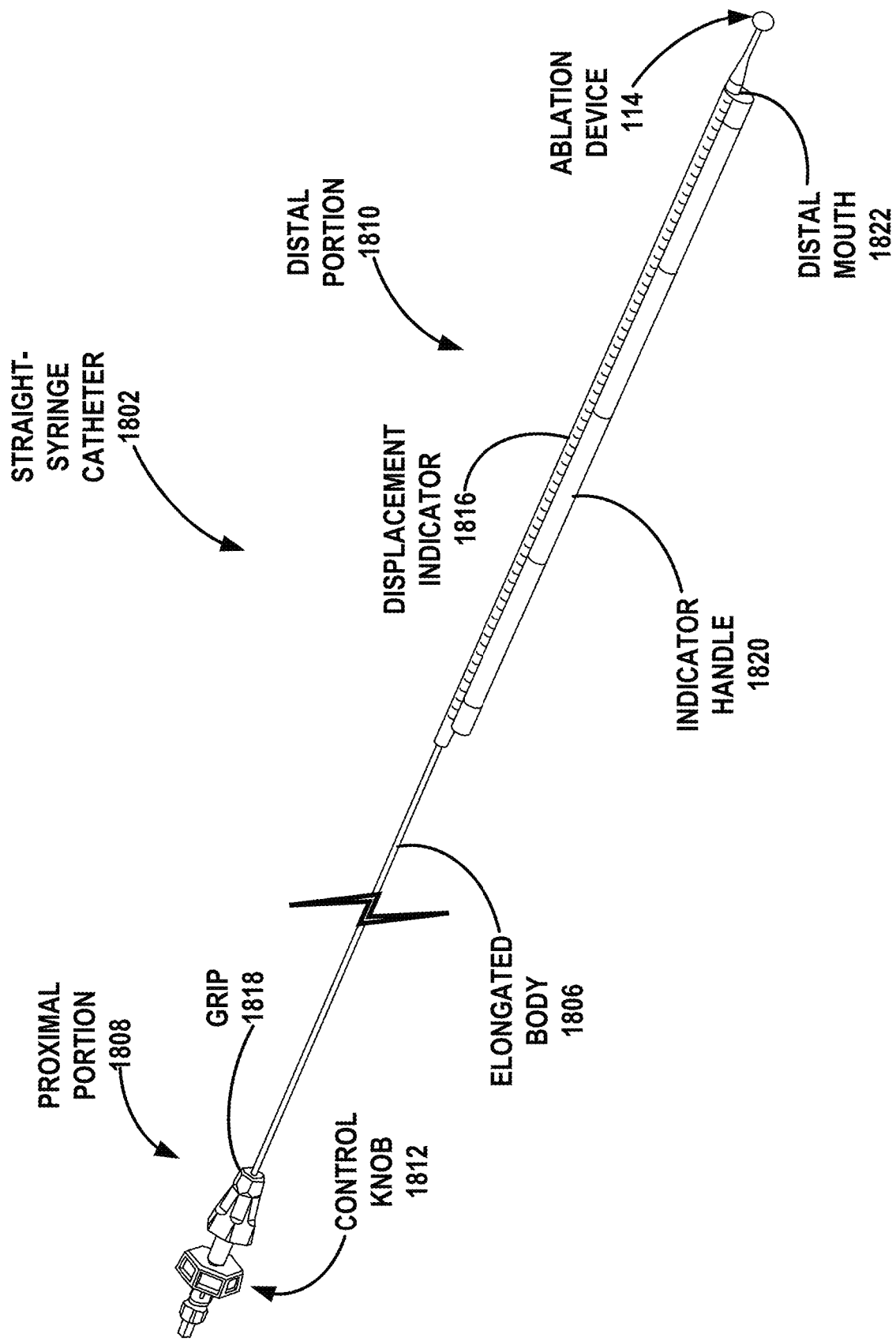
FIGS. 18A-18C illustrate an example straight-syringe catheter of the ablation system of FIG. 1 in a retracted configuration.
Figure 18B:
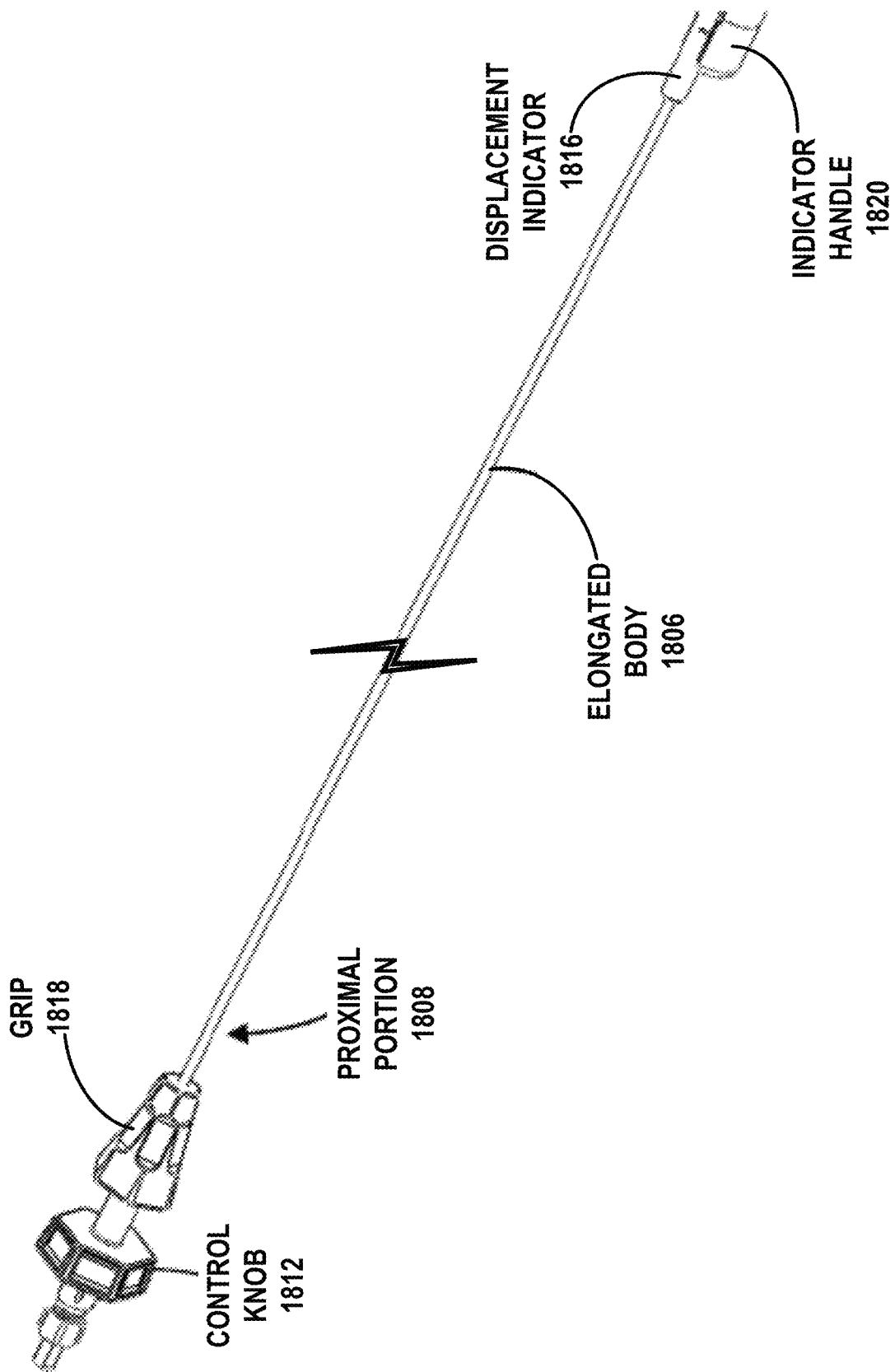
Figure 18C:
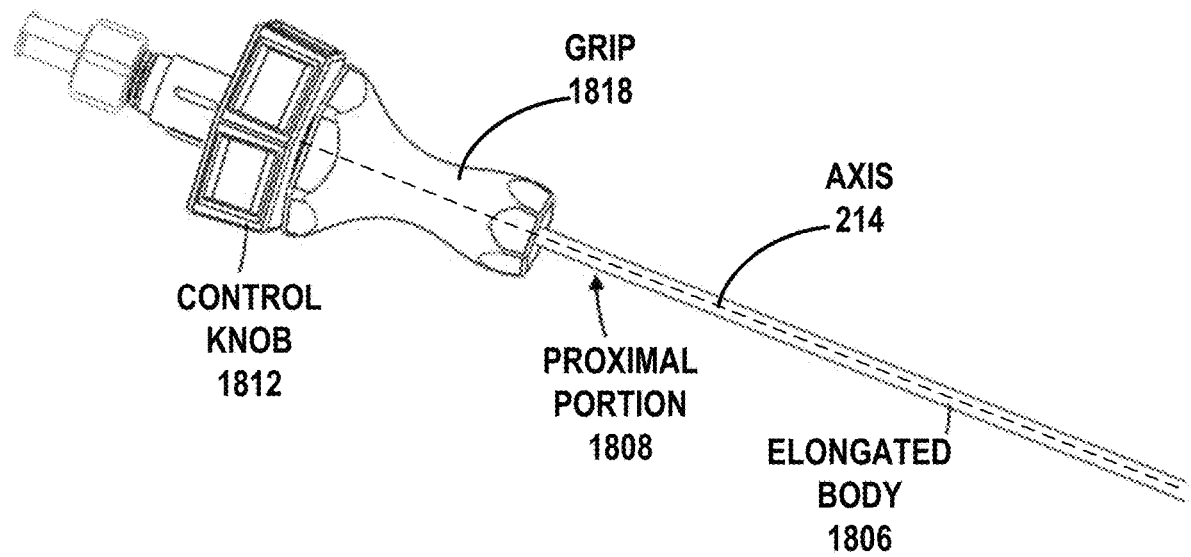
Figure 19A:
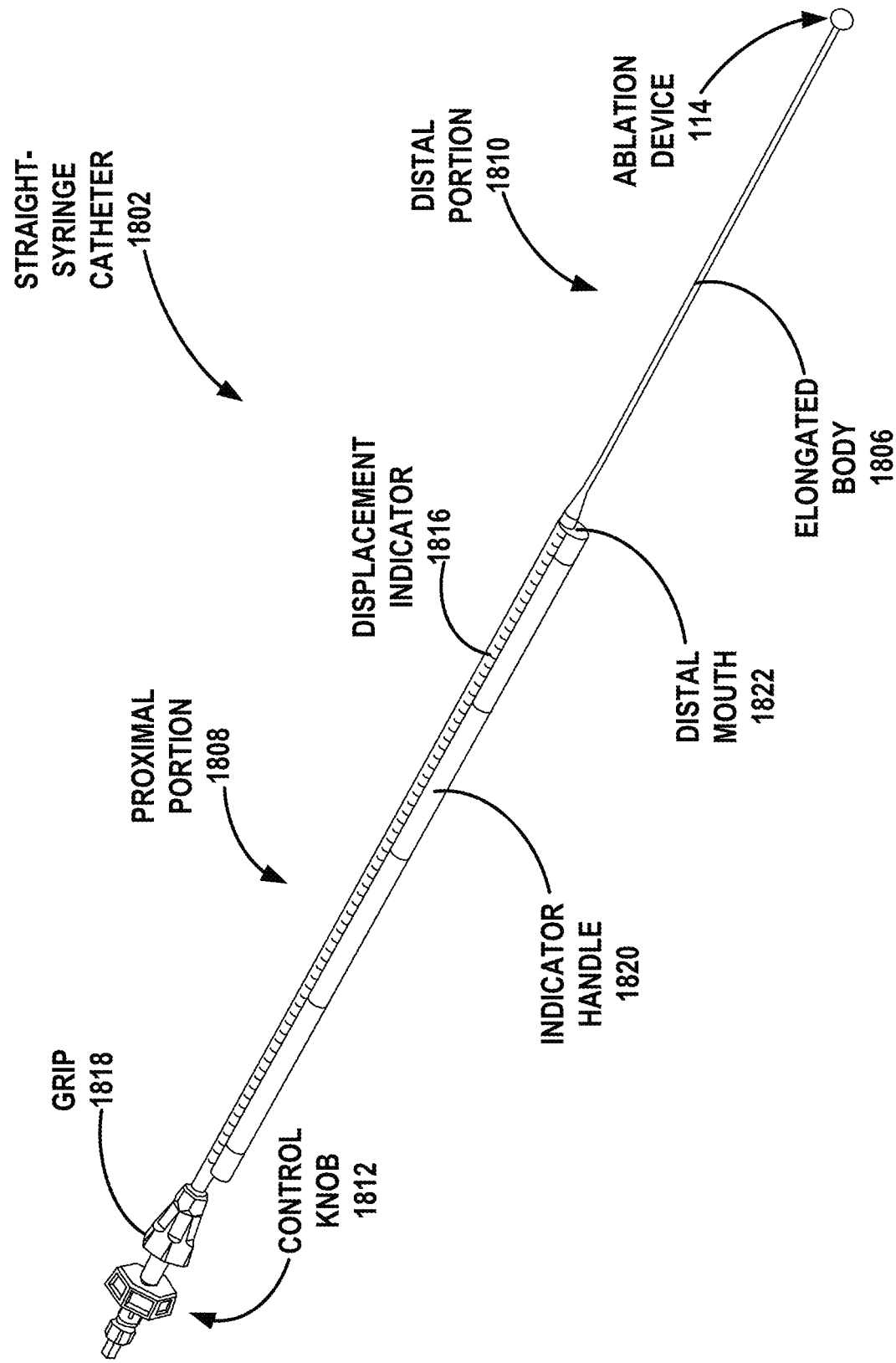
FIGS. 19A-19C illustrate the straight-syringe catheter of FIGS. 18A-18C in an advanced configuration.
Figure 19B:
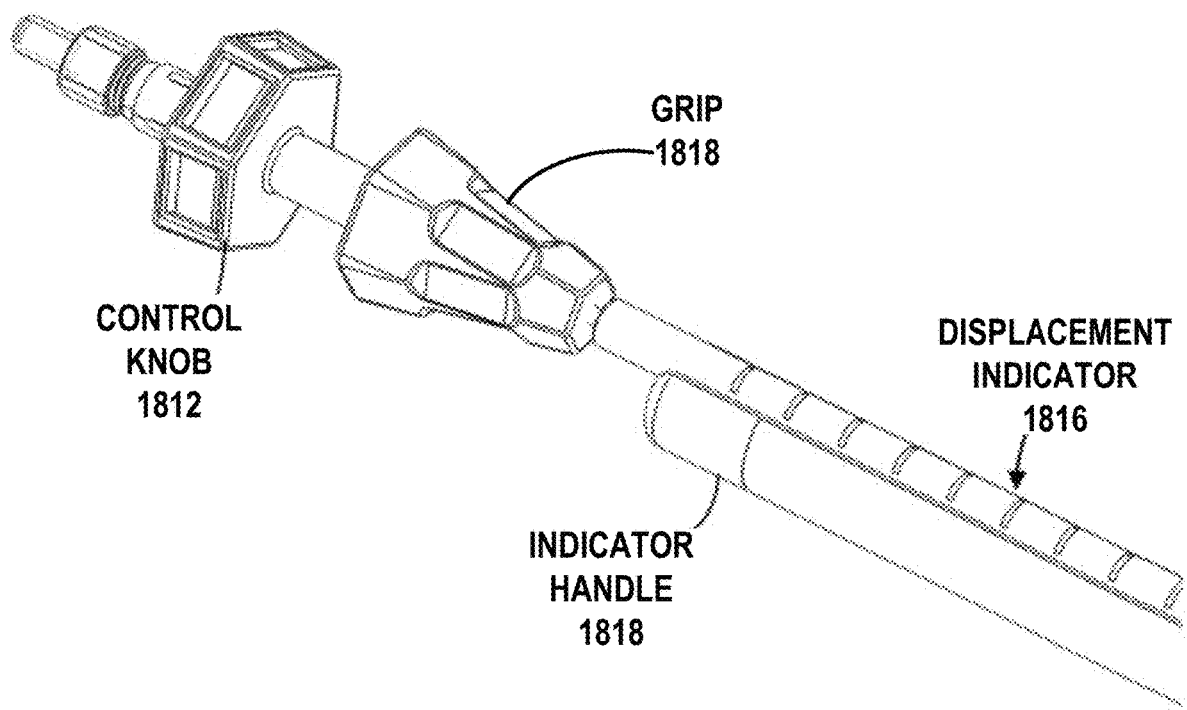
Figure 19C:
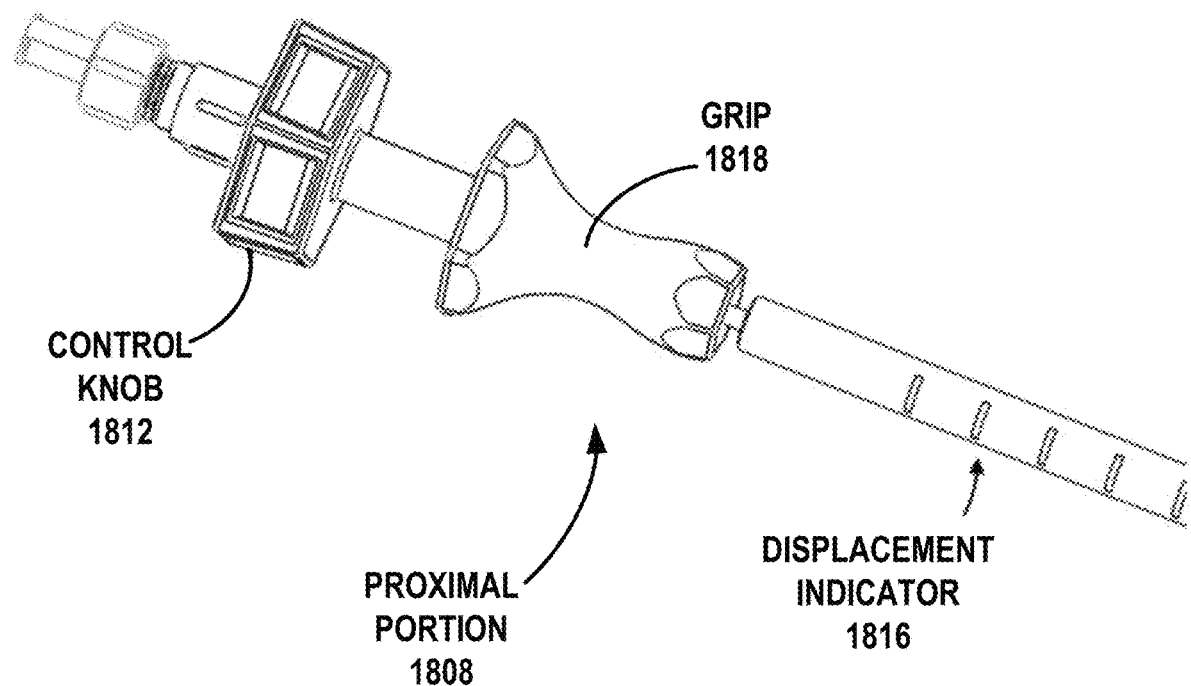

FIGS. 18A-18C illustrate an example straight-syringe catheter 1802 (e.g., catheter 102 of FIG. 1) in a proximally retracted configuration, and FIGS. 19A-19C illustrate straight-syringe catheter 1802 in a distally advanced configuration. More specifically, FIG. 18A is a profile view of straight-syringe catheter 1802, and FIG. 18B is a profile view of a proximal portion 1808 (e.g., proximal portion 108 of FIG. 1) of straight-syringe catheter 1802. As shown in FIGS. 18A and 18B, straight-syringe catheter 1802 includes an elongated body 1806 (e.g., elongated body 106 of FIG. 1), a control knob 1812 (e.g., control device 112 of FIG. 1) and a grip 1818 at the proximal portion 1808 of elongated body 1806, and an ablation device 114 at a distal portion 1810 (e.g., distal portion 110 of FIG. 1) of elongated body 1806. In FIGS. 18A and 18B (but not FIG. 18C), control knob 1812 is positioned slightly proximal from grip 1818, with a longitudinal gap therebetween.

Control knob 1812, which may be a plunger of a syringe, is free to rotate about longitudinal axis 214 (FIG. 18C), relative to indicator handle 1820. Such rotational motion may be manual (e.g., user-driven), or automatic. In some examples, this rotational motion may be translated through elongated body 1806 (or other elongated member 408 therein) and imparted into a rotational agitator 204 (or other similar vessel-abrading mechanism) of ablation device 114.

As shown in FIGS. 18A-19C, elongated body 1806 of straight-syringe catheter 102 extends through a displacement indicator 1816 having an indicator handle 1820. Displacement indicator 1816 includes a plurality of longitudinally spaced demarcations enabling the clinician to estimate a length of elongated body 1806 positioned within the patient's vasculature based on how far toward the indicator handle 1820 that control knob 1812 has moved, thereby allowing for precise control over catheter advancement and withdrawal, and even over rates of speed thereof. In some examples, displacement indicator 1816 additionally enables the clinician to estimate a volume of chemical agent 208 infused into the target vessel (and even a rate of speed thereof).

In the examples shown in FIGS. 18A-18C, control knob 1812 and grip 1818 are positioned significantly proximally from displacement indicator 1816, indicating that the straight-syringe_catheter 1802 is in a proximally retracted configuration. By contrast, in the examples shown in FIGS. 19A-19C, control knob 1812 and grip 1818 are significantly closer to displacement indicator 1816, indicating that the straight-syringe catheter 1802 is now in a distally advanced configuration. In other words, control knob 1812 and grip 1818 have been advanced distally toward displacement indicator 1816, thus advancing elongated body 1806 distally through displacement indicator 1816 and outward from a distal mouth 1822 of displacement indicator 1816, permitting insertion into the vasculature of the patient. As control knob 1812 advances distally toward displacement indicator 1816, the guidewire tube (not shown), and elongated body 1806 translate distally as well. There is a direct relationship between the longitudinal displacement of control knob 1812 relative to displacement indicator 1816, and the longitudinal displacement of the guidewire tube and elongated body 1806 within the patient's vasculature. This relationship may be a direct (e.g., one-to-one) correlation, or may be user-customizable.

Figure 20:
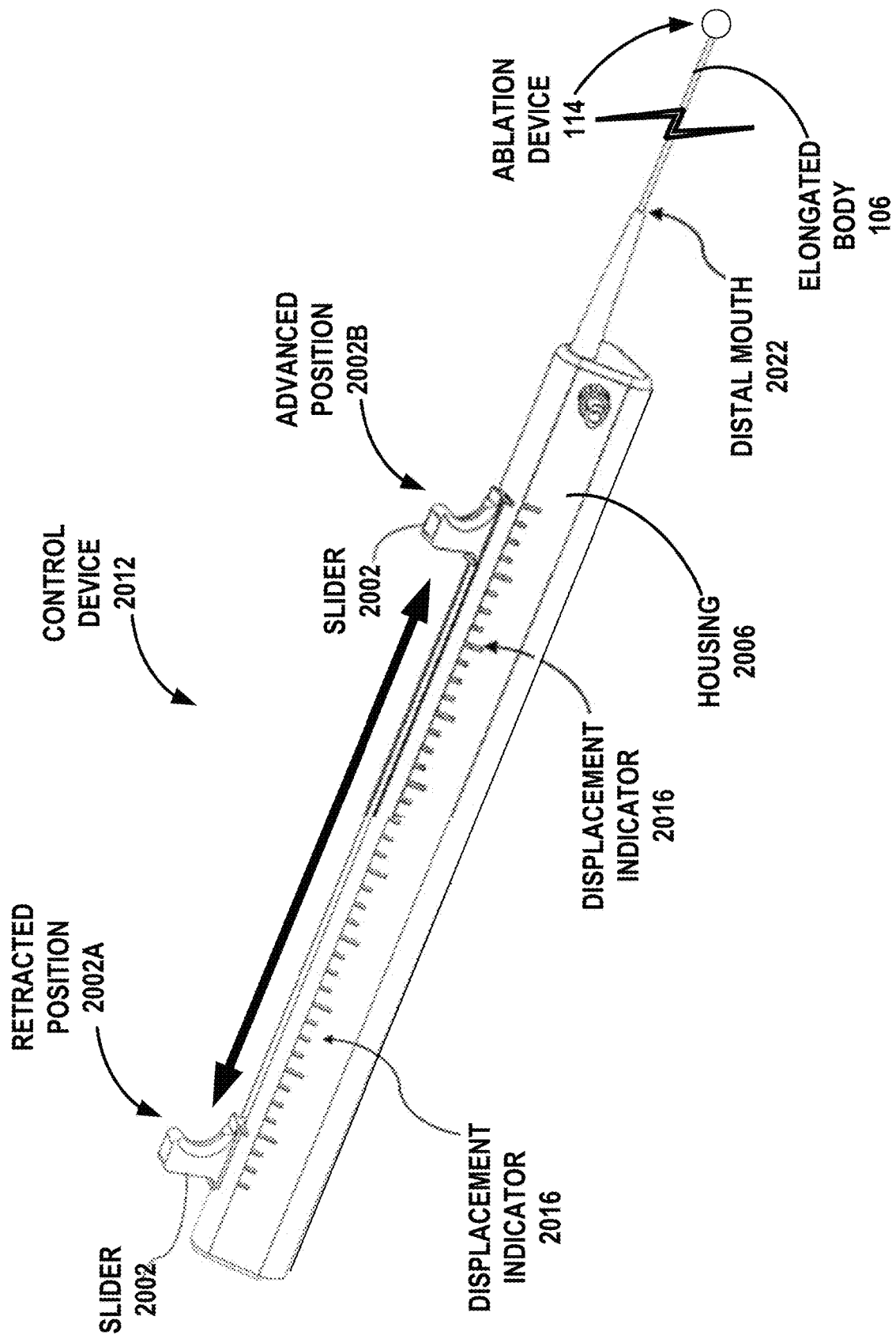
FIG. 20 is a profile view of an example control device of the ablation system of FIG. 1 having a manual slider mechanism.

FIG. 20 is a profile view of an example control device 2012 (e.g., control device 112 of FIG. 1) having a user control (e.g., user control 212 of FIG. 2, translation input 312 of FIG. 3) in the form of a sliding mechanism. During use, the clinician can distally advance slider 2002 from retracted position 2002A to advanced position 2002B in order to extend elongated body 106 distally outward from distal mouth 2022. Once ablation device 114 is positioned within the target vessel, the clinician can then proximally retract slider 2002 from advanced position 2002B to retracted position 2002A in order to linearly translate agitator 204 (FIG. 2) across the inner wall of the target vessel 202.

As illustrated in FIG. 20, an exterior surface of control device 2012 includes a plurality of demarcations forming a displacement indicator 2016, enabling the clinician to determine the distance the catheter has been extended based on how far along the handle the control has moved, thus allowing for fine-tuned control of how far the user is inserting or retracting the catheter, as well as the speed at which they are doing so.

In some examples, control device 2012 includes a fluid reservoir 206 (FIG. 2), e.g., contained within external housing 2006. Fluid reservoir 206 stores chemical agent 208, such as a sclerosant, for injection through inner lumen 210 of elongated body 106 and infusion into the target vessel 202. In some such examples, displacement indicator 2016 enables the clinician to visualize a volume and/or a rate of fluid-infusion from reservoir 206.

Figure 21A:
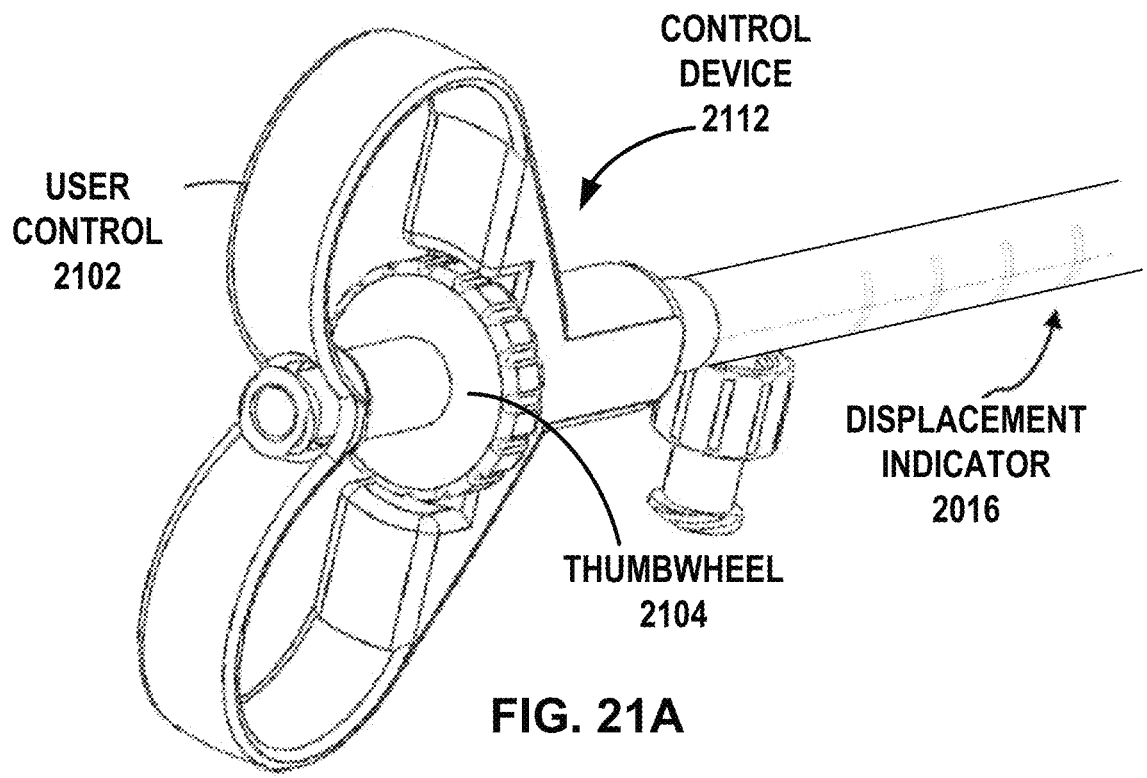
FIGS. 21A and 21B are profile views of an example control device of the ablation system of FIG. 1 having a two-finger pullback mechanism.
Figure 21B:
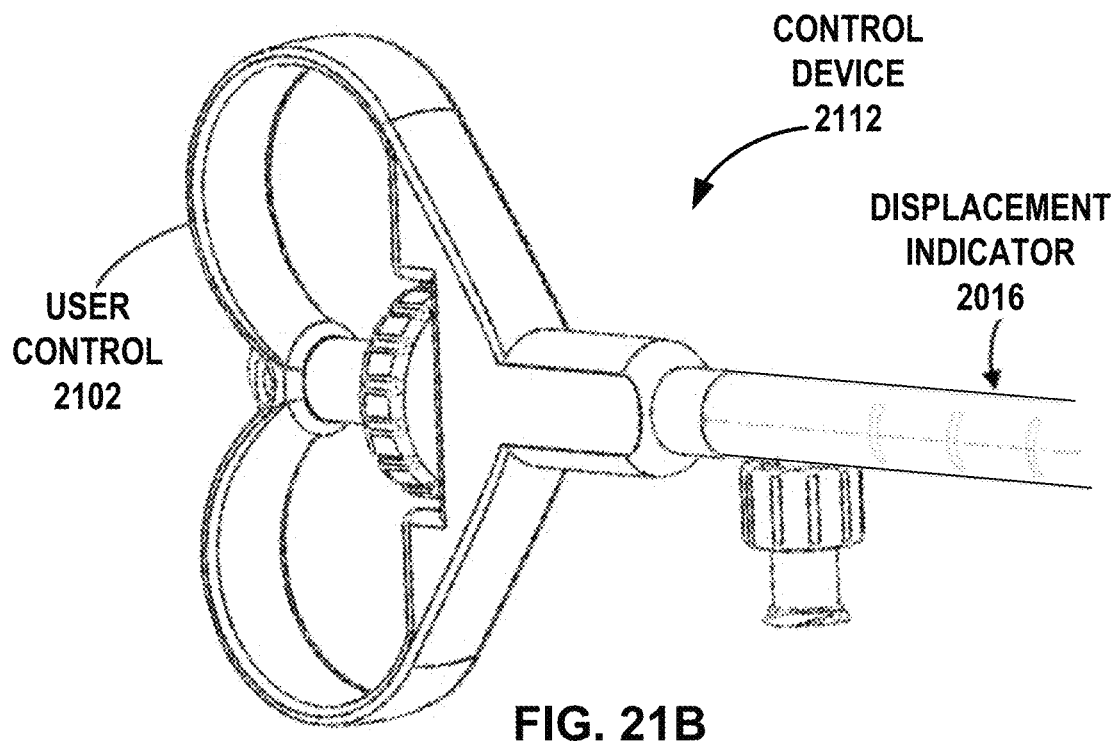

FIGS. 21A and 21B are profile views of an example manual control device 2112 (e.g., proximal control device 112 of FIG. 1) having a user control 2102 (e.g., user control 212 of FIG. 2) in the form of a two-finger pullback mechanism. User control 2102 is configured to enable the clinician to distally infuse chemical agent 208, proximally translate ablation device 114, or both. Additionally or alternatively, since user control 2102 is free to rotate about longitudinal axis 214 relative to elongated body 106 (e.g., via user actuation of thumbwheel 2104), this rotation may be imparted through inner lumen 210 of elongated body 106 and into agitator 204 (FIG. 2). As shown in FIGS. 21A and 21B, demarcations may be present along a portion of control device 2112, forming a displacement indicator 2016, as described above.

Figure 22:
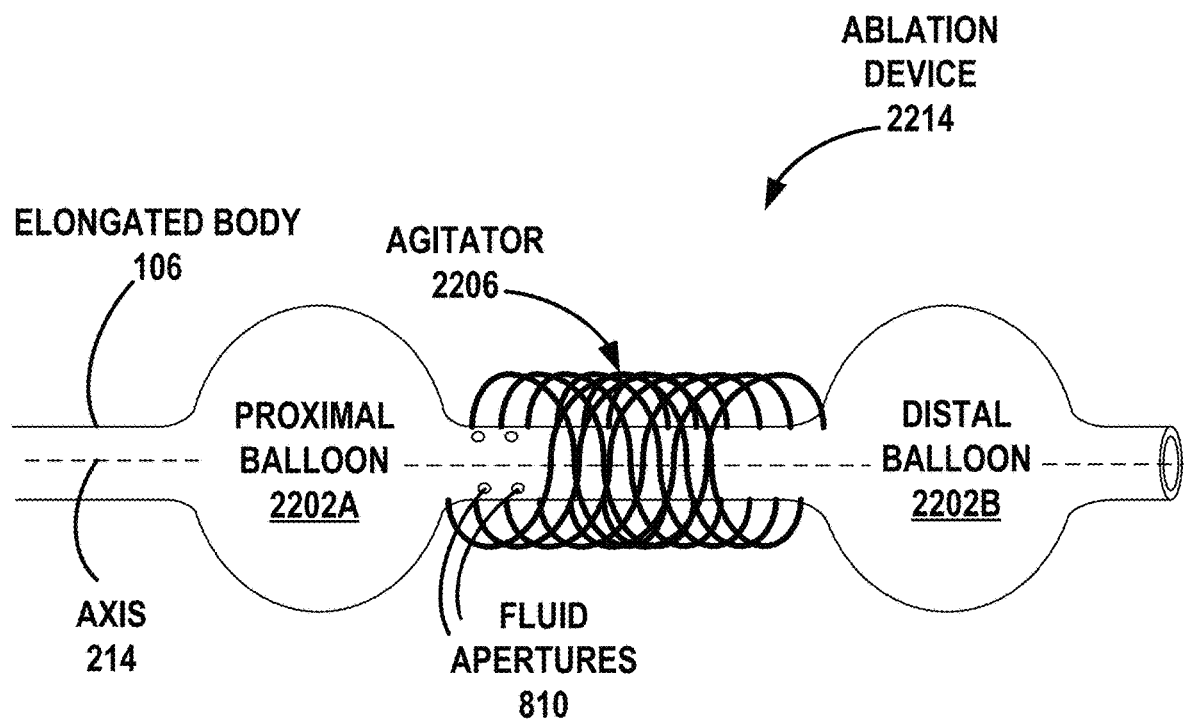
FIG. 22 is a conceptual diagram of an example isolated, segmental mechanical-chemical ablation (ISMA) device of the ablation system of FIG. 1.

FIG. 22 is a conceptual diagram of an example ablation device 2214 (e.g., ablation device 114 of FIG. 1) of ablation system 100. Ablation device 2214 is an example of an Isolated, Segmental Mechanical-chemical Ablation (ISMA) device. In the example shown in FIG. 22, ISMA device includes proximal and distal balloons 2202A, 2202B (e.g., vessel occluder 216 of FIG. 2) spaced longitudinally apart along central longitudinal axis 214. Proximal balloon 2202A is located closer to control device 112 (FIG. 1), and distal balloon 2202B is located near or at the distal end of elongated body 106. A length of elongated body 106 positioned within the longitudinal gap between proximal and distal balloons 2202 can define a plurality of fluid apertures 810 for infusion of chemical agent 208. When balloons 2202 are inflated (or otherwise expanded), they are configured to occlude the target vessel, thereby "isolating" chemical agent 208 to be retained within the space between balloons 2202.

Ablation device 2214 further includes a manually operated or battery-powered agitator 2206 (e.g., agitator 204 of FIG. 2) between balloons 2202. Agitator 2206 includes a polymer or metal wire configured to move (e.g., rotate, oscillated, vibrate, etc.) to contact and score the target vessel wall to promote uptake of chemical agent 208. In some examples, elongated body 106 defines a fluid-aspiration lumen 410C (FIG. 4) enabling the clinician to proximally suction back any unused and/or unabsorbed chemical agent 208.

A general procedure for using the ablation system shown in FIG. 22 starts near the junction of the great saphenous vein (GSV). The clinician inflates proximal and distal balloons 2202, and aspirates any blood from the resulting isolated vessel segment, placing the segment under negative pressure. The clinician infuses a predetermined amount of chemical agent 208 into the isolated vessel segment, and actuates agitator 2206 for a specified duration (e.g., 60 seconds). The clinician then aspirates any unused chemical agent 208 within the isolated segment via an intraluminal catheter. The clinician then deflates only proximal balloon 2202A while maintaining inflation of distal balloon 2202B, before proximally retracting catheter 102 in order to treat the next isolated segment of the target vessel. Proximal balloon 2202A is then reinflated, and the subsequent steps may be repeated as necessary to fully ablate the varicose vein.

Figure 23:
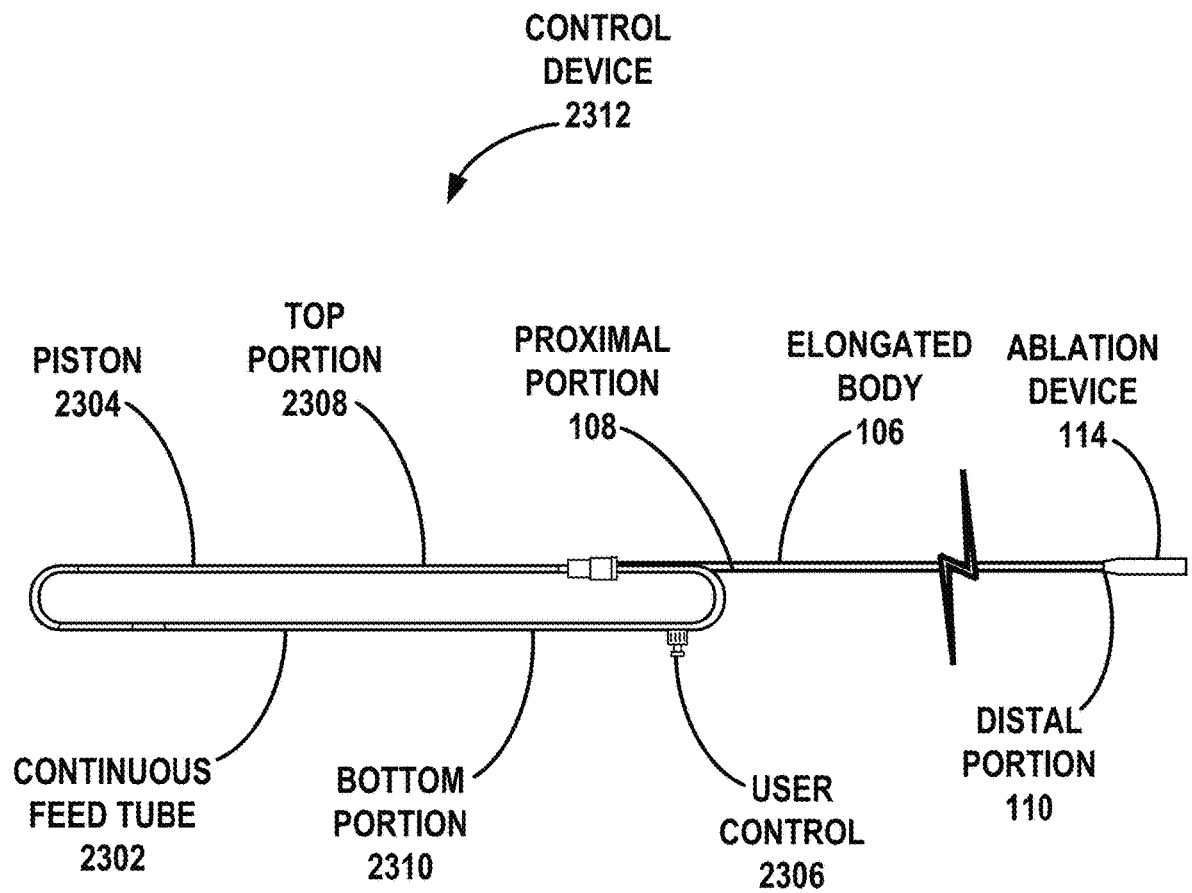
FIG. 23 is a conceptual diagram of an example control device of the ablation system of FIG. 1 having a continuous-feed tube.

FIG. 23 is a conceptual diagram of a manual control device 2312 (e.g., proximal control device 112 of FIG. 1) having a continuous feed tube 2302 configured to simultaneously infuse chemical agent 208 (FIG. 2) and longitudinally translate ablation device 114, as described above. Continuous feed tube 2302 is driven by a piston 2304, which in turn is driven by a flexible member. As used herein, a "flexible member" refers to any suitable non-rigid structure that may be used for longitudinally pushing or pulling elongated body 106, such as a cord, chain, rope, belt, or the like. When user control 2306 (e.g., user control 212) on the bottom portion 2310 of continuous feed tube 2302 is pulled back, the flexible-member-driven piston 2304 pulls back on the bottom portion 2310 and pulls forward on the top portion 2308. This pull-back on the bottom portion 2310 of the continuous feed tube 2302 is configured to proximally withdraw elongated body 106 from the target vessel 202 (FIG. 2) within the patient's vasculature. Simultaneously, the pull-forward on the top portion 2308 of the continuous feed tube 2302 is configured to infuse chemical agent 208 from ablation device 114 at the distal portion of 110 catheter 102.

Figure 24:
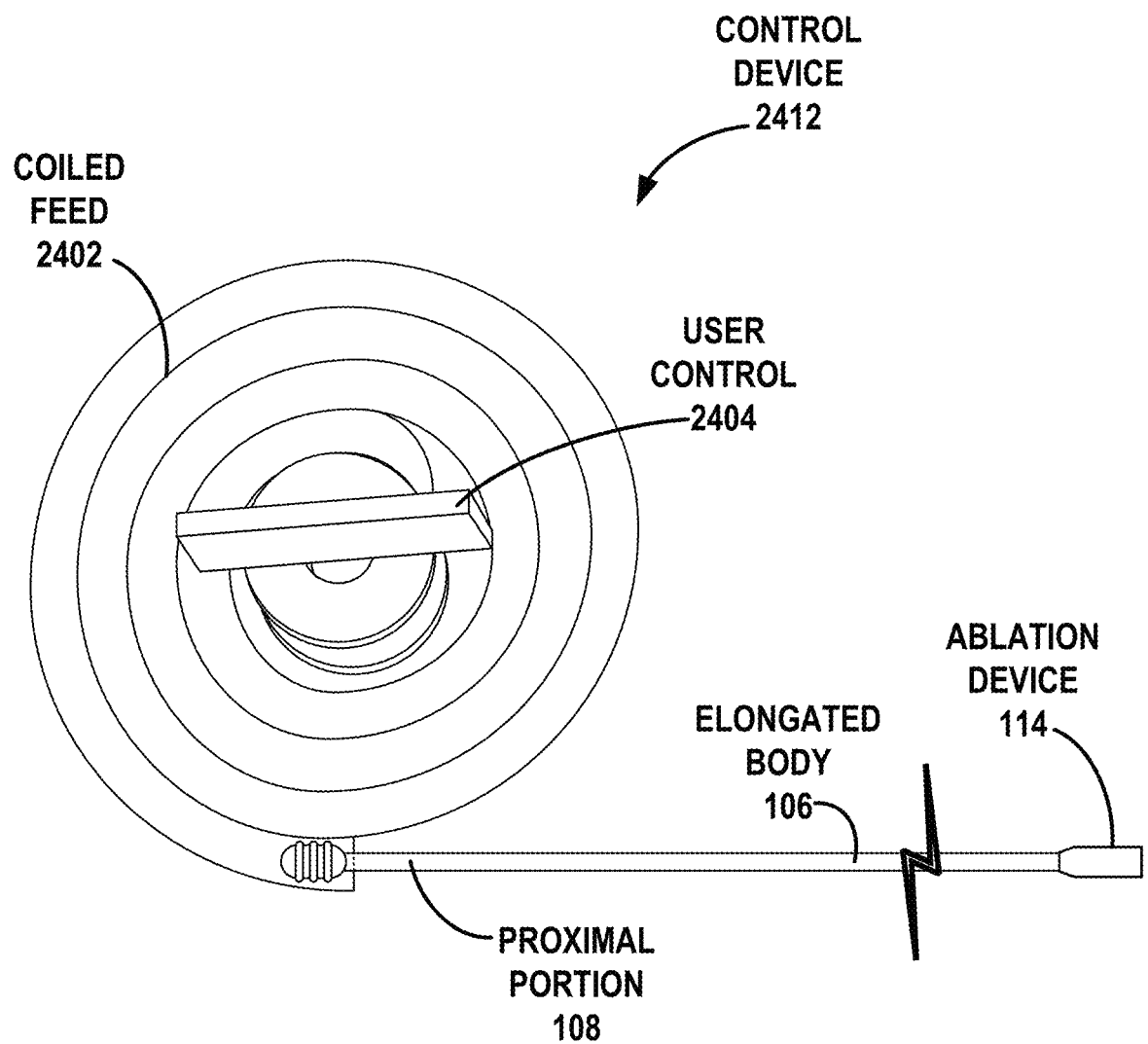
FIG. 24 is a conceptual diagram of an example control device of the ablation system of FIG. 1 having a coiled feed mechanism.

FIG. 24 is a conceptual diagram of a manual control device 2412 (e.g., proximal control device 112 of FIG. 1) having a coiled feed tube 2402 configured to simultaneously infuse chemical agent 208 (FIG. 2) and longitudinally translate ablation device 114, as described above. The clinician can manually actuate (e.g., twist) user control 2404 (e.g., user control 212 of FIG. 2, and fluid-infusion input 310 and translation input 312 of FIG. 3) to wrap or unwrap an elongated portion of coiled feed tube 2402 from around user control 2404. For instance, by twisting user control 2404 clockwise (from the perspective shown in FIG. 24), coiled feed tube 2402 becomes further wrapped around user control 2404, thereby longitudinally translating (e.g., proximally withdrawing) ablation device 114 through target vessel 202. Simultaneously, the internal compression imparted by the various turns of coiled feed tube 2402 against one another causes chemical agent 208 retained within coiled feed tube 2402 to be "squeezed" distally through elongated body 106 and infused into the target vessel via ablation device 114.

In some examples, the coiled shape of feed tube 2402 enables the longitudinal length of control device 2412 to be reduced, thus decreasing the overall longitudinal footprint of ablation system 100. It is to be understood that any feature, function, or element described in previous or subsequent examples may also be incorporated into the other examples. For instance, consistent with other examples previously described, the ratio between the longitudinal displacement of elongated body 106 and the fluid volume (or flow rate) of chemical agent 208 can be maintained or user-customized, as appropriate.

Figure 25A:
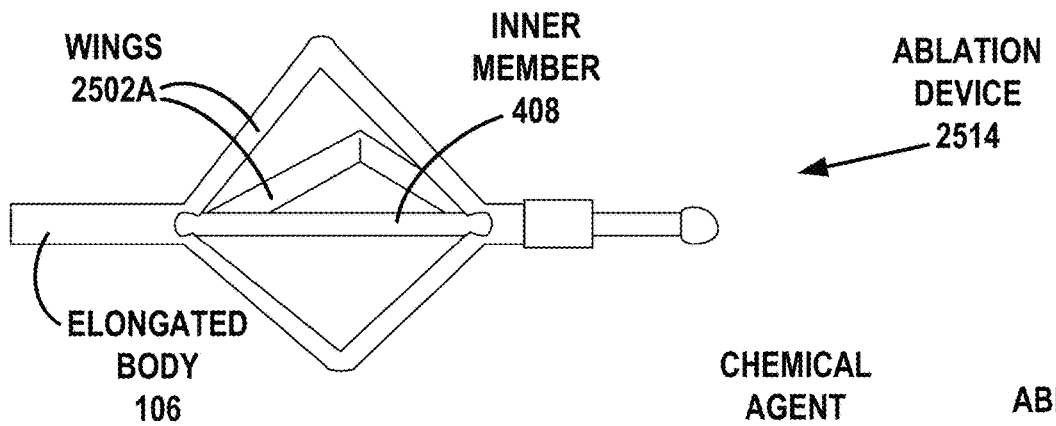
FIGS. 25A-25C are conceptual diagrams of three examples of the ablation device of FIG. 1 having radially expanding wing mechanisms.
Figure 25B:
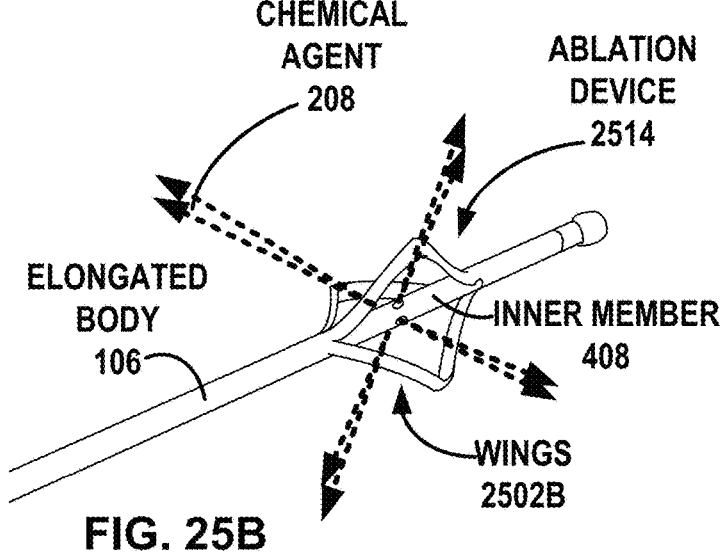
Figure 25C:
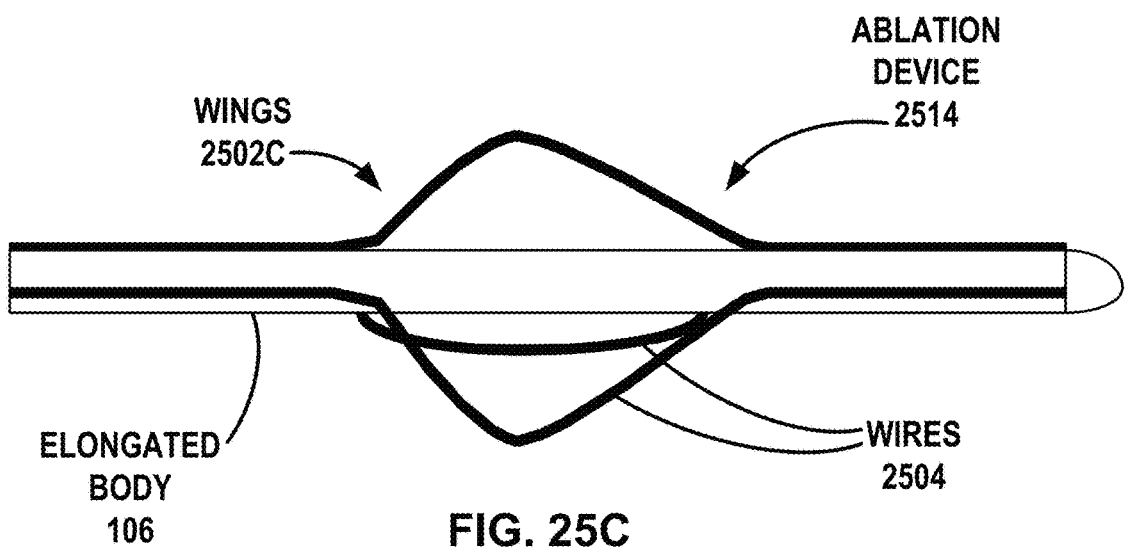

FIGS. 25A-25C are conceptual diagrams of ablation device 2514 (e.g., ablation device 114 of FIG. 1) having radially expanding wings 2502A-2502C, respectively, configured to agitate (e.g., vibrate or rotate) the target vessel and/or infuse chemical agent 208. For instance, FIGS. 25A and 25B illustrate a possible embodiment of the distal portion of elongated body 106 in which the user may distally advance a proximal portion of elongated body 106, proximally retract a distal portion of elongated body 106 (e.g., via a pullwire), or both, to cause the catheter body to "split" into multiple segments distributed circumferentially around inner member 408 before meeting again prior to the distal tip, thereby forming a set of "winged" shapes 2502A, 2502B.

This "winged" shape 2502 enables ablation device 2514 catheter to make greater contact with the inner wall of the target vessel 202, thereby improving vessel abrasion. In the example of FIG. 25A, wings 2502A each define an inner fluid-infusion lumen configured to infuse chemical agent 208 directly into the target tissue. Additionally or alternatively, as shown in FIG. 25B, inner member 408 can define fluid apertures 810 (FIG. 8) configured to infuse chemical agent 208 from between wings 2502B, enabling broader dispersion of the sclerosant.

Wings 2502C of FIG. 25C are examples of wings 2502A, 2502B, except that, instead of the radially expandable wings being formed from portions of elongated body 106, ablation device 2514 includes one or more elongated wires 2504 coupled to the exterior surface of elongated body 106, wherein the wires 2504 are configured to expand radially outward to form wings 2502C. Because the wire(s) 2504 can be made of a stronger, or sharper, material than elongated body 106, wire wings 2502C can further improve abrasion of the target vessel.

Figure 26A:
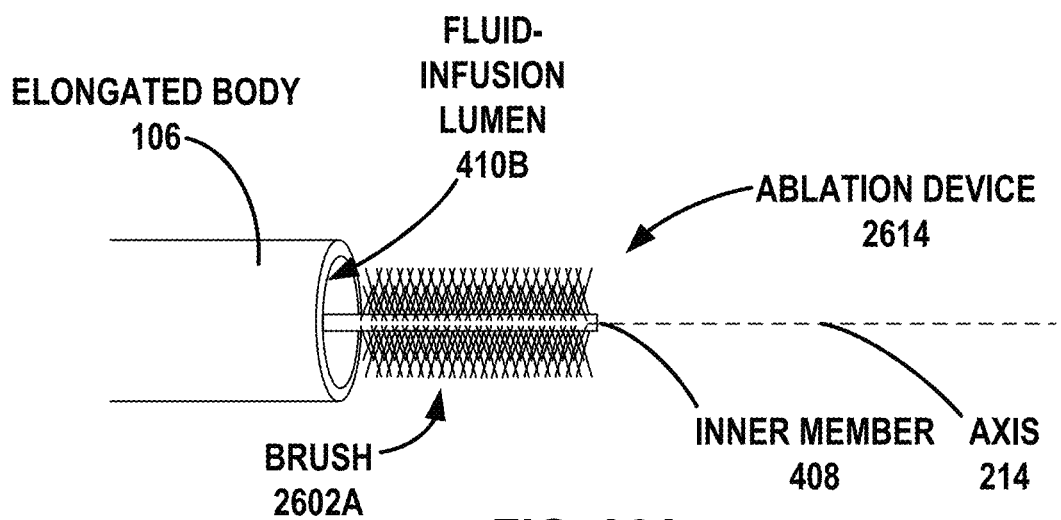
FIGS. 26A-26C are conceptual diagrams of three examples of the ablation device of FIG. 1 having rotating diffusion brushes.
Figure 26B:
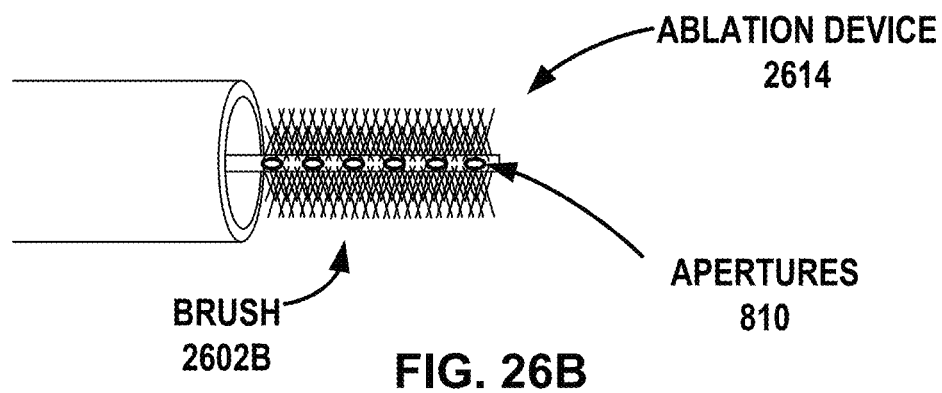
Figure 26C:
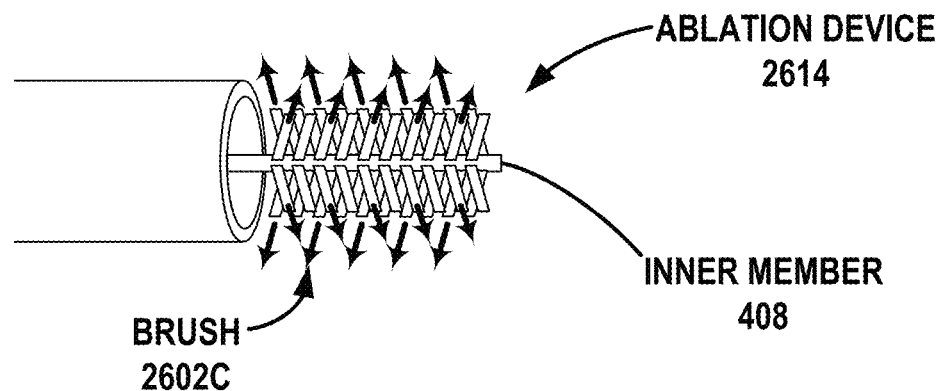

FIGS. 26A-26C are conceptual diagrams of ablation device 2614 (e.g., ablation device 114 of FIG. 1) having rotating diffusion brushes 2602A-2602C (e.g., agitator 204 of FIG. 2) configured to agitate the target vessel 202 and/or infuse chemical agent 208. For instance, as shown in FIGS. 26A-26C, brushes 2602 are configured to extend distally outward from distal catheter mouth 510. In the example shown in FIG. 26A, inner lumen 210 (e.g., fluid-infusion lumen 410B) provides chemical agent 208 to target vessel 202, and may "wet" the brush 2602A with sclerosant while the brush 2602A is sheathed within inner lumen 210. The brush 2602A then rotates about longitudinal axis 214 to disperse chemical agent 208 across the target-vessel wall. In some examples, brush 2602A may have a user-variable longitudinal length, radial diameter, and/or bristle stiffness configured to accommodate the unique clinical needs presented.

Additionally or alternatively, in the example shown in FIG. 26B, inner member 408 defines a plurality of fluid apertures 810 configured to infuse chemical agent 208 along the bristles of brush 2602B. Chemical agent 208 then "wicks" along the bristles and across the target-vessel wall.

Additionally or alternatively, in the example shown in FIG. 26C, each bristle of brush 2602C defines a fluid microtube (e.g., fluid microtubes 706, 806 of FIGS. 7-8C). For example, chemical agent 208 advances distally through inner member 408 of brush 2602C, and is then dispersed from aperture 810 at the radially-outermost end of each fluid-microtube bristle and across the target-vessel wall.

Figure 27A:
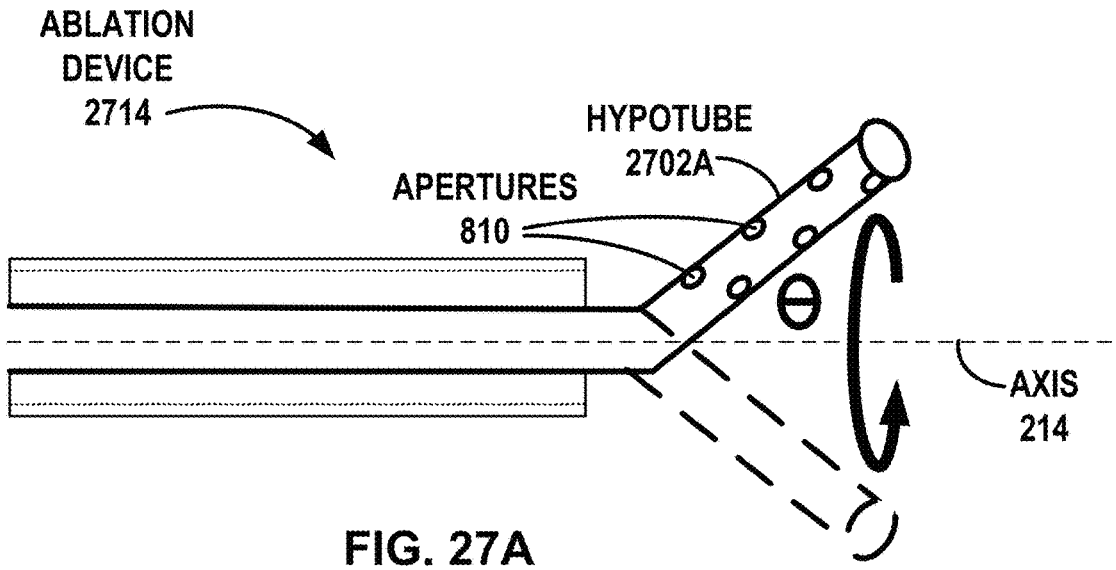
FIGS. 27A and 27B are conceptual diagrams of two examples of the ablation device of FIG. 1 having rotating hypotubes.
Figure 27B:
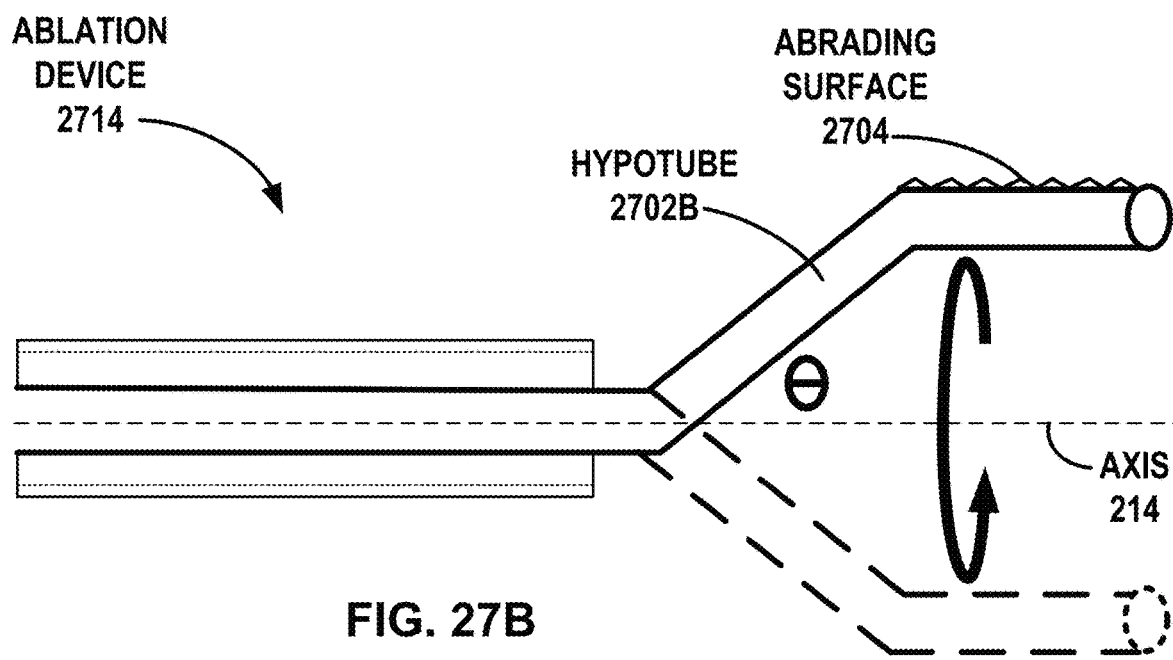

FIGS. 27A and 27B are conceptual diagrams of ablation device 2714 (e.g., ablation device 114 of FIG. 1) having rotating hypotubes 2702A, 2702B, respectively. Hypotubes 2702 are examples of rotating agitator 204 of FIG. 2, and can be configured to rotate about longitudinal axis 214, either in response to manual user-actuation of a user control 212 (FIG. 2), or to rotate automatically during longitudinal translation of ablation device 2714 through the target vessel. In some cases, hypotubes 2702 can rotate fully circumferentially (e.g., a complete 360-degrees about longitudinal axis 214), while in other examples, hypotubes 2702 are configured to rotationally oscillate, e.g., rotate about only a portion of the circumference and then reverse the rotational direction.

As shown in FIG. 27A, hypotube 2702A defines a plurality of fluid apertures 810 configured to infuse chemical agent 208 into the target vessel while hypotube 2702A is stationary, while hypotube 2702A is rotating, or both. Hypotube 2702A of FIG. 27A is illustrated as a laser-drilled hypotube having a distal portion oriented at an angle θ relative to central longitudinal axis 214. This angle can be selected to be any suitable angle from zero degrees (e.g., parallel to longitudinal axis 214) to ninety degrees (e.g., perpendicular to longitudinal axis 214), however, an angle greater than zero enables the distal portion of hypotube 2702A to contact and abrade the vessel wall. In some examples, the distal-most tip of hypotube 2702A may be either closed (e.g., for increased vessel contact and abrasion), or open (e.g., for infusion of chemical agent 208).

As shown in FIG. 27B, the distal portion of hypotube 2702B angles away from longitudinal axis 214, then angles back to be parallel with longitudinal axis 214, such that the distal portion of hypotube 2702B is radially offset from the central longitudinal axis 214, thereby providing vessel-wall contact along the entire distal portion (as compared to just at the distal-most tip, as with hypotube 2702A). Either or both of the offset angle θ and the offset distance may be adjusted by the operator based on the presented clinical needs. In the example shown in FIG. 27B, a radial-outward-facing surface of the distal portion of hypotube 2702B includes an abrading member 2704 (e.g., a rough or serrated surface) configured to further improve vessel-wall abrasion during infusion of chemical agent 208.

Figure 28A:
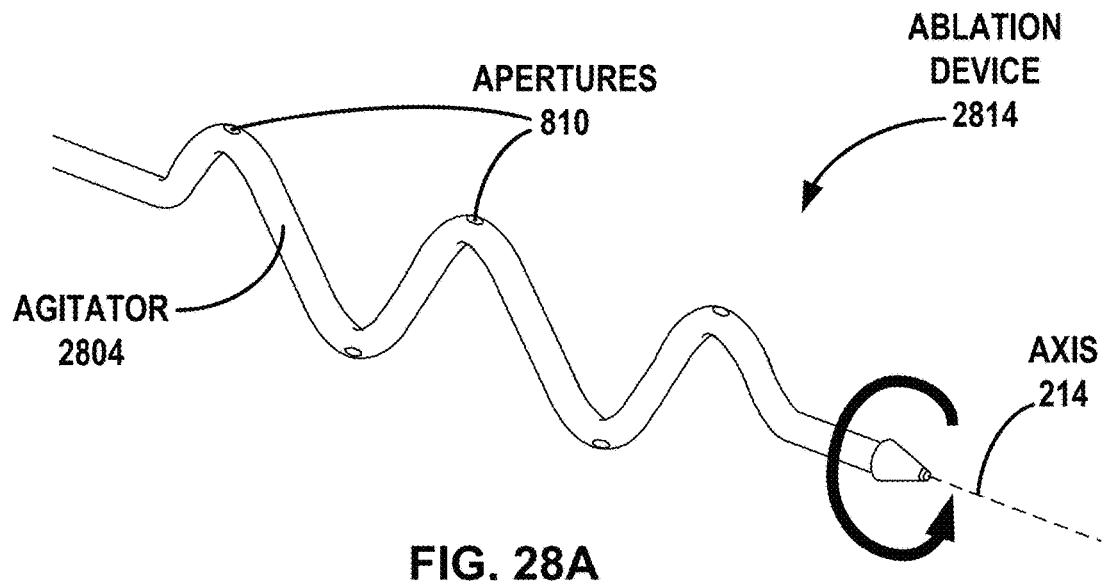
FIGS. 28A and 28B are conceptual diagrams of two examples of the ablation device of FIG. 1 having rotating sinusoidal mechanisms.
Figure 28B:
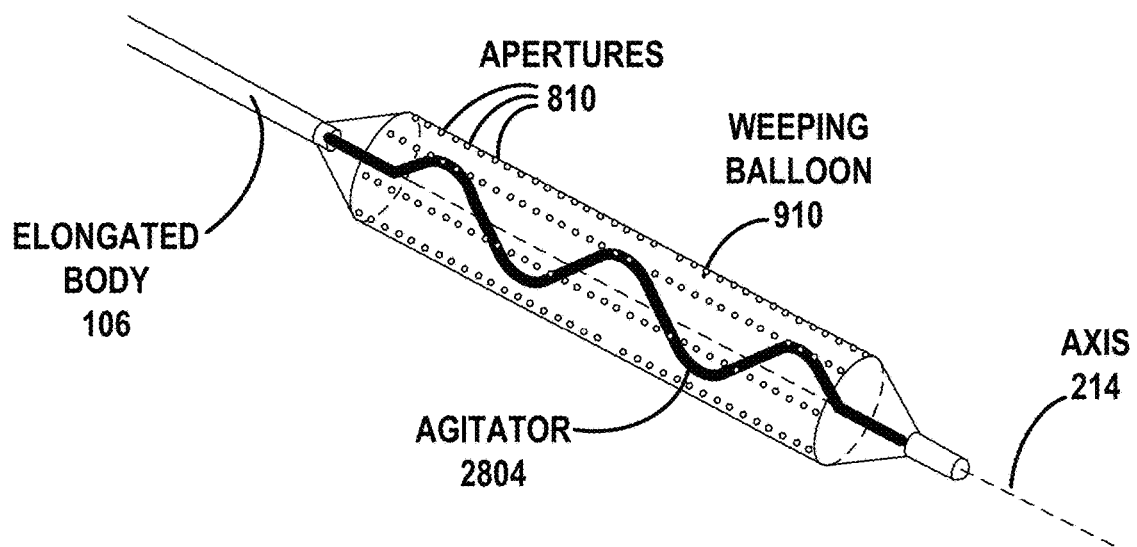

FIGS. 28A and 28B are conceptual diagrams of an ablation device 2814 (e.g., ablation device 114 of FIG. 1) having a sinusoidal agitator 2804 (e.g., agitator 204 of FIG. 2). In either example, sinusoidal agitator 2804 rotates either manually or automatically (e.g., under battery power) about longitudinal axis 214, in order to contact and abrade the target-vessel wall.

In the example shown in FIG. 28A, agitator 2804 can be configured to rotate about longitudinal axis 214, oscillate along longitudinal axis 214, vibrate, or a combination thereof, in order to contact and abrade the target-vessel wall. The sinusoidal shape of agitator 2804 permits multiple points of contact, e.g., forming circumferential and/or helical-shaped abrasions as agitator 2804 rotates (or otherwise moves) along the vessel wall. The elongated body of agitator 2804 defines a plurality of fluid apertures 810 configured to infuse chemical agent 208 into the target vessel.

In the example shown in FIG. 28B, sinusoidal agitator 2804 is enclosed within an interventional balloon 910, such as weeping balloon 910 of FIGS. 9C and 9D. In some such examples, in addition to contacting and abrading the vessel wall through the balloon membrane, agitator 2804 can also function as a peristaltic pump by squeezing chemical agent 208 through the porous balloon membrane as it rotates about longitudinal axis 214.

Figure 29A:
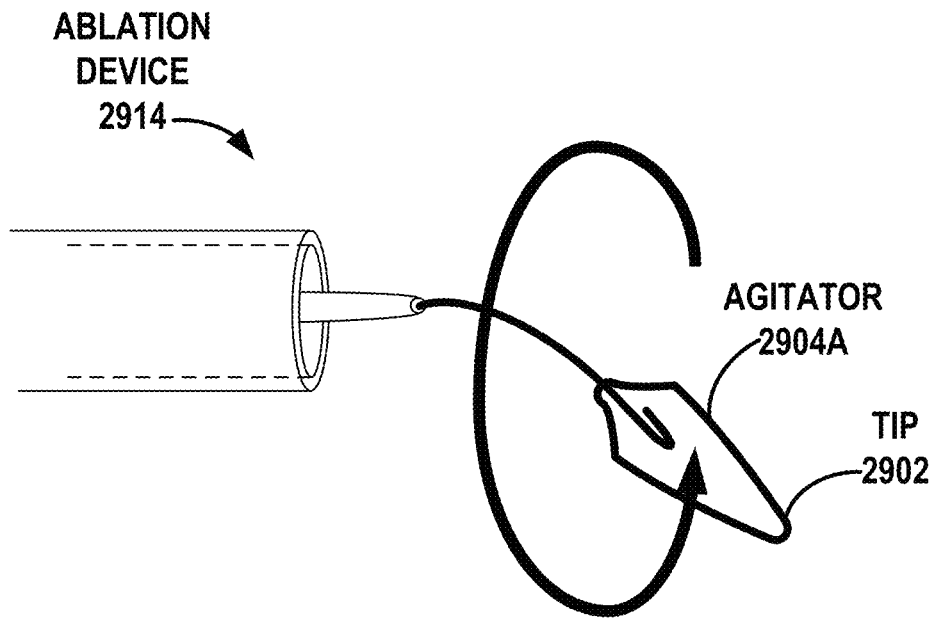
FIGS. 29A and 29B are conceptual diagrams of two examples of the ablation device of FIG. 1 having rotating wire-loop mechanisms.
Figure 29B:
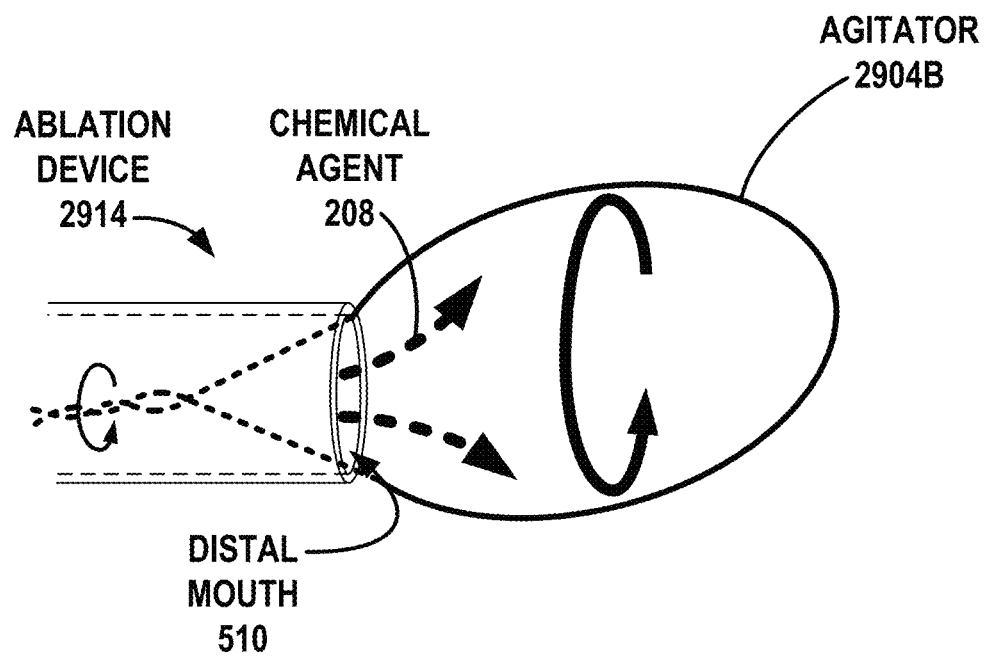

FIGS. 29A and 29B are conceptual diagrams of an ablation device 2914 (e.g., ablation device 114 of FIG. 1) having a rotating agitator 2904A, 2904B (e.g., agitator 204 of FIG. 2) in the form of a wire-loop mechanism configured to contact and abrade the target-vessel wall. Agitator 2904A of FIG. 29A is a radially "narrower" wire loop having a distal end that forms a dull or rounded point 2902 configured to disrupt the vessel wall. By comparison, agitator 2904B of FIG. 29B is a radially wider, more-circular wire loop providing a wider surface area for contact with the vessel wall. Similar to other examples described above, agitators 2904A, 2904B can include fluid apertures 810 configured to infuse chemical agent 208 into the target vessel. Additionally or alternatively, chemical agent 208 may be infused via distal catheter mouth 510.

Figure 30:
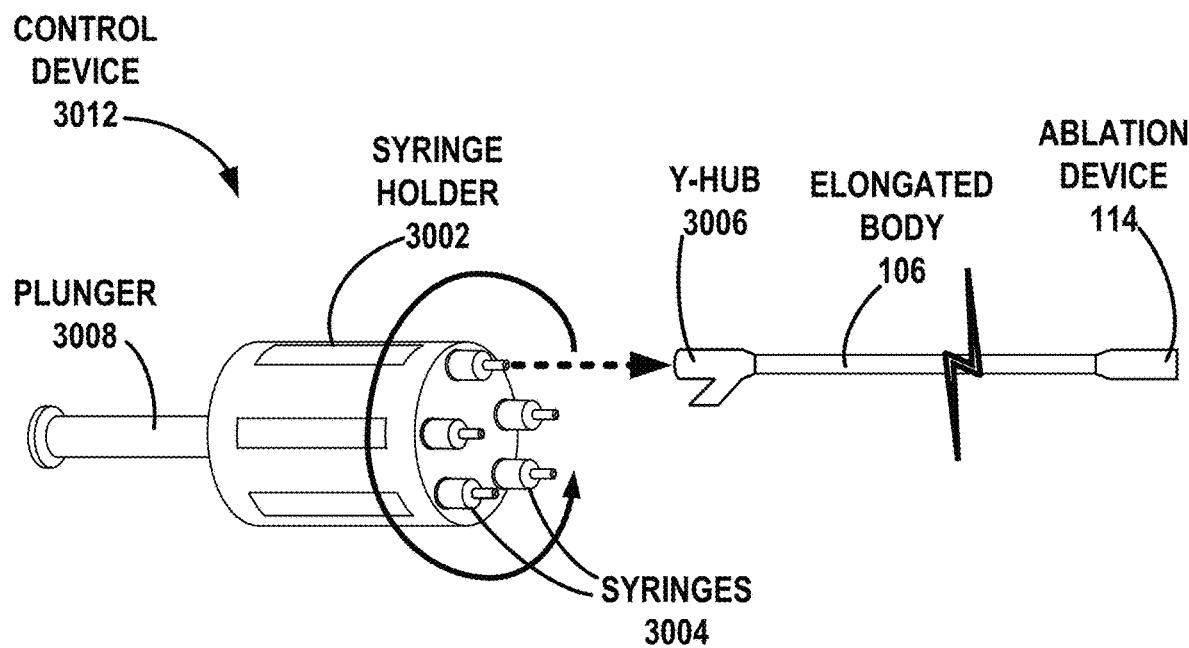
FIG. 30 is a conceptual diagrams of an example control device of the ablation system of FIG. 1 having a rotating syringe holder mechanism.

FIG. 30 is a conceptual diagram of an example control device 3012 (e.g., proximal control device 112 of FIG. 1) having a rotary syringe holder 3002. Syringe holder 3002 is a quick-change system enabling the use of multiple syringes 3004, e.g., in order to either break up a single chemical agent into a set of smaller, controlled infusion "doses," or alternatively, in order to infuse a plurality of different chemical agents at different times throughout the procedure. In some instances, the use of multiple, smaller-volume syringes 3004 can help reduce the risk of bolus injection.

In some examples, a proximal portion 108 (FIG. 1) of elongated body 106 couples to a Y-hub 3006 with a slip-fit syringe connection. During use, rotary syringe holder 3002 rotates to fluidically couple a particular syringe 3004 to the Y-hub connection. Syringe holder 3002 can translate longitudinally to engage and disengage the syringe with the Y-hub 3006. In some examples, each syringe 3004 may have an individual sliding mechanism to deploy the plunger and inject the fluid into the catheter 102. Additionally or alternatively, a single plunger 3008 at the back end may align with the syringe 3004 that is currently engaged with the Y-hub 3006 to inject the fluid into the catheter 102, enabling all syringes to be controlled by a single plunger 3008, thereby decreasing costs of manufacture.

Figure 31A:
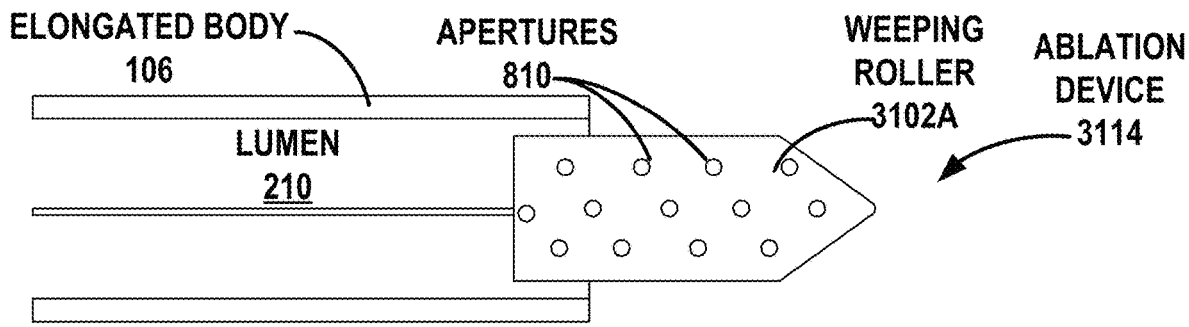
FIGS. 31A-31C are conceptual diagrams of three examples of the ablation device of FIG. 1 having weeping roller mechanisms.
Figure 31B:
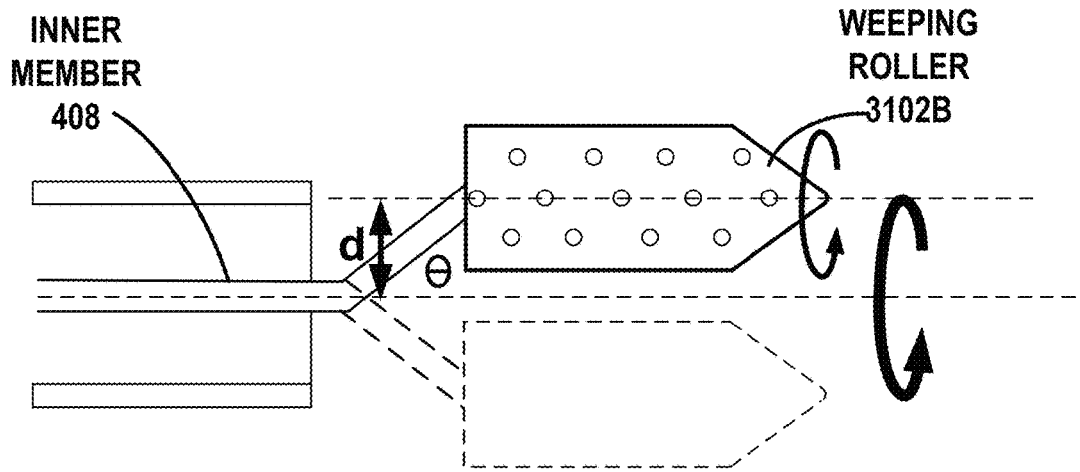
Figure 31C:
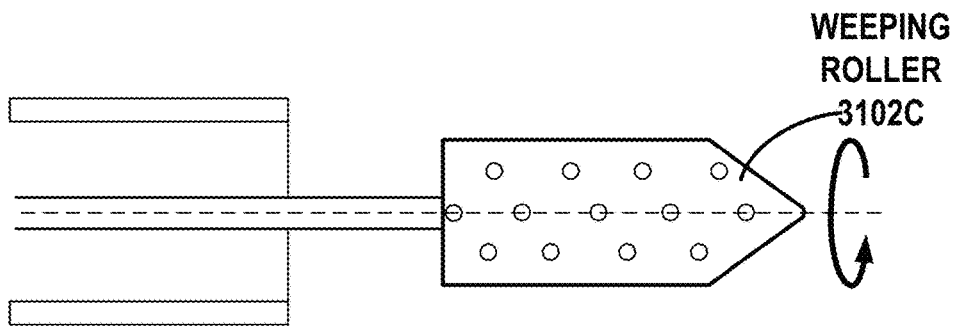

FIGS. 31A-31C are conceptual diagrams of ablation device 3114 (e.g., ablation device 114 of FIG. 1) having a weeping roller 3102 (e.g., agitator 204 of FIG. 2) configured to both agitate the target-vessel wall and infuse chemical agent 208 into the target vessel 202. For instance, FIG. 31A illustrates weeping roller 3102A while partially sheathed within inner lumen 210 of elongated body 106. In some examples, weeping roller 3102A includes a dispersion tip defining a variable pattern (and/or sizes) of fluid apertures 810. Weeping roller 3102 can be configured to either actively "spray" chemical agent 208 from apertures 810, passively "weep" droplets of chemical agent 208 along the vessel wall, or a combination thereof.

Weeping roller 3102A may be attached to a distal end of inner member 408, such as a shape-memory-material (e.g., Nitinol) hypotube, that both delivers chemical agent 208 into weeping roller 3102 and drives the rotation of weeping roller 3102A about longitudinal axis 214. In some such examples, the inner member 408 is configured to assume a preconfigured shape once deployed from distal catheter mouth 510, as shown in FIGS. 31B and 31C.

For instance, FIG. 31B illustrates a radially offset roller 3102B, conceptually similar to radially offset hypotube 2702B of FIG. 27B. That is, inner member 408 is bent at an angle in order to offset roller 3102B from central longitudinal axis 214 to improve contact with the target-vessel wall. In some such examples, ablation device 3114 defines a first axis of rotation (e.g., an axis of revolution) of inner member about central longitudinal axis 214, and a second axis of rotation of roller 3102B about inner member 408. By comparison, FIG. 31C illustrates an axial roller 3102C configured to rotate only about longitudinal axis 214. Such examples are useful for smaller-vessel applications without sufficient space for the off-axis rotation.

FIGS. 32A-32H are conceptual diagrams of a vessel occluder 3216 (e.g., vessel occluder 216 of FIG. 2) having a bioabsorbable plug 3202A-3202H, respectively. During some existing surgical techniques, the clinician infuses a cyanoacrylate (or "cyano") adhesive to embolize or occlude the target vessel 202. In accordance with techniques of this disclosure, the clinician may additionally or alternatively deploy vessel occluder 3216, including an at-least-partially bioabsorbable plug 3202, to perform similar functions. In various examples described herein, plug 3202 can include any or all of an earplug-type mechanism (e.g., a compliant foam), a suture-based plug, an adhesive-like filler (e.g., cyano), or a detachable, fluid-inflatable balloon plug made from suture material (e.g., PDS, etc.). For a balloon-type plug, the balloon can be "permanently" inflated (e.g., as compared to weeping balloon 910) with saline or Polidocanol, and can remain within the target vessel 202 postoperatively. In other words, the plug can include a "detachable" balloon configured to weep sclerosant both during and after the procedure. As detailed further below, the plug can include a braided suture with a "skin" layer overtop, and/or a self-expanding stent that is "sausage-tied" closed on either end.

Figure 32A:
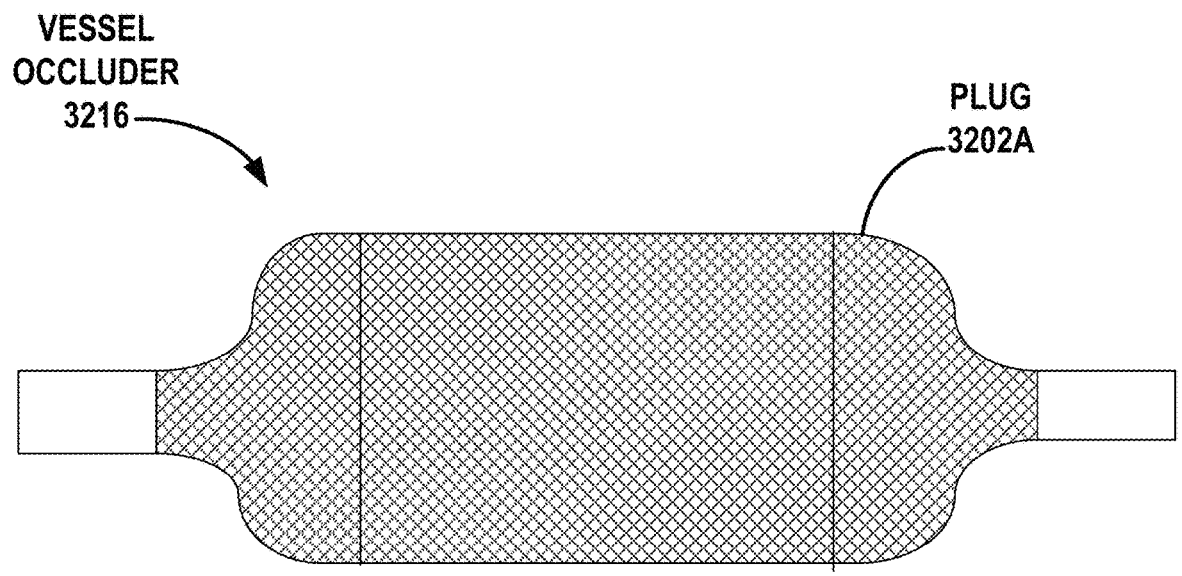
FIGS. 32A-32H are conceptual diagrams of eight examples of the ablation device of FIG. 1 having bioabsorbable plug mechanisms.

For instance, FIG. 32A shows a stent-like, suture-material plug 3202A configured to occlude the target vessel 202 (FIG. 2). The suture material of plug 3202A may be formed into a braided pattern, with proximal and distal ends sealed using a reflow process. In other examples, plug 3202A forms a full (e.g., fluid-tight) balloon.

Figure 32B:
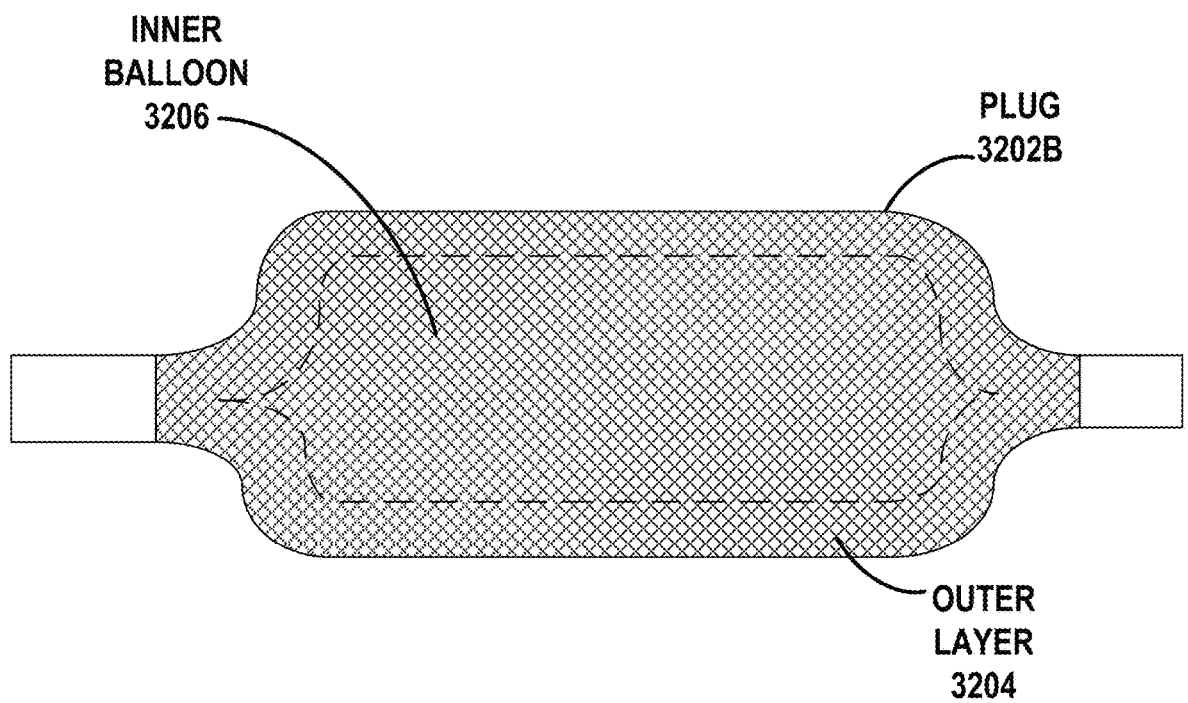

FIG. 32B shows a self-expanding plug having both an outer suture-material layer 3204 and an inner bioabsorbable balloon 3206. Outer layer 3204 can be formed into a braided pattern, as described above. Inner balloon 3206 can be a weeping balloon (e.g., weeping balloon 910 of FIGS. 9C and 9D) and can remain within target vessel 202 while inflated with chemical agent 208.

Figure 32C:
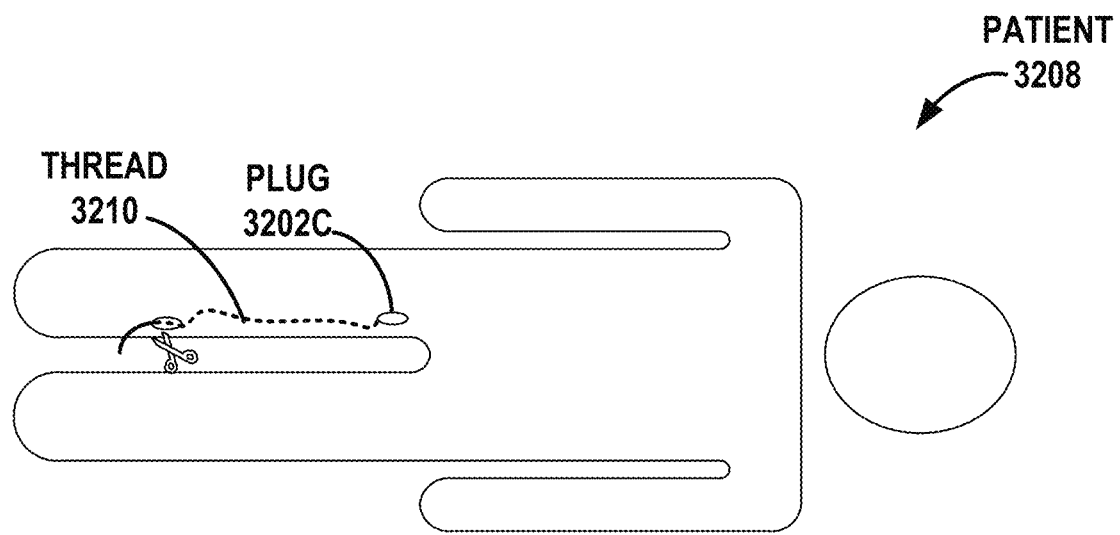

FIG. 32C is a conceptual diagram illustrating techniques for using a bioabsorbable plug 3202C. Plug 3202C can include a braided, bioresorbable suture material with an occluded distal end. Additionally or alternatively, plug 3202C can include a sponge-type thread, or a hydroscopic-gel thread. In some examples, plug 3202C includes bioresorbable coils similar to typical brain-occlusion coils for the treatment of strokes.

In general, the clinician may use plug 3202C by navigating elongated body 106 (FIG. 1) to the target vessel within the patient 3208. Once in place, the clinician deploys bioabsorbable plug 3202C from distal catheter mouth 510 to occlude the target vessel and/or to secure the position of plug 3202C within the patient's vasculature. Catheter 102 may subsequently be withdrawn from the patient. The catheter is then withdrawn while laying out an expandable access thread 3210 from the bioabsorbable plug for subsequent plug removal, if necessary. Finally, the clinician may cut any excess proximal portion of thread 3210 and tuck it into the access site.

Figure 32D:
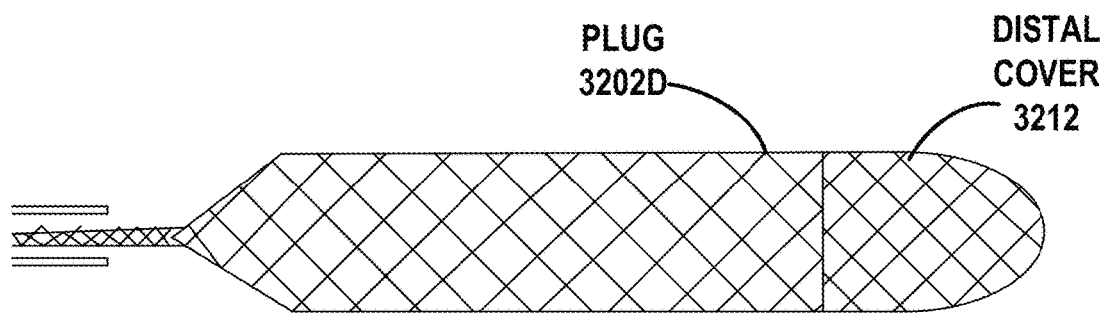
Figure 32E:
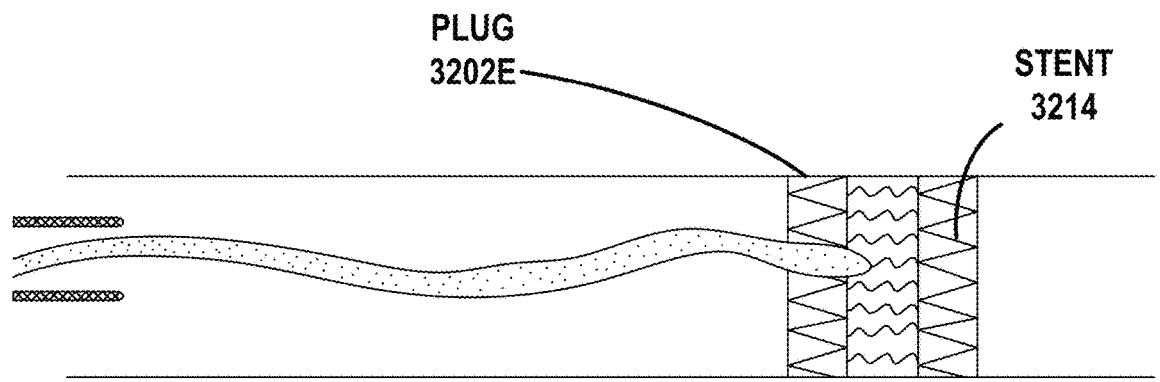

As shown in FIG. 32D, plug 3202D includes a braided "anchoring" stent having a distal fluid-tight covering 3212 configured to occlude blood flow or the flow of other fluids (e.g., chemical agent 208 or other drugs) delivered to target vessel 202. By comparison, plug 3202E of FIG. 32E includes a position-securement stent without having a distal cover, thereby permitting at least some fluid flow through the stent. Stent 3214 can be used for temporary fixation, e.g., to anchor another component of ablation system 100, such as one of the balloons described throughout this disclosure, in place during the ablation treatment.

Figure 32F:
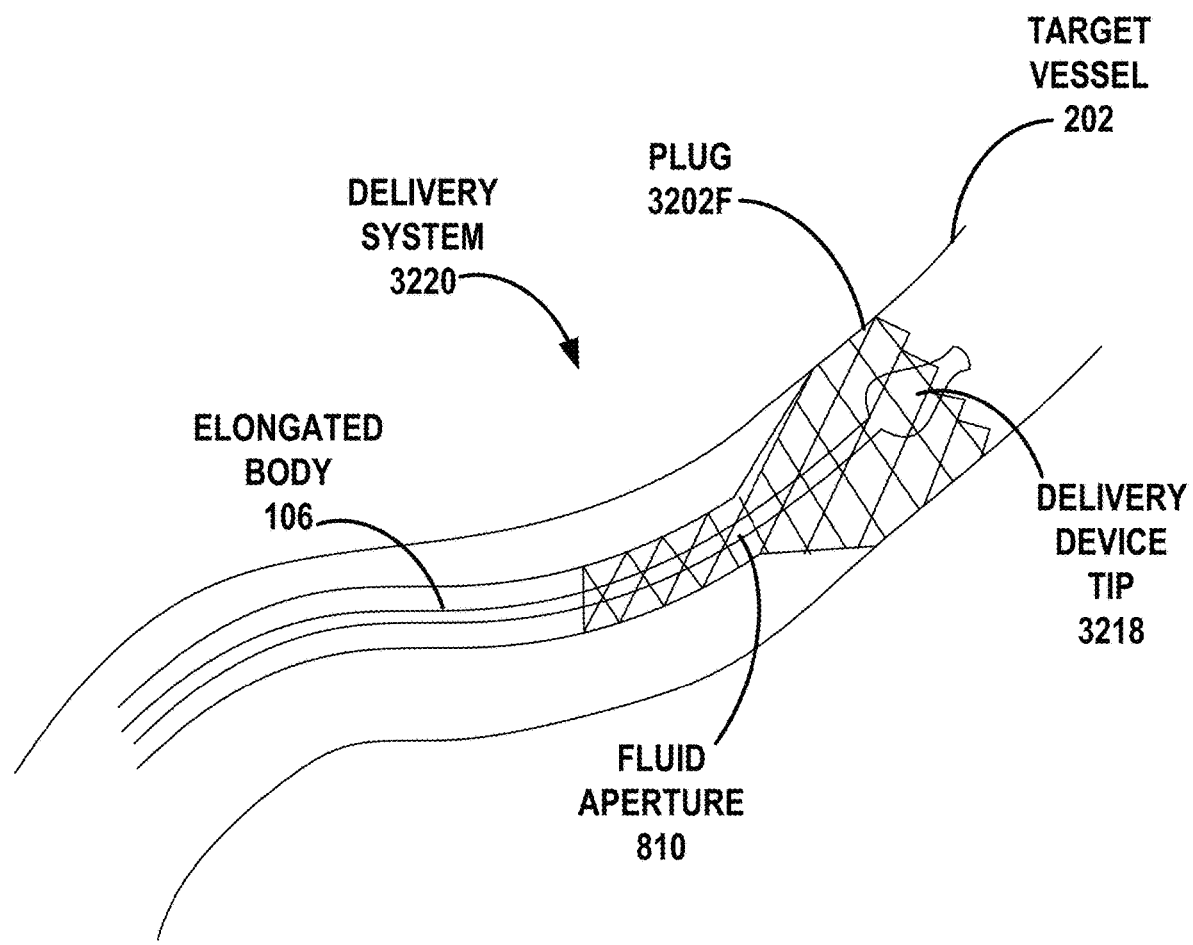

FIG. 32F shows a delivery system 3220 for a self-expanding, stent-like plug 3202F. Delivery system 3220 includes a delivery-device tip 3218 (e.g., ablation device 114 of FIG. 1) at a distal portion of elongated body 106. Elongated body 106 defines at least one fluid aperture 810 for infusing a chemical agent 208 such as an occlusion fluid, a sclerosant fluid, or both. For instance, after initial occlusion by plug 3202F, an occlusion fluid (i.e., gel, cyanoacrylate, foam, etc.) may be infused into the target vessel 202 via aperture 810 to further support vessel occlusion.

Figure 32G:
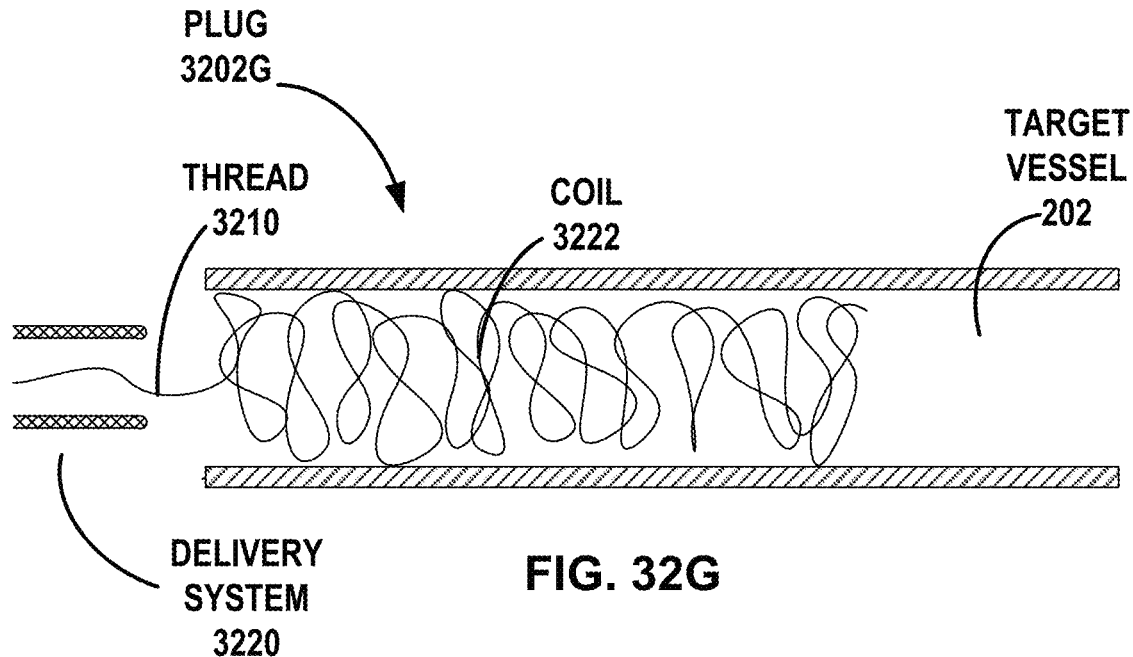
Figure 32H:
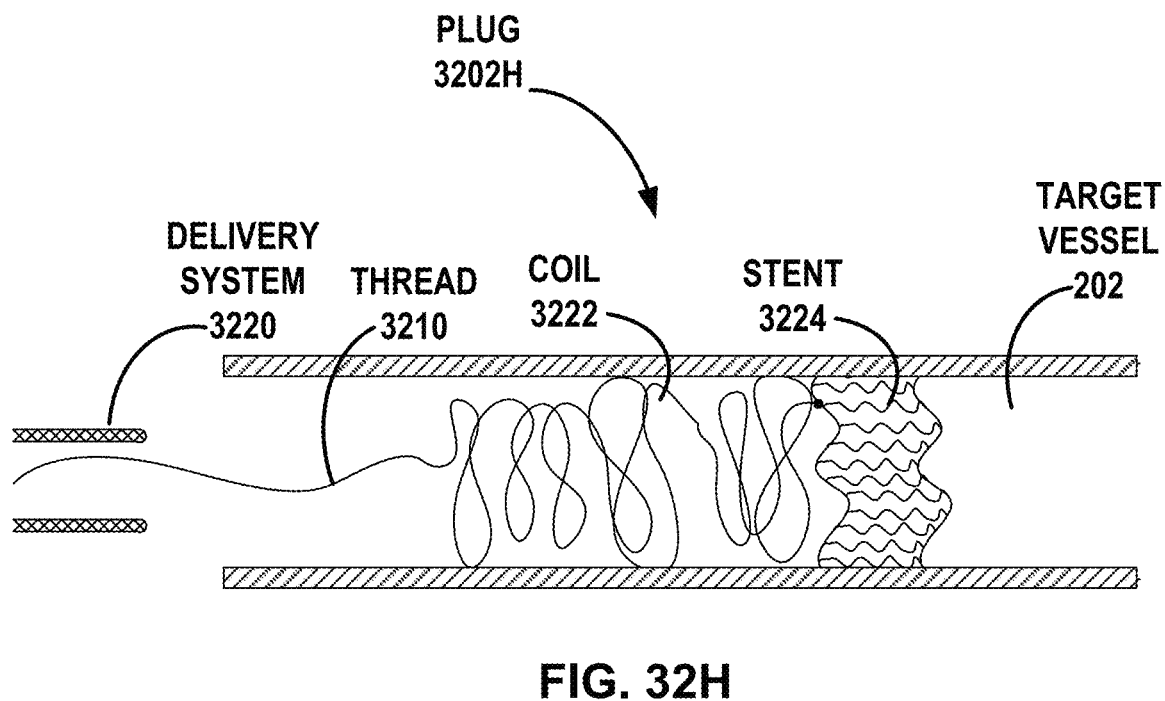

FIGS. 32G and 32H illustrate example plugs 3202G, 3202H, respectively, having coiled structures 3222, as referenced above with respect to FIG. 32C. In both FIGS. 32G and 32H, a bioresorbable-coil 3222 is shown pushing against the inner wall of target vessel 202. Plug 3202H of FIG. 32H includes an additional stent 3224 for use in conjunction with the coils 3222, which may facilitate securement of the coils 3222 within target vessel 202 and/or occlusion of target vessel 202.

Additionally or alternatively to infusing cyanoacrylate, the clinician may infuse a hydroscopic Polyvinylpyrrolidone (PVP) to absorb water in the blood and swell to fill or occlude the target vessel 202. PVP can be crosslinked with Sodium Hydroxide (NaOH) to form a more resilient gel, mixed with a sclerosant, or mixed with fibrinogen concentrate to promote blood clotting. Other potential fillers include hyaluronic acid (which is naturally produced by human bodies and is already found in skin and cartilage), calcium hydroxyapatite (which is found in human bones), Poly-L-lactic acid (which is a biodegradable synthetic material used to make other medical products, such as dissolvable stitches), and polymethylmethacrylate beads (generally only used around the mouth). Fillers made with hyaluronic acid generally last between six and twelve months. Fillers made with calcium hydroxyapatite generally last up to eighteen months. Fillers made from Poly-L-lactic acid generally last up to two years. Fillers made from Polymethylmethacrylate beads cannot be absorbed by the human body, and thus, results are generally permanent.

Figure 33A:
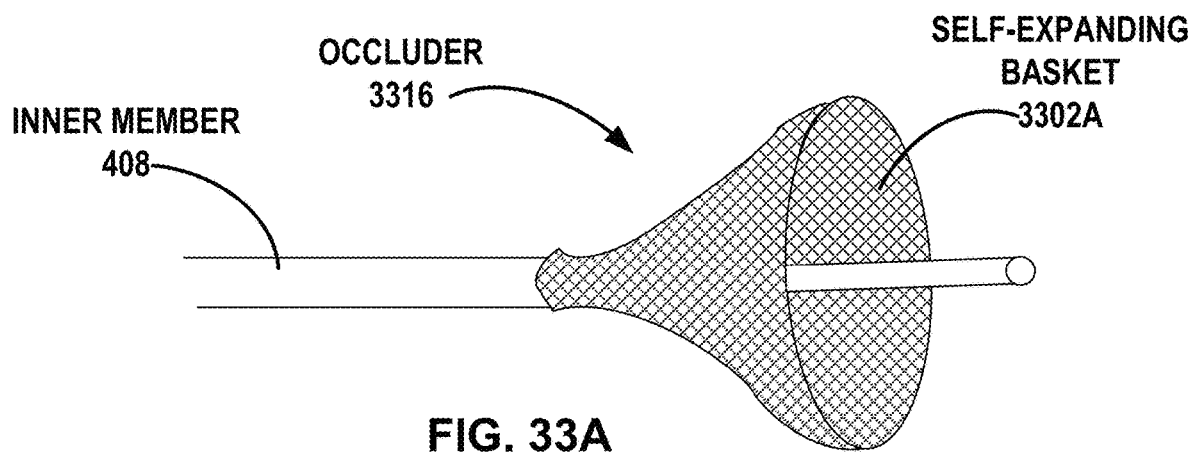
FIGS. 33A-33C are conceptual diagrams of self-expanding vessel occluders for the ablation system of FIG. 1.
Figure 33B:
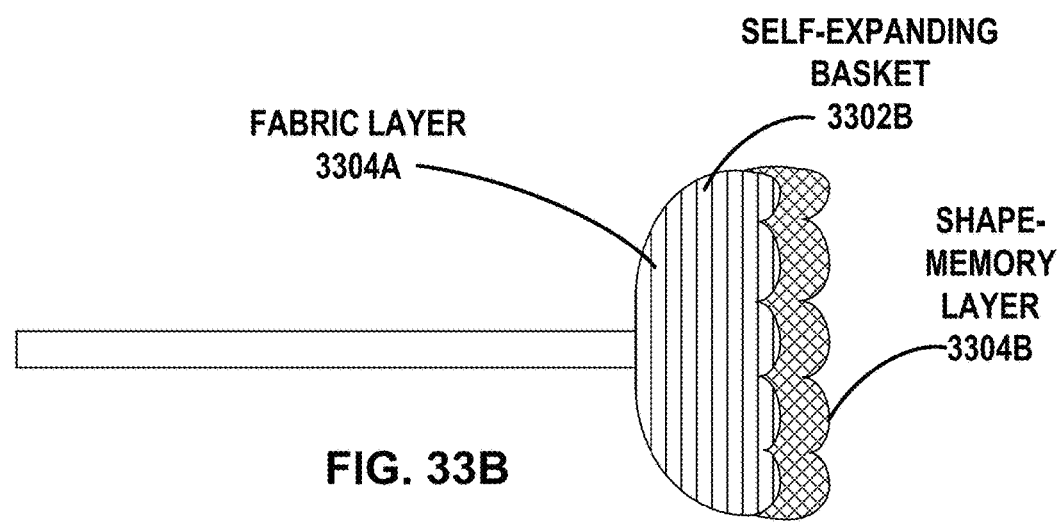
Figure 33C:
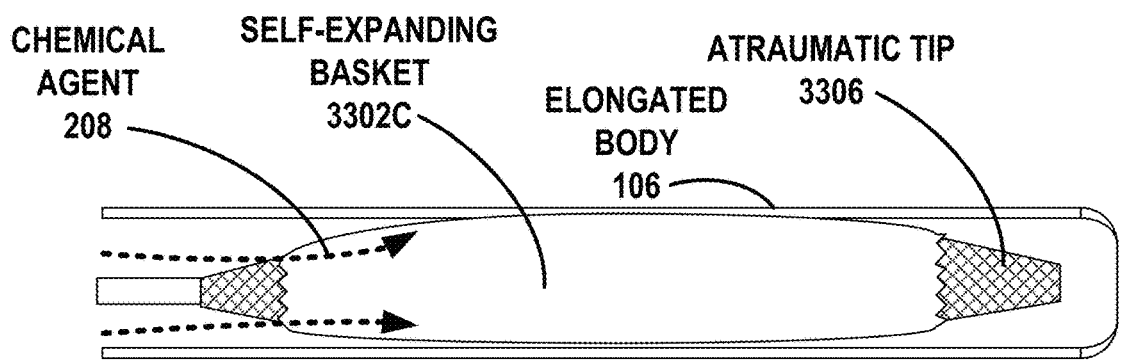

FIGS. 33A-33C are conceptual diagrams of vessel occluder 3316 (e.g., vessel occluder 216 of FIG. 2) having a self-expanding basket 3302A-3302C, respectively, configured to self-expand radially outward to retain chemical agent 208 within target vessel 202. In some examples, self-expanding basket 3302A includes a Nitinol "skirt" and shroud, a self-expanding braid or cut tubing, or a balloon. In some examples, self-expanding basket 3302A is coupled to inner member 408, such as a stiff deployment wire or cable within the inner lumen 210. In some examples, but not all examples, the self-expanding baskets 3302A-3302C are configured to rotate about longitudinal axis 214 to perform mechanical agitation.

In the example shown in FIGS. 33B and 33C, self-expanding baskets 3302B, 3302C include an outer fabric layer 3304A positioned overtop an inner shape-memory-material layer 3304B. In some such examples, a distal tip 3306 of inner member 408 may be atraumatic (e.g., rounded and/or formed from a compliant material). During use, the clinician infuses chemical agent 208 through the inner lumen 210 of catheter 102 to wet the fabric of self-expanding basket 3302C while self-expanding basket 3302C is sheathed within inner lumen 210. The clinician may then either retract elongated body 106, advance inner member 408, or both, to deploy the self-expanding basket 3302C from distal catheter mouth 510 and occlude target vessel 202. Subsequently, the clinician may advance elongated body 106 distally forward, proximally retract inner member 408, or both, to retrieve the self-expanding basket 3302B, 3302C, e.g., to "re-wet" the fabric of the self-expanding basket 3302B, 3302C with chemical agent 208.

Figure 34A:
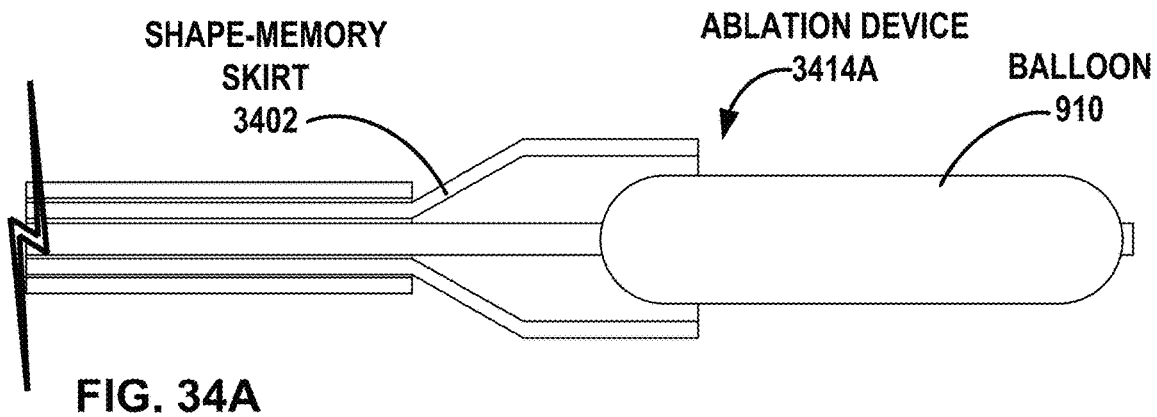
FIGS. 34A-34F are conceptual diagrams of six examples of the ablation device of FIG. 1 having weeping-balloon mechanisms.

FIGS. 34A-34F are conceptual diagrams of seven example ablation devices 3414A-3414F (e.g., ablation device 114 of FIG. 1), each having a respective weeping balloon (e.g., weeping balloon 910 of FIGS. 9C and 9D). For instance, FIG. 34A illustrates an example ablation device 3414A having a shape-memory-material (e.g., Nitinol) "skirt" 3402 positioned proximal to weeping balloon 910. Shape-memory skirt 3402 may be an example of self-expanding basket 3302A of FIG. 33A.

Figure 34B:
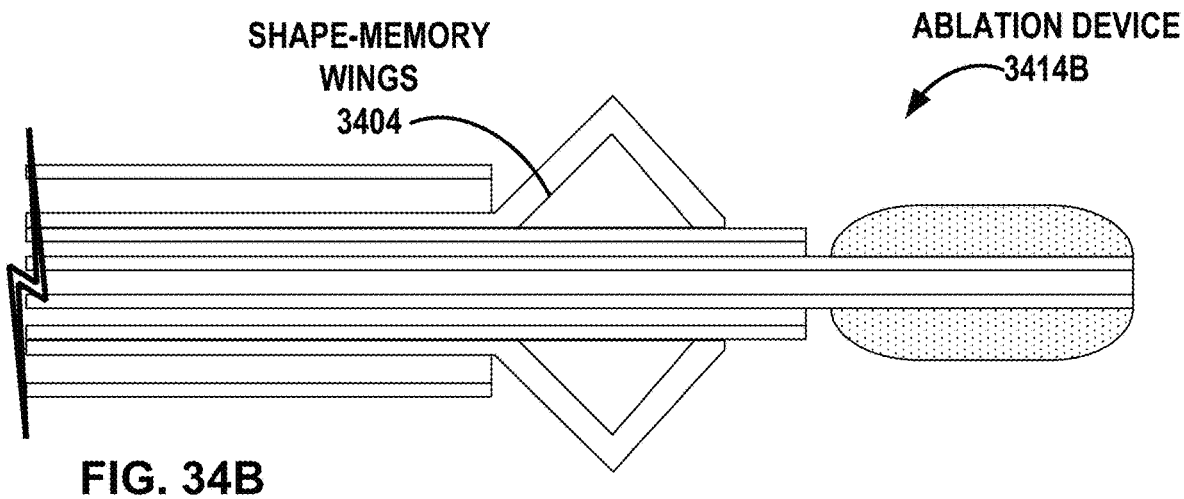

FIG. 34B illustrates an example ablation device 3414B having a radially expanding shape-memory-material occluder 3304 positioned proximal to weeping balloon 910. Shape-memory occluder 3304 may function similar to catheter wings 2502A of FIG. 25A.

Figure 34C:
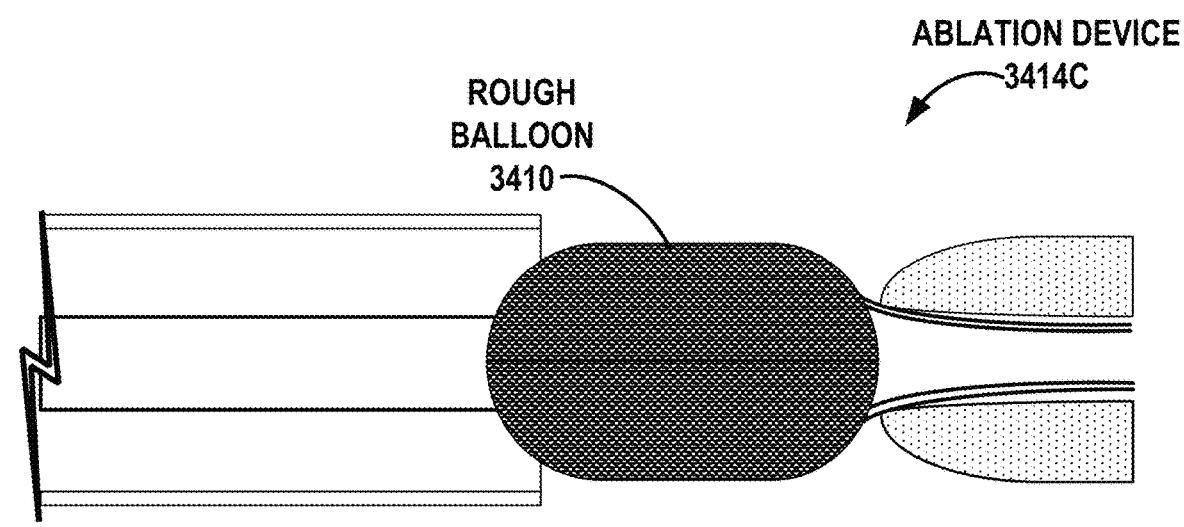

FIG. 34C illustrates an example ablation device 3414C in which an exterior surface of weeping balloon 3410 includes a substantially rough or "spiked" texture configured to both abrade the vessel wall and help retain balloon 910 in place via friction.

Figure 34D:
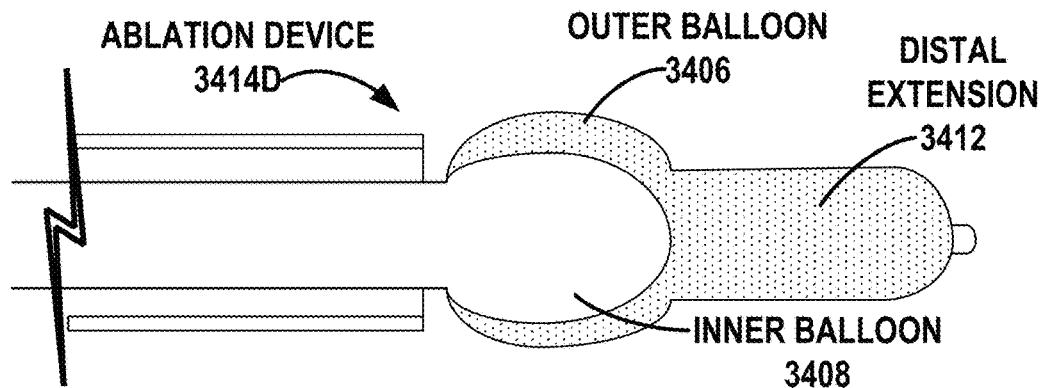

FIG. 34D illustrates an example ablation device 3414D with double-nested weeping balloons 3406, 3408. Outer balloon 3406 includes a distal extension 3412 having a rough or spiked (or "diamond grip") texture, as described above with respect to FIG. 34C.

Figure 34E:
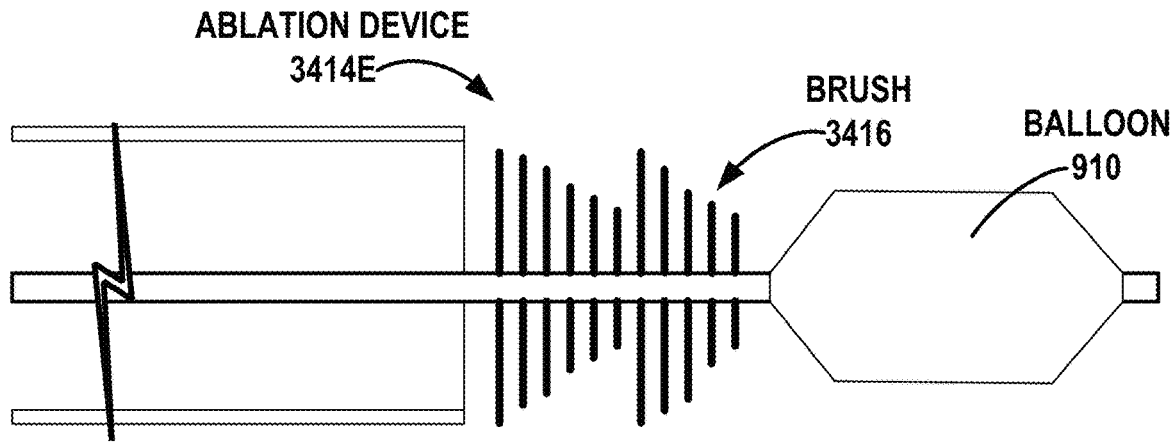

FIG. 34E illustrates an example ablation device 3414E having a proximal brush 3416 (e.g., agitator 204 of FIG. 2), which may be an example of brushes 2602A-2602C of FIGS. 26A-26C.

Figure 34F:
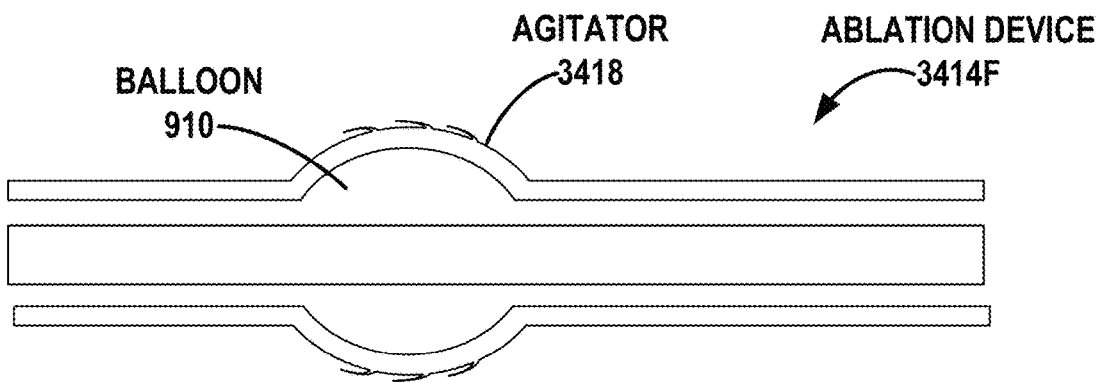

FIG. 34F illustrates an example ablation device 3414F having a balloon-expandable agitator 3418 (e.g., agitator 204 of FIG. 2). Agitator 3418 defines an exterior surface having a cheese-grater-type mechanism, e.g., a plurality of radially misaligned convex and concave portions defining vessel-abrading edges therebetween.

Figure 35A:
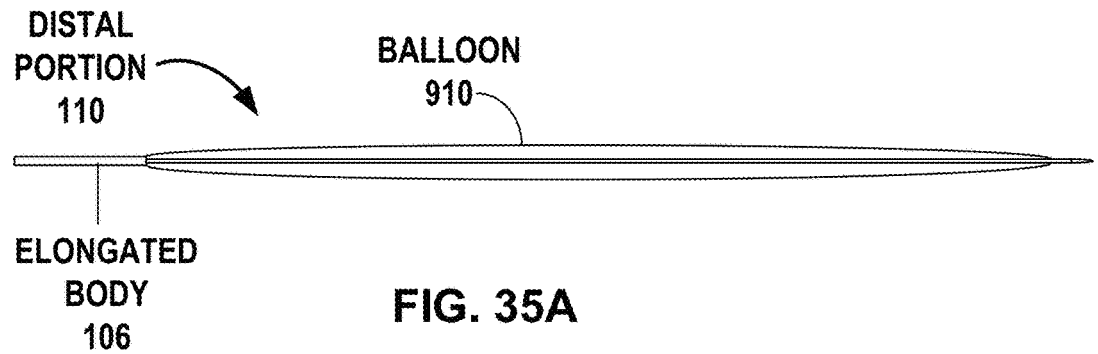
FIGS. 35A-35C are conceptual diagrams illustrating functionality of a weeping balloon mechanism for the ablation system of FIG. 1.
Figure 35B:
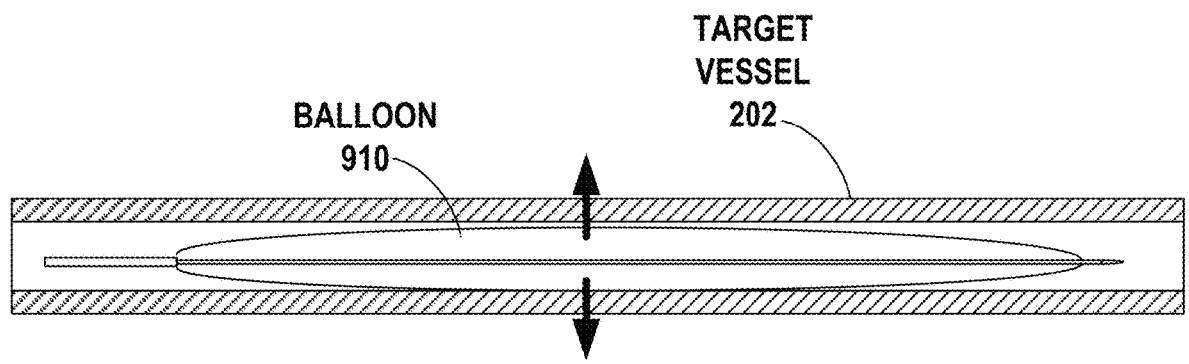
Figure 35C:
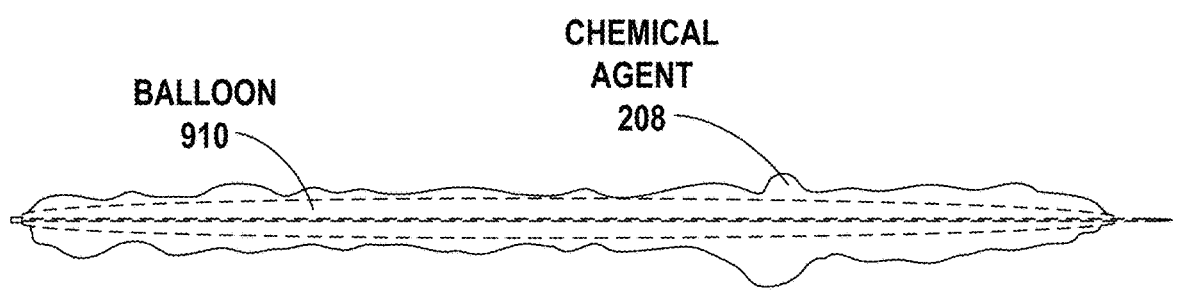

FIGS. 35A-35C are conceptual diagrams illustrating the functionality of weeping balloon 910 of FIGS. 9C and 9D. For instance, FIG. 35A illustrates weeping balloon 910 in its initial, uninflated configuration. As shown in FIG. 35B, during use, the clinician may use a fluid, such as chemical agent 208, to at least partially inflate balloon 910 within target vessel 202. As shown in FIG. 35C, over time, the fluid begins to weep or seep out from the microscopic pores defined by the surface of the balloon. In particular, FIG. 35C illustrates chemical agent 208 having a foaming property, configured to weep through the balloon pores and cover the exterior surface of the balloon. In some such examples, the clinician can manually generate this foam, e.g., by actuating a $CO_2$ mini-cartridge within control device 112. In some examples, this foam can include a "cold" foam configured to ablate target vessel 202 via cryotherapy. In some examples, the foam can be "stabilized" through injection by air, carbon dioxide, nitrogen, or argon to extend the lifespan of the foam and accordingly, sclerosant uptake.

In some examples, weeping balloon 910 can be configured to simultaneously perform three different functions: fluid infusion, via pores of the balloon; vessel occlusion, when pressurized and expanded against the target vessel wall; and mechanical vessel agitation. For instance, as referenced above, e.g., with respect to FIGS. 34C and 34F, an outer surface or outer layer of balloon 910 can include an abrading element, such as a rough surface or cheese-grater-type mechanism.

In some examples, weeping balloon 910 may be semi-porous, permitting the inflation fluid to slowly perfuse directly into the wall of target vessel 202 while weeping balloon 910 inflates. This would also allow the inflation fluid to exit along the entire longitudinal length of the weeping balloon 910 (as compared to just a proximal portion), thereby increasing the area of treatment. In some examples, the internal fluid pressure within weeping balloon 910 reduces or prevents the inflation fluid from "washing out" of target vessel 202. In such examples, weeping balloon 910 may perform the occlusive functionality of vessel occluder 216 of FIG. 2. In some examples, weeping balloon 910 may be at least partially formed from an ethylene tetrafluoroethylene (ETFE) sleeve.

FIGS. 36A-36D are conceptual diagrams illustrating four example weeping balloons 3610A-3610D (e.g., weeping balloon 910 of FIGS. 9C and 9D), respectively.

Figure 36A:
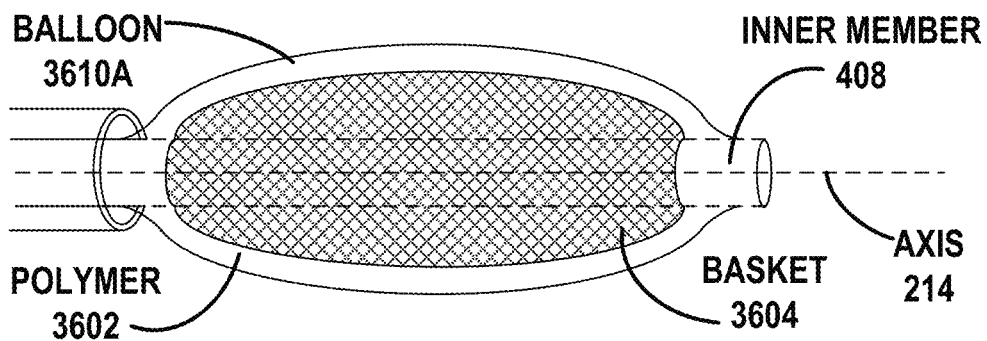
FIGS. 36A-36D are conceptual diagrams of four example interventional balloons for the ablation system of FIG. 1

FIG. 36A illustrates weeping balloon 3610A. Weeping balloon 3610A comprises a polymer substrate 3602 (e.g., Pellethane™) coupled to a shape-memory-material basket 3604 (e.g., Nitinol). Basket 3604 may be coupled to either an exterior surface or the interior surface of the substrate, and is configured to cause balloon 3610A to self-expand radially outward, e.g., when advanced outward from distal catheter mouth 510.

Figure 36B:
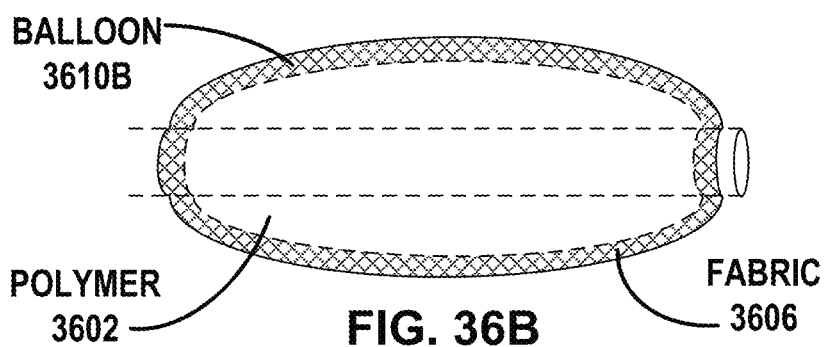

FIG. 36B illustrates weeping balloon 3610B. Weeping balloon 3610B comprises a polymer substrate 3602 disposed within a fabric sheath 3606, such as Nylon. Fabric sheath 3606 defines a plurality of weep holes configured to release chemical agent 208 into the surrounding tissue.

Figure 36C:
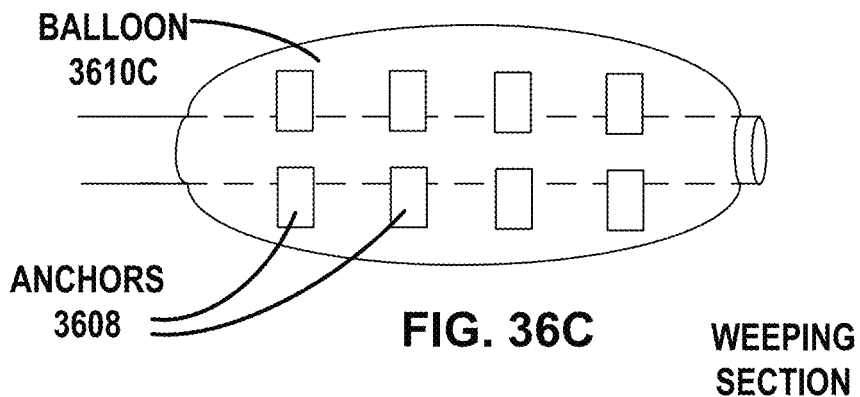

FIG. 36C illustrates weeping balloon 3610C. Weeping balloon 3610C comprises a plurality of molded anchors 3608. Molded anchors 3608 are configured to engage with the vessel wall to help retain balloon 3610C in place within target vessel 202. Anchors 3608 can include any high-friction shape and/or composition, such as polymer, fabric, or metal hooks.

Figure 36D:
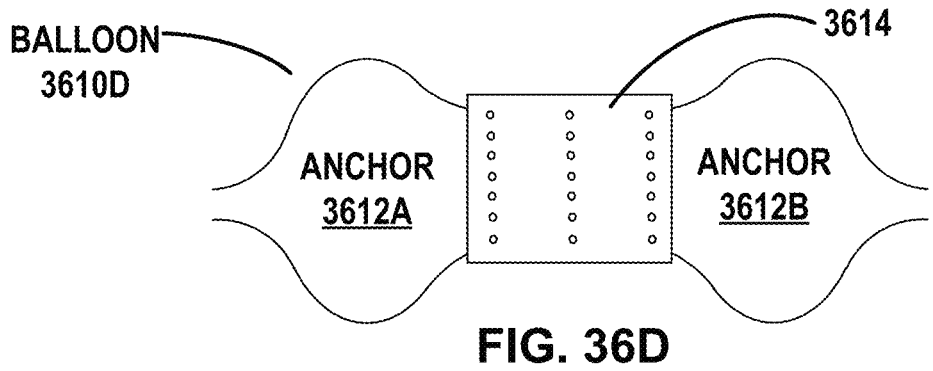

FIG. 36D illustrates weeping balloon 3610D. Weeping balloon 3610D is an example of ablation device 2214 of FIG. 22. That is, weeping balloon 3610D includes a pair of proximal and distal compliant (e.g., flexible) anchorings 3612A, 3612B (e.g., balloons 2202A, 2202B of FIG. 22), with a semi-compliant (e.g., less-flexible) weeping section 3614 therebetween. In another example, proximal and distal anchorings 3612 are formed from a polymer (e.g., Pellethane™), and weeping section 3614 may be formed from a fabric (e.g., Nylon).

Figure 37:
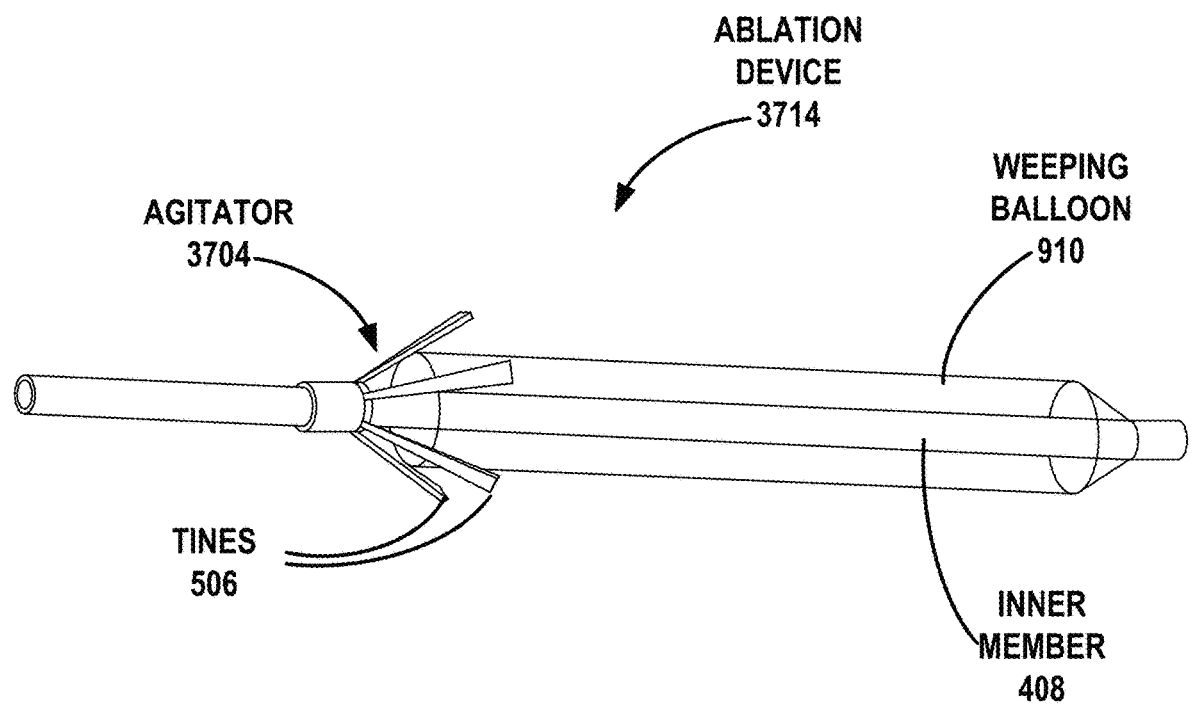
FIG. 37 is a conceptual diagram of an example ablation device of FIG. 1 having a mechanical agitator configured to be radially expanded by an interventional balloon.

FIG. 37 is a profile view of an ablation device 3714 (e.g., ablation device 114 of FIG. 1). As shown in FIG. 37, ablation device 3714 includes an agitator 3704 (e.g., agitator 204 of FIG. 2) having a plurality of elongated tines 506, and a weeping balloon 910. In particular, a proximal end of weeping balloon 910 is positioned radially inward from elongated tines 506, such that, when the clinician inflates balloon 910 with an inflation fluid (e.g., chemical agent 208), the inflation of balloon 910 causes elongated tines 506 to expand radially outward to contact the inner wall of target vessel 202.

Figure 38:
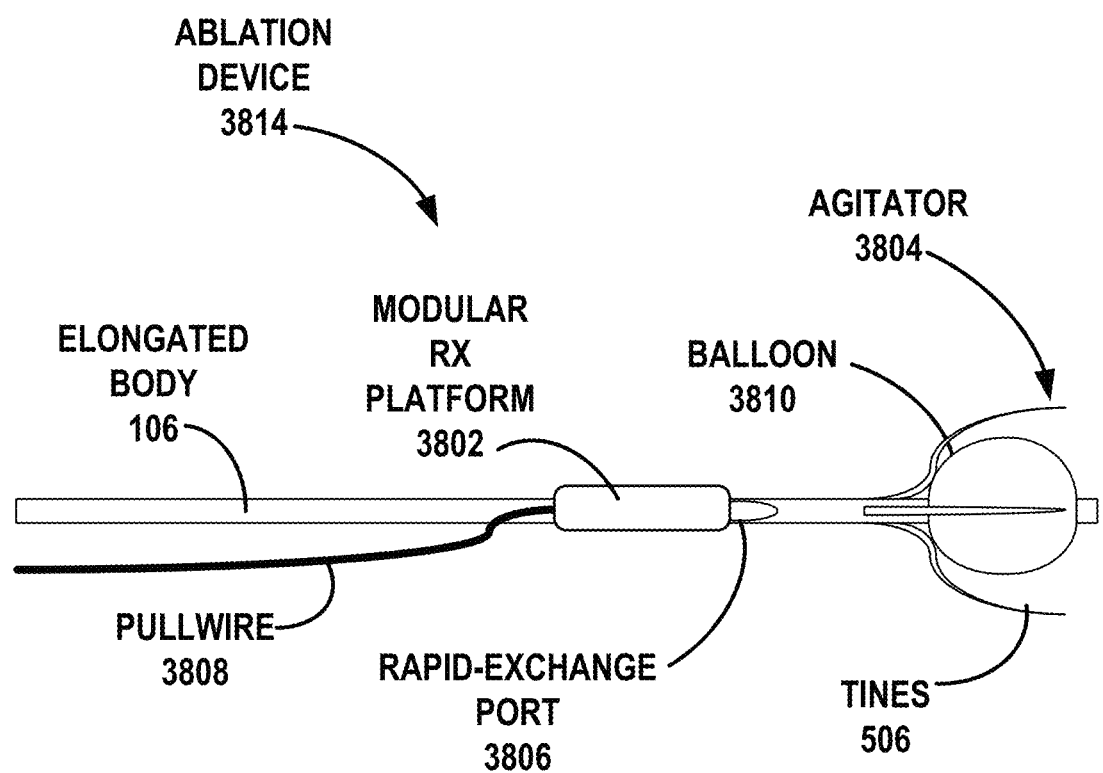
FIG. 38 is a conceptual diagram of an example of the ablation device of FIG. 1 having a modular rapid-exchange (RX) platform.

FIG. 38 is a conceptual diagram of an ablation device 3814 (e.g., ablation device 114 of FIG. 1) having an agitator 3804 (e.g., agitator 204 of FIG. 2) and a compliant distal balloon 3810. A size (e.g., an amount of inflation) of balloon 3810 can be adjusted to a level of encountered resistance between elongated tines 506 and the vessel wall. For instance, if excessive resistance is encountered, balloon 3810 can be at least partially deflated to allow elongated tine to at least partially contract radially inward. After treatment, balloon 3810 may be deflated and withdrawn from the patient's vasculature.

As shown in FIG. 38, the proximal ends of elongated tines 506 are rigidly coupled to elongated body 106 are fixated on the catheter. Prior to inflation of balloon 3810, the distal ends of elongated tines may be encapsulated via a membrane or other retainer device, as described above with respect to FIGS. 9A-9D. Elongated tines 506 can be formed from metal or plastic, and are not coupled to balloon 3810. Similar to the example of FIG. 37, elongated tines 506 expand radially outward toward the wall of the target vessel 202 upon inflation of balloon 3810.

In some examples, catheter 102 includes a dual-lumen design, as described above with respect to FIG. 4B, enabling direct infusion of chemical agent 208. One or more fluid apertures to release chemical agent 208 may be positioned just proximal to balloon 3810. For instance, after preparing (e.g., abrading) target vessel 202 (FIG. 2), the clinician may infuse chemical agent 208. In other examples, the clinician may infuse chemical agent 208 simultaneously with abrading target vessel 202.

FIG. 38 further illustrates the use of a modular rapid-exchange ("RX") platform 3802, which itself may include an inflatable balloon. In general, RX platform 3802 enables the user to modify a size of an RX port 3806, e.g., via pullwire 3808. RX port 3806 (or "single-operator exchange") enables management of the guidewire (not shown) by the operating clinician local to the access site, rather than by a separate surgical technician positioned proximal to the ablation system.

Modular RX platform 3802 is configured to prepare certain lesions, as appropriate. Modular RX platform 3802 may be pre-loaded based on specific clinical needs. For instance, for relatively easy-to-treat vessels, modular RX platform 3802 may not be necessary. For more difficult applications, modular RX platform 3802 may be incorporated into ablation device 3814.

As a first non-limiting, illustrative example, the modular RX platform 3802 can include a short-length balloon with a scoring wire (e.g., elongated tines 506), and/or a sandpaper-like surface texture, as described above with respect to FIG. 34C. In a second example, the modular RX platform 3802 can include a short-length balloon with a high pressure to break through tougher lesions. In a third example, the modular RX platform 3802 can include a short-length balloon that incorporates both the scoring features and the high-pressure features. This short-length balloon may effectively treat tortuous anatomy, because the "straightening effect" exhibited by longer balloons is reduced, and RX platform 3802 would enable the balloon to be proximally retracted in a controlled manner, while the compliant distal balloon 3810 serves as an anchor and provides the necessary sealing function throughout the process.

Figure 39A:
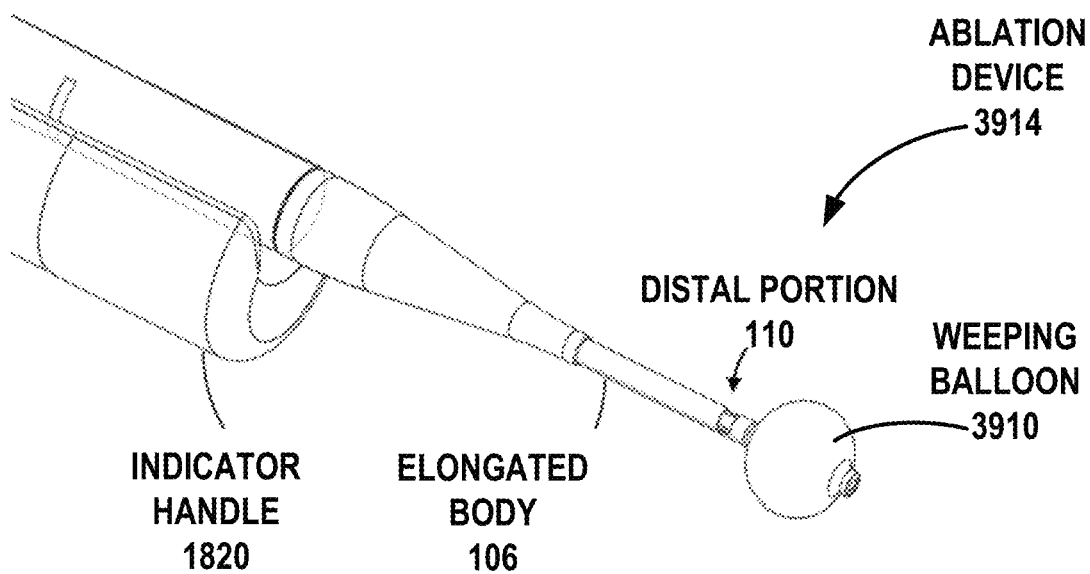
FIGS. 39A and 39B are profile views of an example of the ablation device of FIG. 1 having a distal interventional balloon.
Figure 39B:
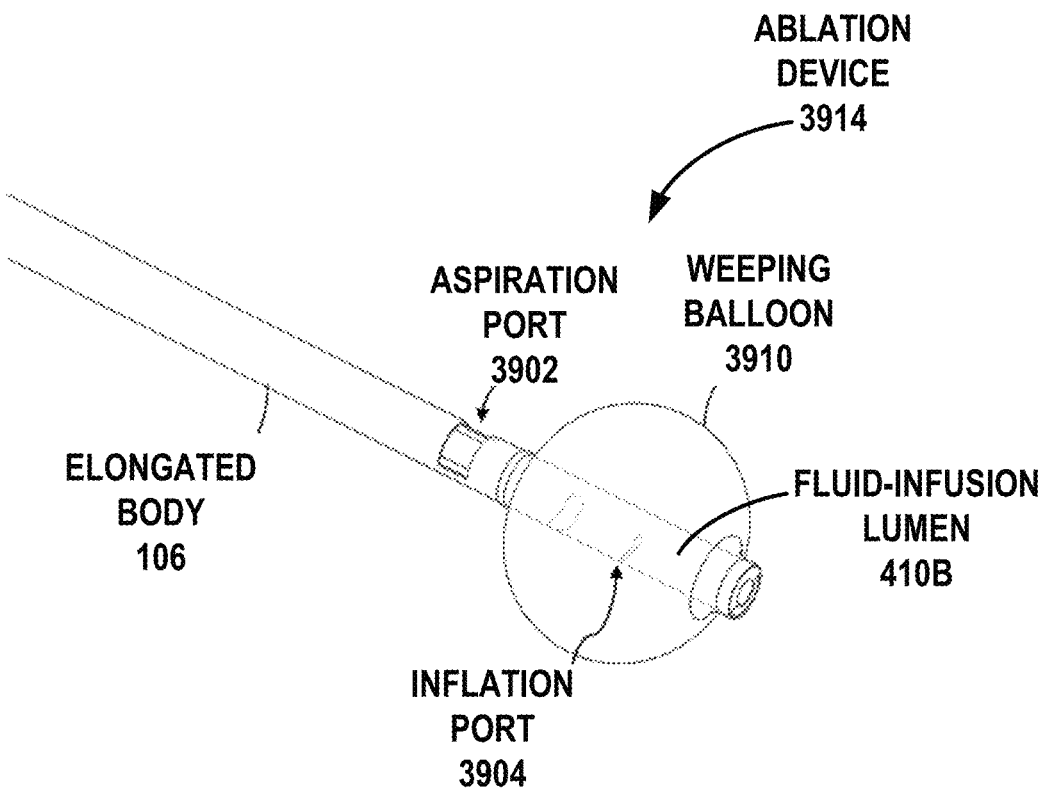

FIGS. 39A and 39B are profile views of an example ablation device 3914 (e.g., ablation device 114 of FIG. 1) having a distal interventional balloon 3910. Distal balloon 3910 is an example of weeping balloon 910 of FIGS. 9C and 9D, except for the differences noted herein. Specifically, as illustrated in FIGS. 39A and 39B, balloon 3910 defines a more-spherical shape, as compared to the more-elongated shape shown in FIGS. 9C and 9D.

As illustrated in FIGS. 39A and 39B, a distal portion of elongated body 106 defines a fluid-aspiration port 3902. During use, the clinician may use fluid-aspiration port 3902 to evacuate a volume of the patient's blood simultaneously with the infusion of chemical agent 208 to the target vessel 202. As described above with respect to FIG. 4C, a tri-lumen elongated body 106 may be used to employ a guidewire, fluid infusion, and fluid aspiration. Because there is less blood present in the target vessel 202 after being evacuated, the chemical agent 208 infused into the target vessel 202 will be less diluted. Accordingly, in such examples, less chemical agent 208 may be needed for effective vessel ablation. In some examples, a vacuum may be applied to the distal end of elongated body 106 to hold chemical agent 208 in place.

As shown in FIG. 39B, elongated body 106 defines fluid-infusion lumen 410B running through the length of elongated body 106. Fluid-infusion lumen 410B may be configured to deliver chemical agent 208 to the target vessel 202. The distal portion 110 of elongated body 106 defines at least one opening enabling chemical agent 208 to exit fluid-infusion lumen 410B. In the example of FIG. 39B, fluid-infusion lumen 410B opens into weeping balloon 3910 via fluid-inflation port 3904, allowing the fluid to inflate balloon 3910.

Figure 40A:
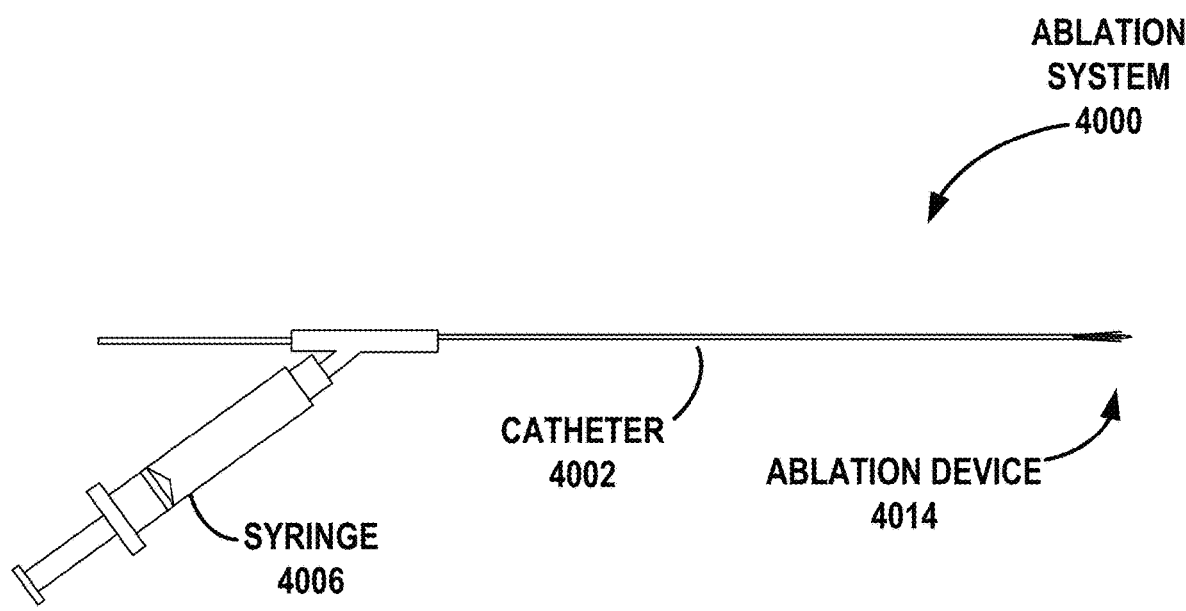
FIGS. 40A and 40B are conceptual diagrams of an example of the ablation system of FIG. 1 having a distal interventional balloon disposed within a mechanical agitator.
Figure 40B:
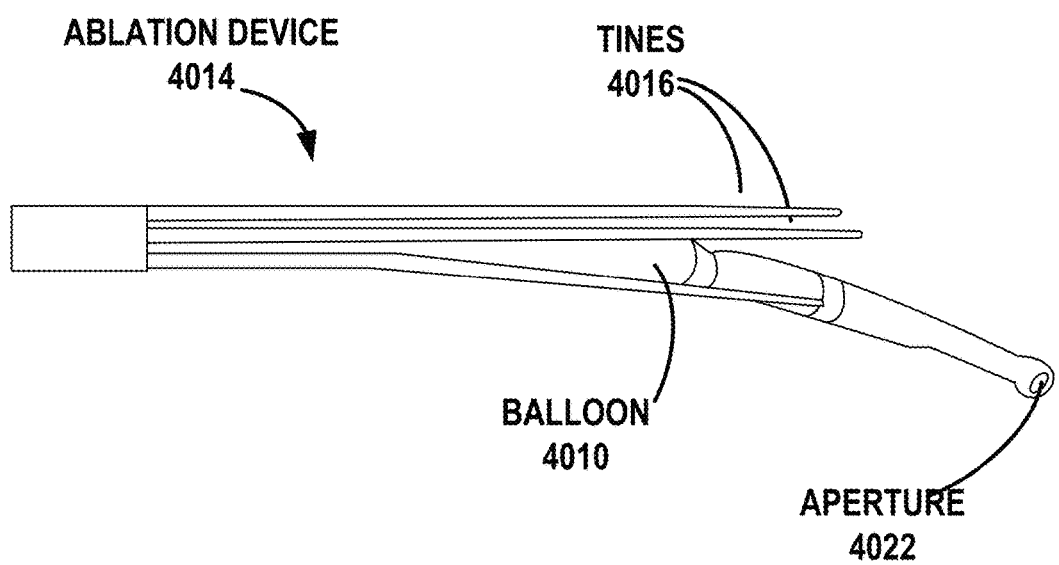

FIGS. 40A and 40B are conceptual diagrams of an example prototype ablation system 4000 (e.g., ablation system 100 of FIG. 1). As shown in FIG. 40A, ablation system 4000 includes a catheter 4002 (e.g., catheter 102), a proximal syringe 4006 (e.g., fluid reservoir 206 of FIG. 2), and a distal ablation device 4014 (e.g., ablation device 114). As shown in FIG. 40B, ablation device 4014 includes an agitator having a plurality of elongated tines 4016 (e.g., tines 506 of FIG. 5), and a balloon 4010 disposed at least partially radially inward from tines 4016. Balloon 4010 is configured to be inflated to cause tines 4016 to expand radially outward, and pressurized to increase the contact force between tines 4016 and the vessel wall.

A distal end of catheter 4002 defines at least one aperture 4022 configured to infuse a sclerosant into the target vessel 202. The sclerosant may be used both to inflate and pressurize balloon 4010, as well as to chemically ablate the target vessel 202. In some examples, catheter 4002 may define multiple apertures 4022 of different sizes (e.g., diameters), forming a differential pressure within balloon 4010 prior to vessel infusion.

Figure 41A:
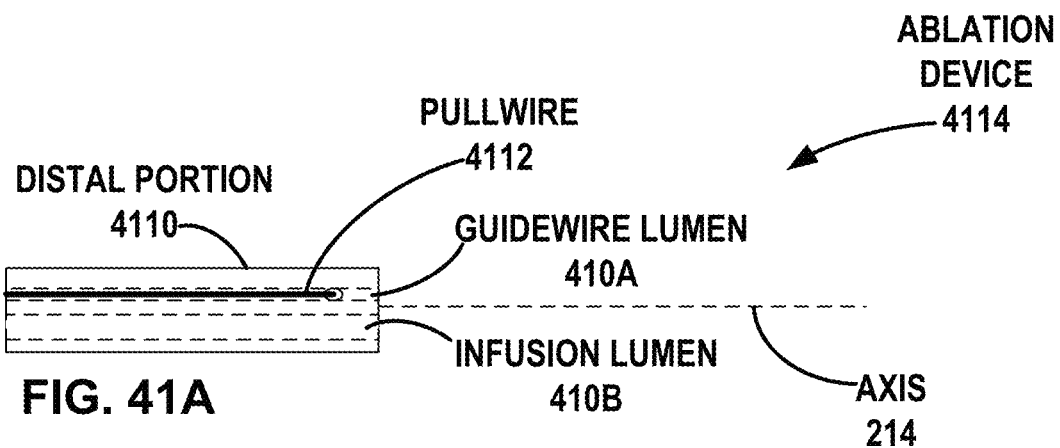
FIGS. 41A-41D illustrate an example of the catheter of FIG. 1 having a steerable distal portion.

FIGS. 41A-41D illustrate four examples of a "steerable" ablation device 4114 (e.g., ablation device 114 of FIG. 1). In particular, ablation device 4114 includes a steerable distal portion 4110 (e.g., distal portion 110 of FIG. 1) of elongated body 106. FIG. 41A illustrates distal portion 4110 in a linear configuration, e.g., conforming substantially to longitudinal axis 214. As described above with respect to FIG. 4B, distal portion 4110 defines guidewire lumen 410A and fluid-infusion lumen 410B.

Figure 41B:
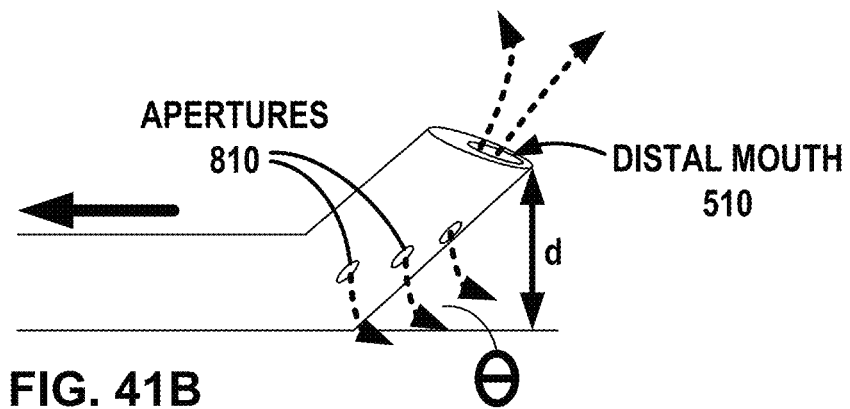
Figure 41C:
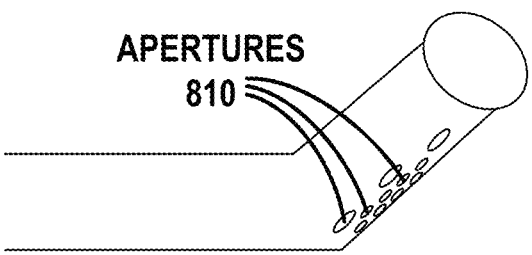
Figure 41D:
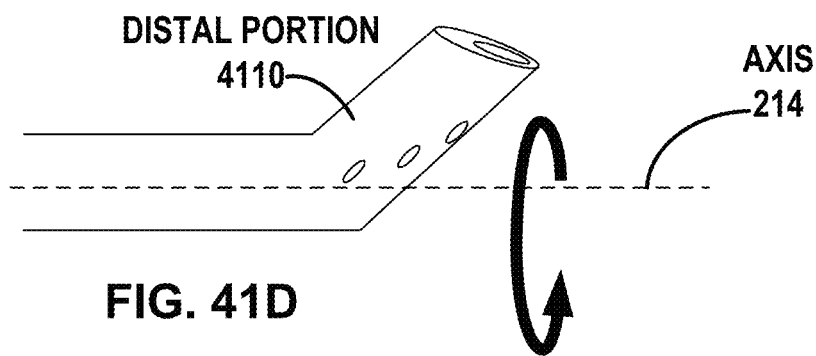

As illustrated in FIG. 41B, the clinician may actuate a pullwire 4112, e.g., positioned within guidewire lumen 410A, to deflect distal portion 4110 away from longitudinal axis 214 by a variable angle θ, as appropriate. As further shown in FIG. 41B, distal portion 4110 is configured to optionally infuse chemical agent 208, via fluid-infusion lumen 410B, from distal catheter mouth 510. Additionally or alternatively, the exterior surface of distal portion 4110 defines a plurality of fluid apertures 810 of varying size and/or arrangement, enabling the user to optionally infuse chemical agent 208 via apertures 2204. Finally, as shown in FIG. 41D, the clinician may actuate user control 212 to cause distal portion 4110 to rotate about longitudinal axis 214, thereby dispersing chemical agent 208 around the interior surface of vessel wall.

Figure 42A:
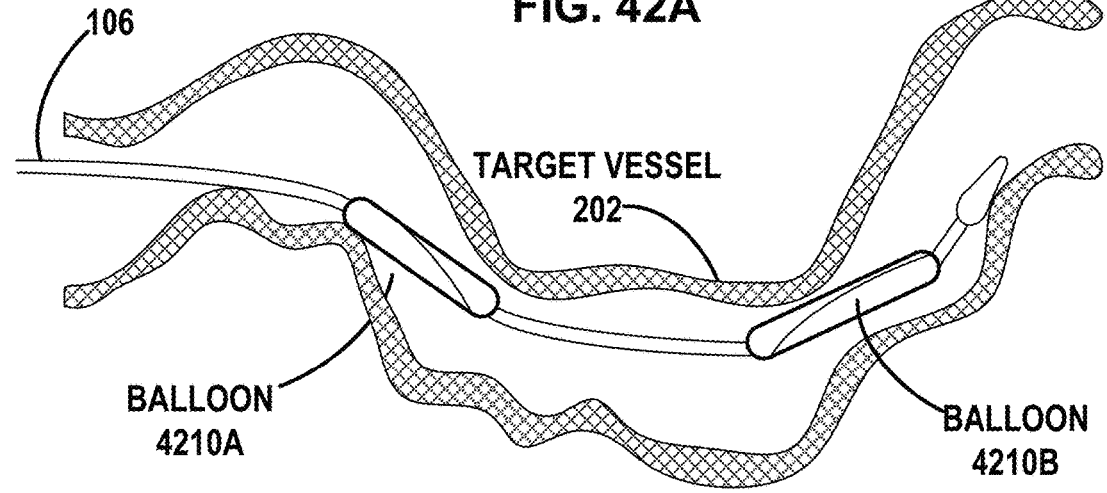
FIGS. 42A-42C are conceptual diagrams illustrating a technique for using two interventional balloon elements of an example of the ablation system of FIG. 1 to straighten a target vessel for subsequent ablation.
Figure 42B:
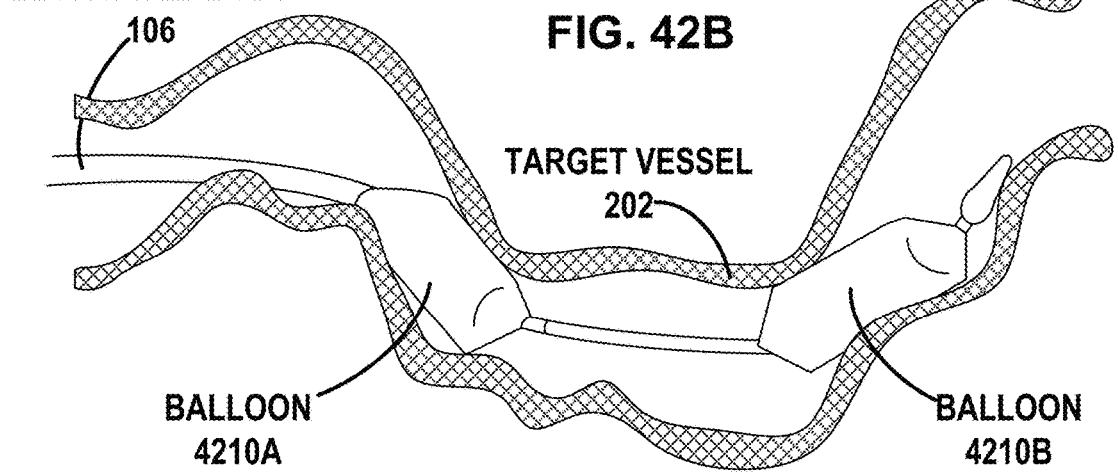
Figure 42C:
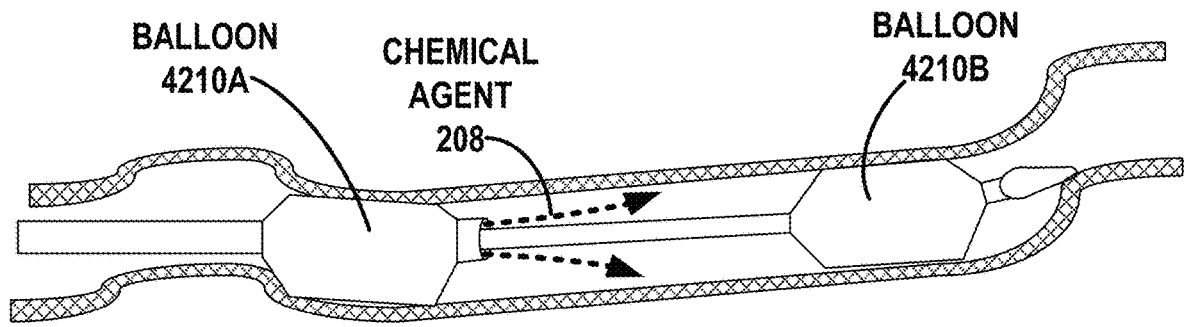

FIGS. 42A-42C are conceptual diagrams illustrating a technique for using two interventional balloons 4210A, 4210B (or other expandable structures) of ablation device 114 of FIG. 1 to straighten target vessel 202 prior to ablation. As shown in FIGS. 42A-42C, proximal and distal balloons 4210A, 4210B may be independently operated to position the balloons within the target vessel (FIG. 42A), and then inflated so as to engage with the wall of the target vessel 202 (FIG. 42B). The longitudinal positions of balloons 4210 may further be manipulated to increase the longitudinal distance between proximal and distal balloons 4210, thereby causing the vessel region between balloons 4210 to straighten and/or narrow. As shown in FIG. 42C, chemical agent 208 may then be infused into the vessel region between balloons 4210 to ablate the surrounding tissue.

In some examples, the steps of this technique may be reversed in order to longitudinally compress the vessel region between balloons 4210. In this way, the target vessel 202 may be cyclically stretched and compressed, e.g., in order to mechanically ablate the vessel obstruction or to induce a vessel spasm, as appropriate.

Figure 43:
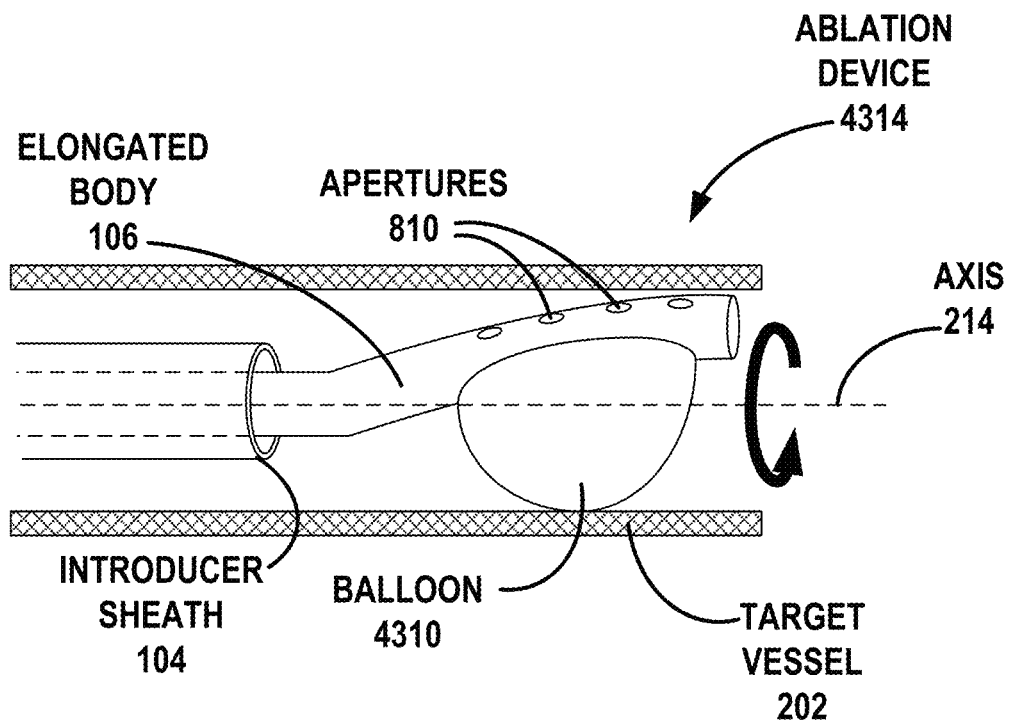
FIG. 43 is a conceptual diagram illustrating an example of the ablation device of FIG. 1 having a radially biasing balloon.

FIG. 43 is a conceptual diagram illustrating an example ablation device 4314 (e.g., ablation device 114 of FIG. 1) having a radially eccentric balloon 4310. Balloon 4310 is configured to inflate to radially offset elongated body 106 to compress fluid apertures 810 against the vessel wall for more-direct infusion of chemical agent 208.

In the example shown in FIG. 43, ablation device 4314 includes a single eccentric balloon 4310 positioned along one side of the exterior surface of elongated body 106. The opposite side of the exterior surface of elongated body 106 defines fluid apertures 810. Once the clinician has fluid-inflated balloon 4310 to compress apertures 810 near or against vessel wall, the clinician may then rotate ablation device 4314 about longitudinal axis 214 so as to infuse chemical agent 208 around the entire inner circumference of vessel wall.

In other examples, ablation device 4314 may include a plurality of independently inflatable balloons 4310, and a respective plurality of fluid apertures 810, distributed around the outer circumference of elongated body 106. During use, the clinician may selectively inflate and deflate each of the balloons 4310 to radially deflect the elongated body along different directions and treat different portions of the inner circumference of the vessel wall, e.g., in addition to, or instead of, rotating ablation device 4314.

Figure 44:
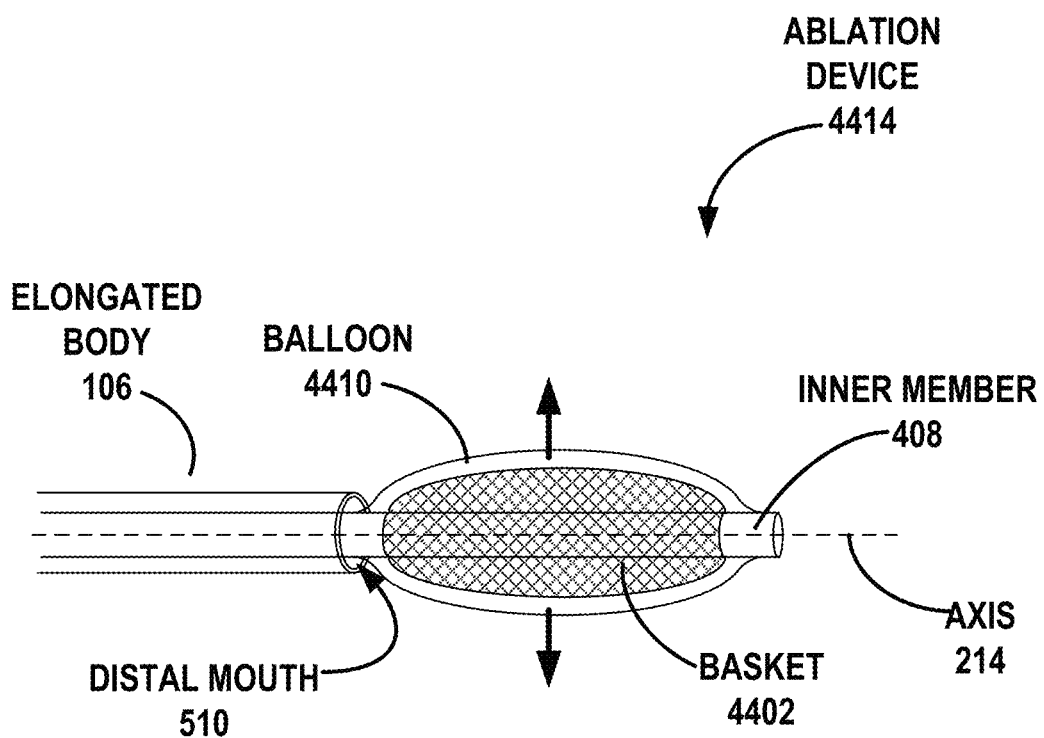
FIG. 44 is a conceptual diagram illustrating an example of the ablation device of FIG. 1 having a self-expanding balloon.

FIG. 44 is a conceptual diagram illustrating an example ablation device 4414 (e.g., ablation device 114 of FIG. 1) having a self-expanding balloon 4410. Balloon 4410 is an example of balloon 3610A of FIG. 36A. That is, balloon 4410 includes a self-expanding (e.g., shape-memory-material) basket 4402 (3604) disposed within the interior surface (3602) of the balloon 4410. In response to advancing outward from distal mouth 510 of catheter 102 (or equivalently, of introducer sheath 104), basket 4402 is configured to automatically assume its previously set shape, causing balloon 4410 to expand radially outward without requiring separate inflation, e.g., fluid-inflation.

In examples in which balloon 4410 comprises a porous or semi-porous balloon (e.g., weeping balloon 910 of FIGS. 9C and 9D), chemical agent 208 may be injected through fluid-infusion lumen 410B (FIG. 4B) and into balloon 4410 for subsequent vessel infusion. Such examples may help control a precise amount and/or rate of chemical agent 208 infused into vessel wall.

In examples in which balloon 4410 includes a non-porous balloon, chemical agent 208 can be infused from distal catheter mouth 510 and then "wicked" around the exterior surface of balloon 4410. Such examples may help reduce or prevent excess chemical agent 208 from traveling "upstream" past balloon 4410.

Figure 45A:
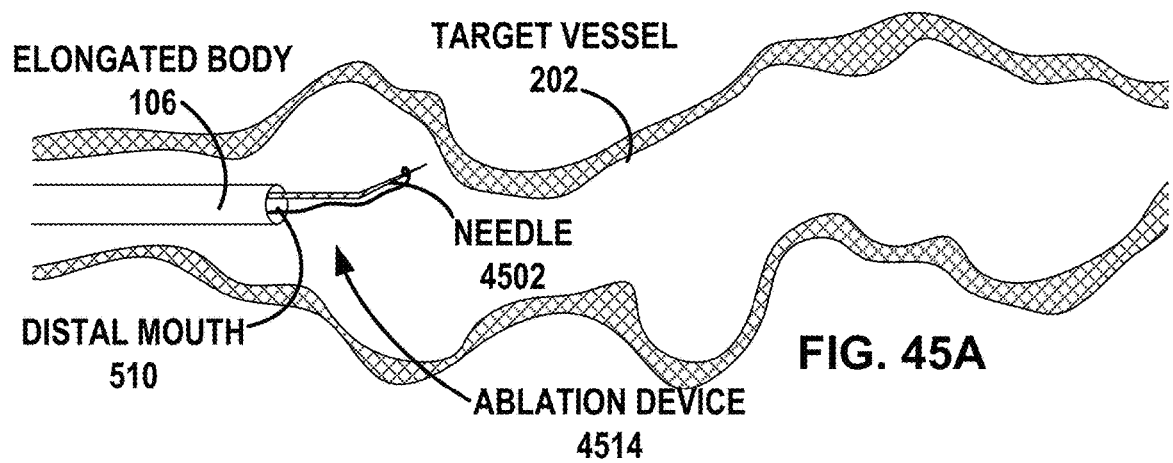
FIGS. 45A-45C are conceptual diagrams illustrating an example stitching technique for ablating a target vessel.
Figure 45B:
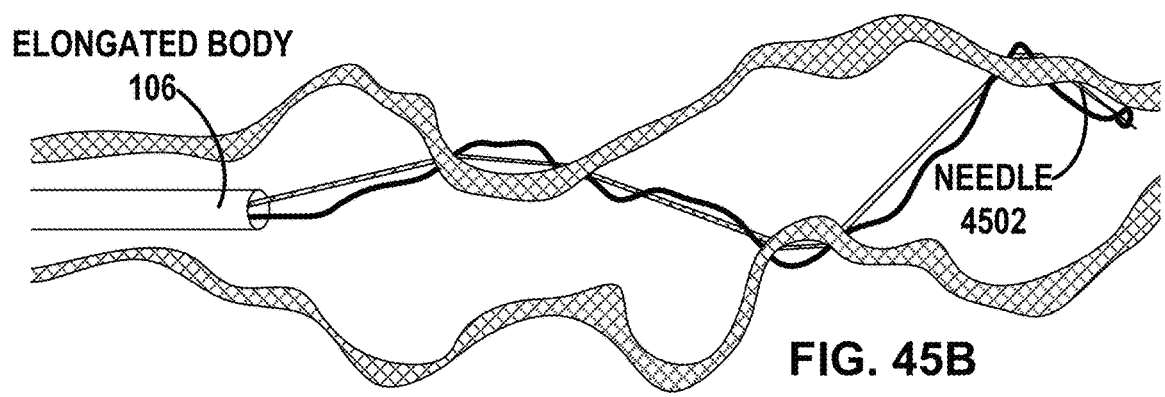
Figure 45C:
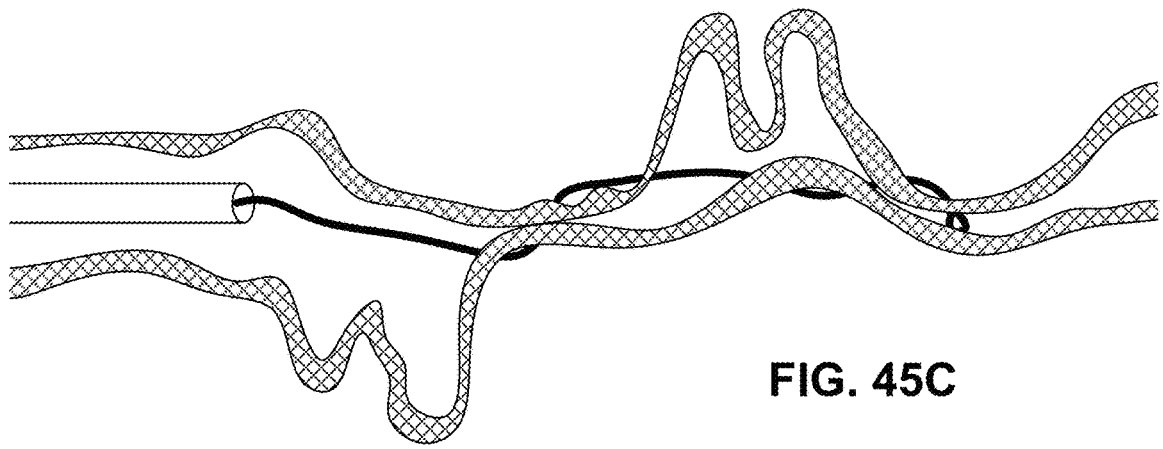

FIGS. 45A-45C are conceptual diagrams illustrating an example technique for mechanically ablating a target vessel 202. Additionally or alternatively to a rotational agitator as described in previous examples (e.g., agitator 204 of FIG. 2), in the example of FIGS. 45A-45C, ablation device 4514 (e.g., ablation device 114 of FIG. 1) includes a vessel agitator in the form of a needle 4502 deployed from distal catheter mouth 510 (FIG. 45A). Needle 4502 is configured to stitch a thread or suture through target vessel wall(s) at multiple locations (FIG. 45B). Needle 4502 may then be withdrawn back through catheter mouth 510, and the suture may be pulled tight to collapse the target vessel 202 radially and/or longitudinally inward on itself (FIG. 45C).

Additionally or alternatively, the clinician may deploy a "reverse" stent configured to expand radially outward and rigidly anchor to the target vessel 202. Upon removal of the delivery system, the reverse stent will collapse the vein inward on itself.

Figure 46:
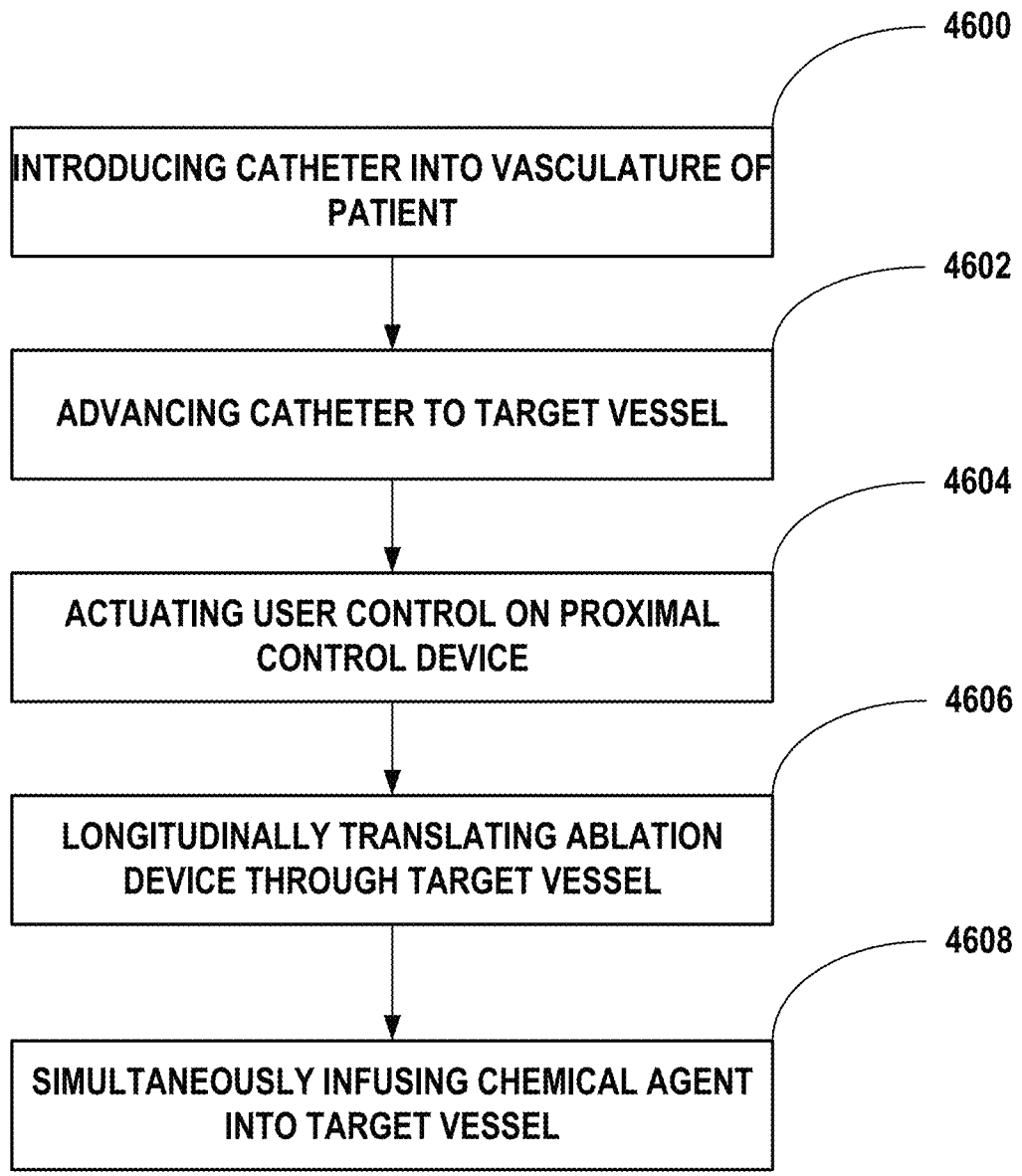
FIG. 46 is a flow diagram illustrating an example technique for ablating a target vessel of a patient's vasculature.

FIG. 46 is a flow chart illustrating a technique for ablating a target vessel 202 (FIG. 2), such as a varicose vein. The technique may include inserting a catheter 102 (FIG. 1) into a vasculature of a patient (at step 4600). The technique further includes advancing the catheter 102 to the target vessel 202 (at step 4602), and actuating a user control 212 on control device 112 operatively coupled to a proximal portion 108 of the catheter 102 (at step 4604). The control device 112 longitudinally translates a distal ablation device 114 through the target vessel 202 (at step 4606), and simultaneously infuses a chemical agent 208 into the target vessel (at step 4608). Additionally or alternatively, the control device 112 actuates a motion, such as a rotation, vibration, or oscillation, of a mechanical agitator 204.

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1, and embodiments described in other sections may apply to and be combined with embodiments described within the "Topic 1" section.

To increase the clarity of various features, other features are not labeled in each figure.

The various features and processes described above may be used independently of one another or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, parallel, or some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless expressly stated otherwise, or otherwise understood within the context as used, is generally intended to convey that certain embodiments include, while other embodiments do not include, certain features, elements and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless expressly stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

While certain example embodiments have been described, these embodiments have been presented by way of example only and are not intended to limit the scope of the inventions disclosed herein. Thus, nothing in the foregoing description implies that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

What is claimed is:

1. A vein ablation system, comprising:
a catheter having an elongated body;
an ablation device at a distal portion of the elongated body;
a control device at a proximal portion of the elongated body, the control device comprising a single actuator configured to simultaneously control an injection of a chemical agent into a target vessel and a defined movement of the ablation device, wherein a rate of the injection of the chemical agent into the target vessel and a rate of the defined movement of the ablation device is customizable relative to one another; and
a rate input configured to control the rate of the injection of the chemical agent into the target vessel and the rate of the defined movement of the ablation device.

2. The vein ablation system of claim 1, wherein the defined movement is a longitudinal translation of the ablation device through the target vessel.

3. The vein ablation system of claim 2, wherein the rate input is configured to control the rate of the injection of the chemical agent relative to a distance of the longitudinal translation of the ablation device.

4. The vein ablation system of claim 1, wherein the defined movement is a rotation of the ablation device about a central longitudinal axis.

5. The vein ablation system of claim 4, wherein the rate input is configured to control the rate of the injection relative to a number of rotations of the ablation device.

6. The vein ablation system of claim 1, wherein the defined movement is a vibration of the ablation device about a central longitudinal axis.

7. The vein ablation system of claim 1, wherein the defined movement is an agitation of the ablation device about a central longitudinal axis.

8. The vein ablation system of claim 1, wherein the ablation device defines a sinusoidal shape, and wherein the ablation device is configured to ablate the target vessel via the defined movement.

9. The vein ablation system of claim 8, wherein a distal portion of the ablation device comprises a spherical tip.

10. The vein ablation system of claim 1, further comprising a motor operatively coupled to the ablation device and configured to cause the ablation device to perform the defined movement when power is supplied to the motor.

11. The vein ablation system of claim 10, wherein the motor is configured to cause the injection of the chemical agent into the target vessel when power is supplied to the motor.

12. The vein ablation system of claim 1, wherein the chemical agent comprises a sclerosant.

13. The vein ablation system of claim 1, wherein the chemical agent is configured to be injected through the elongated body about the ablation device.

14. The vein ablation system of claim 1, wherein the control device further comprises a distance display configured to indicate a distance between the control device and the ablation device.

15. The vein ablation system of claim 14, wherein the distance display comprises a plurality of demarcations configured to indicate a distance between the control device and the ablation device.

16. The vein ablation system of claim 15, wherein the distance display is configured to indicate the rate of the injection of the chemical agent into the target vessel.

17. The vein ablation system of claim 1, wherein the control device further comprises a sliding mechanism configured to longitudinally translate the ablation device.

18. The vein ablation system of claim 1, wherein the chemical agent is configured to be injected through the ablation device.

19. The vein ablation system of claim 1, wherein the ablation device comprises a microtube, and wherein the ablation device is configured to ablate the target vessel via the defined movement.

20. The vein ablation system of claim 19, wherein the microtube defines a fluid aperture, and wherein the chemical agent is configured to be injected through the microtube.

* * * * *